United States Patent [19]

Taylor et al.

[11] Patent Number: 5,449,345
[45] Date of Patent: Sep. 12, 1995

[54] DETACHABLE AND REUSABLE DIGITAL CONTROL UNIT FOR MONITORING BALLOON CATHETER DATA IN A SYRINGE INFLATION SYSTEM

[75] Inventors: Steven R. Taylor; Fred P. Lampropoulos, both of Salt Lake City; Thomas D. Stout, Sandy; Brian W. Stevens, Pleasant Grove; Arlin D. Nelson, Midvale; Christopher L. Durham, Salt Lake City, all of Utah

[73] Assignee: Merit Medical Systems, Inc., South Jordan, Utah

[21] Appl. No.: 221,351

[22] Filed: Mar. 30, 1994

Related U.S. Application Data

[63] Continuation-in-part of Ser. No. 26,431, Mar. 4, 1993, Pat. No. 5,385,549, which is a continuation of Ser. No. 664,587, Mar. 4, 1991, Pat. No. 5,201,753, which is a continuation-in-part of Ser. No. 324,938, Mar. 17, 1989, Pat. No. 5,135,488.

[51] Int. Cl.$^6$ .................. A61M 29/00; A61M 1/00
[52] U.S. Cl. ................................ 604/100; 604/121
[58] Field of Search ............... 604/118, 121, 97–100, 604/189, 246

[56] References Cited

U.S. PATENT DOCUMENTS

| | | |
|---|---|---|
| 383,940 | 6/1888 | Brinkerhoff . |
| 404,105 | 5/1889 | Overlach . |
| 446,125 | 2/1891 | Schirmer . |
| 577,682 | 2/1897 | Eissner . |

(List continued on next page.)

FOREIGN PATENT DOCUMENTS

| | | |
|---|---|---|
| 545415 | 8/1957 | Canada . |
| 0119296 | 9/1984 | European Pat. Off. . |
| 0230966A3 | 1/1985 | European Pat. Off. . |
| 0149866 | 7/1985 | European Pat. Off. ........ 604/100 X |
| 0396353 | 11/1990 | European Pat. Off. ........ 604/100 X |
| 1242737 | 8/1960 | France . |
| 2083364 | 3/1982 | United Kingdom . |

(List continued on next page.)

OTHER PUBLICATIONS

Advertising brochure of Spectramed, Inc.; produce prochure for "Controlease Disposable Control Syringe"; and product brochure for control syringe of COEUR Laboratories, Inc., undated.

"Clearing the Path for a Healthy Heart," *Tristate: The Cincinnati Enquirier Magazine*, Oct. 23, 1988.

(List continued on next page.)

*Primary Examiner*—John D. Yasko
*Assistant Examiner*—Adam J. Cermak
*Attorney, Agent, or Firm*—Workman Nydegger Seeley

[57] ABSTRACT

An electronically controlled syringe system for connection to a balloon catheter or other balloon-type member and for monitoring, displaying and optionally recording inflation or deflation data when the syringe system is used to inflate or deflate the balloon of the catheter or other balloon-type member. A syringe having a barrel and a syringe plunger is selectively operable to increase fluid pressure applied to the balloon catheter or other balloon member by sliding the plunger further into the barrel. Positive pressure applied to the balloon catheter or member is released by withdrawing the syringe plunger toward the rear of the barrel. A piezoresistive semiconductor transducer placed in fluid communication with the fluid pressure applied by the syringe, senses the fluid pressure and outputs an electrical signal representative of that pressure. The electric signal is input to a controller where the signal is digitally processed so as to derive and record therefrom electronic data representing the magnitude of applied fluid pressure, and so as also to derive the length of time that fluid pressure is applied. The electronic data representing this information is displayed and optionally recorded. In one embodiment, the electronic signal is received by a detachable and reusable electronic circuit module that detachably mounts to a housing formed on the syringe barrel.

39 Claims, 44 Drawing Sheets

U.S. PATENT DOCUMENTS

| | | |
|---|---|---|
| 730,054 | 6/1903 | Sheets . |
| 1,661,818 | 3/1928 | Cook . |
| 1,707,880 | 4/1929 | Sheets . |
| 2,656,836 | 10/1953 | Hickey . |
| 2,672,866 | 3/1954 | Kater . |
| 2,699,168 | 1/1955 | Lewis . |
| 2,724,385 | 11/1955 | Lockhart . |
| 2,736,315 | 2/1956 | Feeney . |
| 2,764,978 | 10/1956 | Everett . |
| 3,080,866 | 3/1963 | Friedman . |
| 3,388,941 | 6/1968 | Marcus ................................ 294/4 |
| 3,478,937 | 11/1969 | Solowey ............................ 222/386 |
| 3,491,757 | 1/1970 | Arce . |
| 3,529,596 | 9/1970 | Garner . |
| 3,698,381 | 10/1972 | Federico et al. . |
| 3,720,199 | 3/1973 | Rishton et al. . |
| 3,884,229 | 5/1975 | Raines et al. . |
| 3,931,822 | 1/1976 | Marici . |
| 3,966,358 | 6/1976 | Heimes et al. ....................... 417/12 |
| 3,985,123 | 10/1976 | Herzlinger et al. . |
| 3,992,926 | 11/1976 | Berryhill ............................... 73/80 |
| 4,016,871 | 4/1977 | Schiff . |
| 4,057,050 | 11/1977 | Sarstedt . |
| 4,063,662 | 12/1977 | Drummond et al. ................ 222/31 |
| 4,086,653 | 4/1978 | Gernes ................................ 364/564 |
| 4,106,002 | 8/1978 | Hogue, Jr. ........................... 340/626 |
| 4,182,344 | 1/1980 | Benson ............................. 128/207.15 |
| 4,254,773 | 3/1981 | Waldbillig . |
| 4,261,360 | 4/1981 | Perez . |
| 4,266,550 | 5/1981 | Bruner . |
| 4,267,846 | 5/1981 | Kontos ................................ 128/765 |
| 4,285,340 | 8/1981 | Gezari et al. ..................... 128/205.24 |
| 4,323,071 | 4/1982 | Simpson et al. . |
| 4,332,254 | 6/1982 | Lundquist . |
| 4,370,982 | 2/1983 | Reilly ................................. 604/98 |
| 4,384,470 | 5/1983 | Fiore .................................. 73/4 R |
| 4,404,974 | 9/1983 | Titus .................................. 128/670 |
| 4,418,392 | 11/1983 | Hata ................................... 364/571 |
| 4,439,185 | 3/1984 | Lundquist ........................... 604/97 |
| 4,444,335 | 4/1984 | Wood et al. ......................... 222/43 |
| 4,446,715 | 5/1984 | Bailey ................................ 73/1 R |
| 4,446,867 | 5/1984 | Leveen et al. . |
| 4,460,355 | 7/1984 | Layman ............................. 604/118 |
| 4,466,426 | 8/1984 | Blackman . |
| 4,504,268 | 3/1985 | Herlitze . |
| 4,522,194 | 6/1985 | Normann . |
| 4,526,196 | 7/1985 | Pistillo ................................ 137/557 |
| 4,546,760 | 10/1985 | Suzuki et al. . |
| 4,557,269 | 12/1985 | Reynolds et al. ................... 128/675 |
| 4,568,335 | 2/1986 | Updike et al. ...................... 604/211 |
| 4,573,978 | 3/1986 | Reilly ................................ 604/240 |
| 4,583,917 | 4/1986 | Shah .................................. 417/63 |
| 4,583,974 | 4/1986 | Kokernak ........................... 604/211 |
| 4,585,010 | 4/1986 | Ascer et al. ........................ 128/673 |
| 4,596,255 | 6/1986 | Snell et al. ......................... 128/697 |
| 4,597,381 | 7/1986 | Oumi et al. ........................ 128/6 |
| 4,600,015 | 7/1986 | Evans et al. ....................... 128/780 |
| 4,601,701 | 7/1986 | Mueller, Jr. ........................ 604/83 |
| 4,610,256 | 9/1986 | Wallace ............................. 128/675 |
| 4,621,646 | 11/1986 | Bryant ............................... 128/692 |
| 4,651,783 | 3/1987 | Demer et al. . |
| 4,658,829 | 4/1987 | Wallace ............................. 128/672 |
| 4,662,355 | 5/1987 | Pieronne et al. . |

(List continued on next page.)

FOREIGN PATENT DOCUMENTS

| | | | |
|---|---|---|---|
| WO81/02664 | 10/1981 | WIPO . | |
| 9217721 | 11/1990 | WIPO | ........................... 604/100 X |
| 9217221 | 10/1992 | WIPO | ............................... 604/100 |

OTHER PUBLICATIONS

"Coronary Angioplasty," Krames Communications, 1985.

"Good News for People with Only Two Hands," SciMed Life Systems, Inc. (undated).

"Health—Critics of Angioplasty Worry About Inflated Success Claims," *U.S. News & World Report*, Jul. 25, 1988, p. 65.

"Inflation Pro: A New Dual-Support System for Angioplasty," Baxter Healthcare Corporation, undated.

"PTCA Safe and Efficacious Performed Together With Diagnostic Angiography in Selected Cases," *Cardiovascular News*, May 1988, p. 8.

"USCI Wizard Disposable Inflation Device," C. R. Bard, Inc.

"ACS Accessories Offer Optimum Efficiency in Your Angioplasty Procedures," Eli Lilly and Company, undated.

Advertising brochure of North American Instrument Corporation entitled "The NAMIC 10cc Angiographic Syringe Features." (undated).

Product catalog of Mansfield (1988).

Advertisement brochure of Mansfield entitled: "The Mansfield Trak Series." (1987).

Advertisement brochure of Mansfield entitled: "The (List continued on next page.)

U.S. PATENT DOCUMENTS

| | | | |
|---|---|---|---|
| 4,672,974 | 6/1987 | Lee | 128/673 |
| 4,710,179 | 12/1987 | Haber | 604/211 |
| 4,715,854 | 12/1987 | Vaillancourt | 604/191 |
| 4,723,938 | 2/1988 | Goodin et al. | 604/99 |
| 4,743,230 | 5/1988 | Nordquest | 604/97 |
| 4,756,706 | 7/1988 | Kerns et al. | 604/66 |
| 4,758,223 | 7/1988 | Rydell | 604/90 |
| 4,781,192 | 11/1988 | Demer . | |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,817,639 | 4/1989 | Davis et al. | 128/748 |
| 4,819,637 | 4/1989 | Dormandy | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,864 | 6/1989 | Peterson | 604/100 |
| 4,858,615 | 8/1989 | Meinema | 128/668 |
| 4,865,581 | 9/1989 | Lundquist et al. | 600/18 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,004,472 | 4/1991 | Wallace | 606/194 |
| 5,009,662 | 4/1991 | Wallace | 606/192 |
| 5,011,468 | 4/1991 | Lundquist et al. | 600/18 |
| 5,019,041 | 5/1991 | Robinson | 604/97 |
| 5,021,046 | 6/1991 | Wallace | 606/97 |
| 5,024,668 | 6/1991 | Peters et al. | 606/194 |
| 5,059,167 | 10/1991 | Lundquist et al. | 600/17 |
| 5,084,060 | 1/1992 | Freund et al. | 606/192 |
| 5,086,777 | 2/1992 | Hishii | 128/675 |
| 5,135,488 | 8/1992 | Foote et al. | 604/97 |
| 5,163,904 | 11/1992 | Lampropoulos et al. | 604/100 |
| 5,215,523 | 6/1993 | Williams | 604/97 |
| 5,218,970 | 6/1993 | Turnbull et al. | 128/748 |
| 5,259,838 | 11/1993 | Taylor et al. | 604/97 |
| 5,279,563 | 1/1994 | Brucker et al. | 604/98 |
| 5,318,533 | 6/1994 | Adams et al. | 604/97 |
| 5,368,565 | 11/1994 | Delong | 604/100 |

OTHER PUBLICATIONS

Mansfield Series 3000 Intra-Aortic Balloon Pump". (1988).

Advertisement brochure of Medex, Inc. for Medflator inflation system. (1991).

Advertisement brochure of Mansfield for Digiflator inflation syringe with an attached digital pressure gauge (undated).

Mansfield instruction brochure for the Digiflator. (1991).

Advertisement brochure of Condor Medical for Transflator Infrared System. (undated).

Advertisement brochure of BasTek for the Inter/Com Inflation System Computer. (undated).

Brochure of BasTek disclosing Inter/Com and inflation syringe entitled: "Reach Out and Touch the Future". (undated).

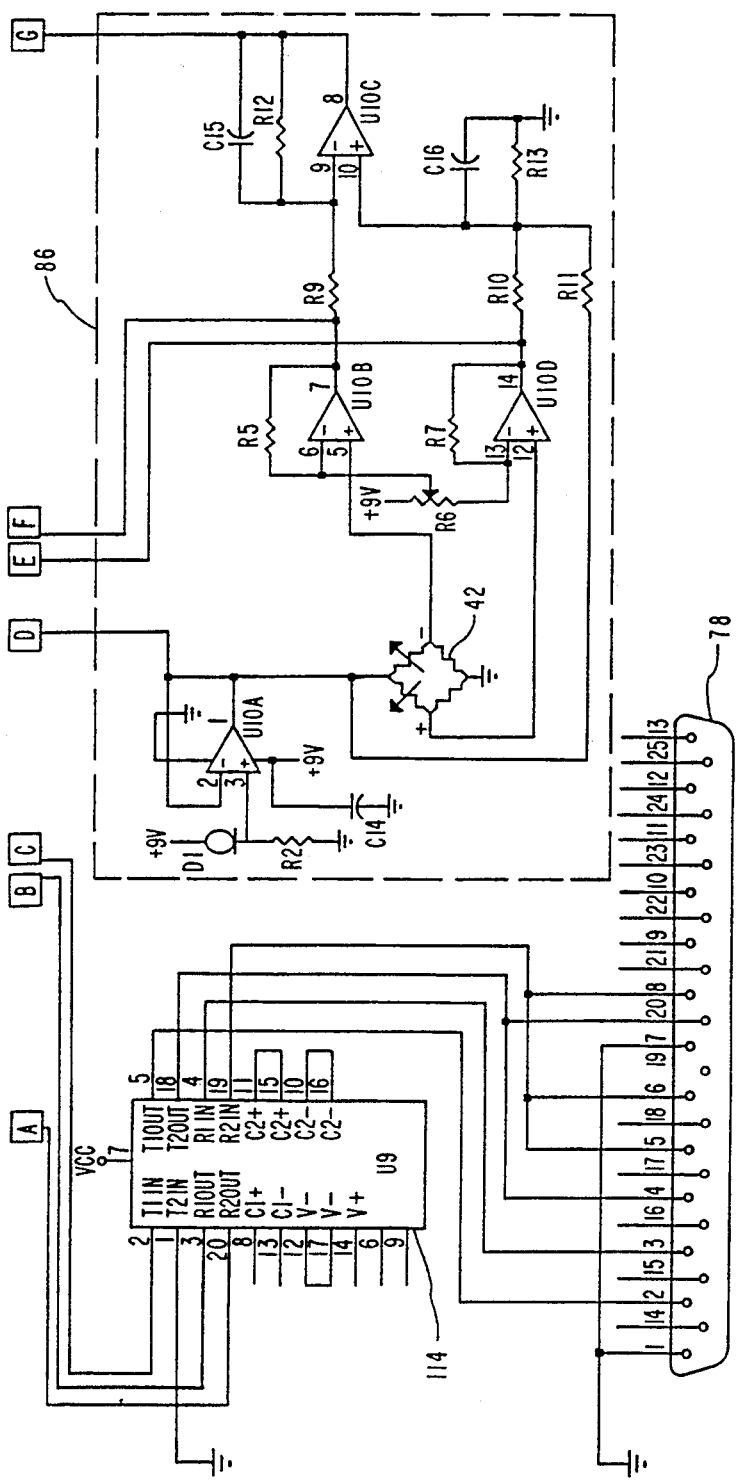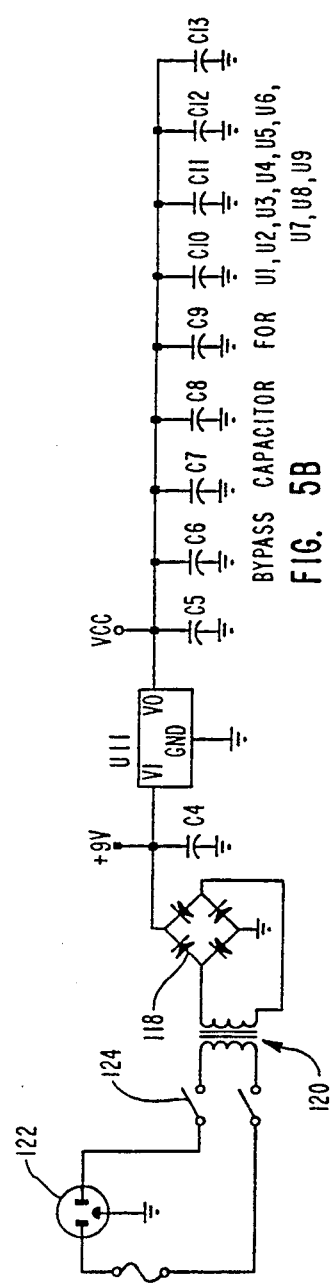
FIG. 5B

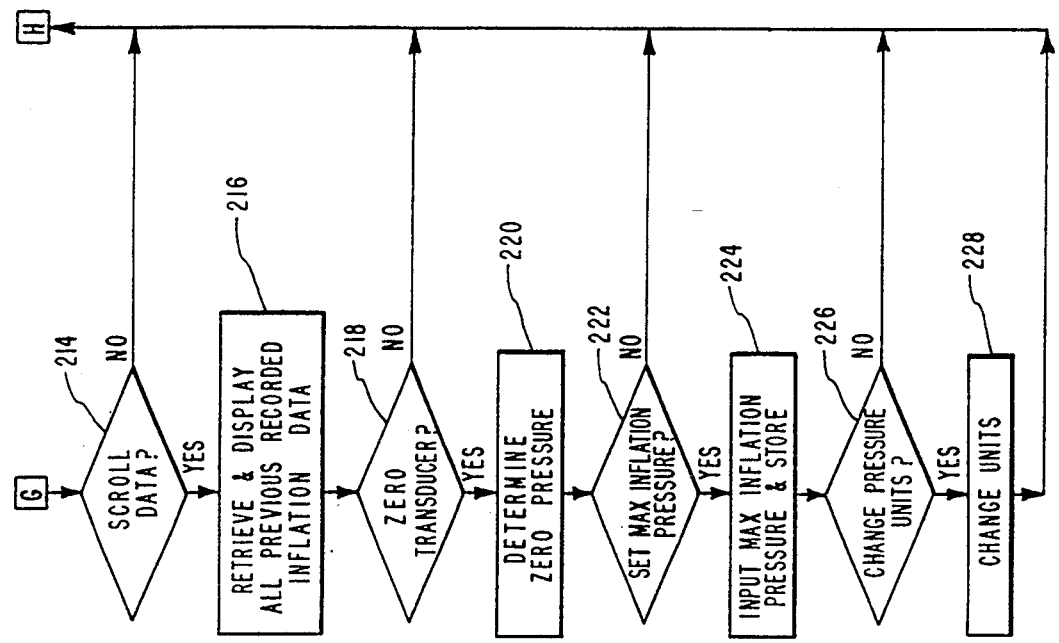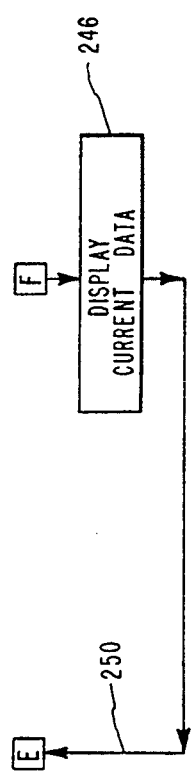
FIG. 6G

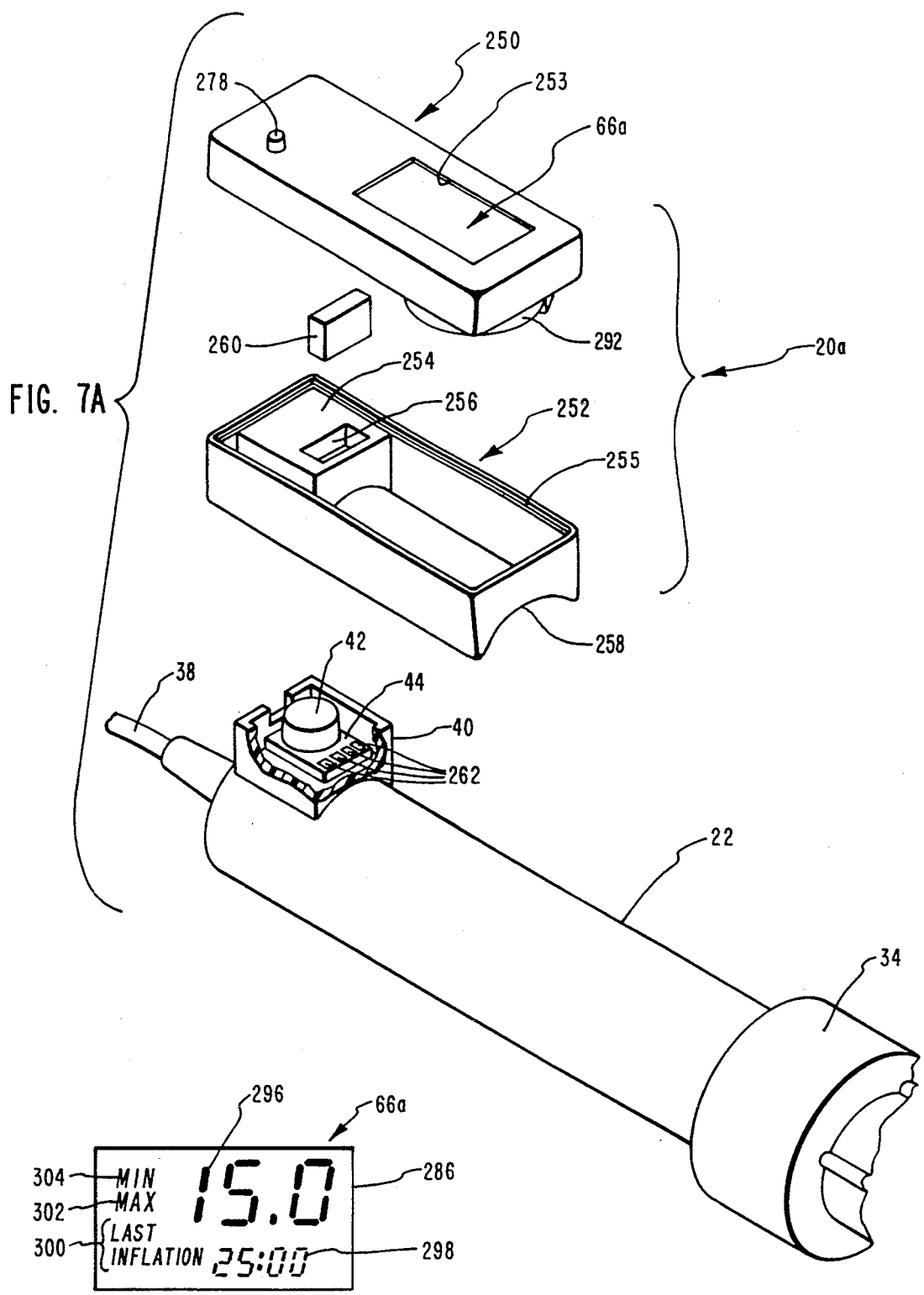

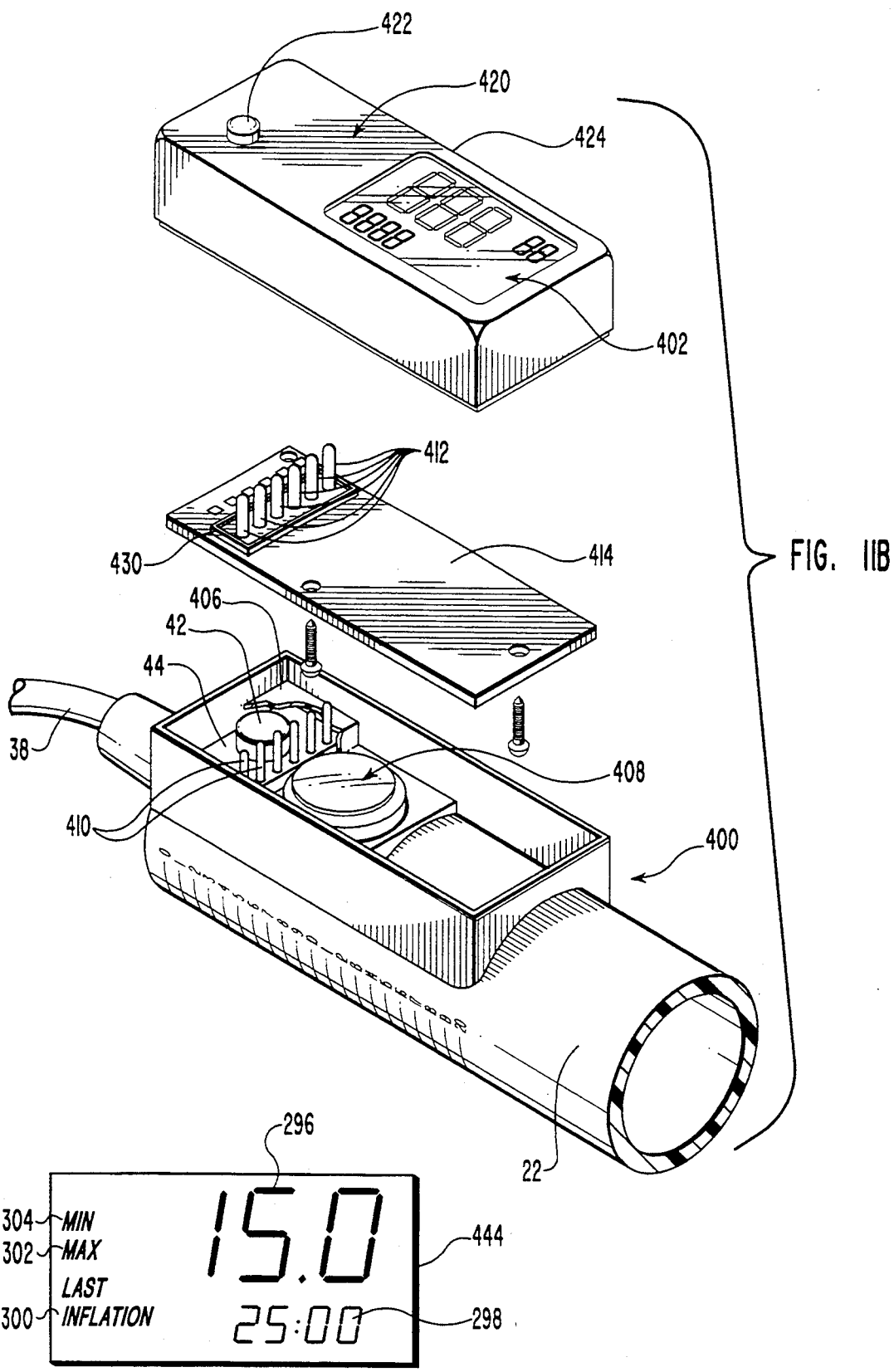

DETACHABLE AND REUSABLE DIGITAL CONTROL UNIT FOR MONITORING BALLOON CATHETER DATA IN A SYRINGE INFLATION SYSTEM

RELATED APPLICATION INFORMATION

This application is a continuation-in-part of U.S. application Ser. No. 08/026,431 filed Mar. 4, 1993, now U.S. Pat. No. 5,385,549 which is a continuation of U.S. application Ser. No. 07/664,587 filed Mar. 4, 1991, now U.S. Pat. No. 5,201,753, which is a continuation-in-part of U.S. application Ser. No. 07/324,938, filed Mar. 17, 1989, now U.S. Pat. No. 5,135,488.

BACKGROUND OF THE INVENTION

1. Field of the Invention

This invention relates to syringe systems that are used for controlling and monitoring conditions of inflation or deflation of a balloon-tipped catheter, and more particularly to a reusable and detachable electronic module used to electronically monitor the syringe system, or to provide electronic data used to monitor the syringe system.

2. The Present State of the Art

Balloon-tipped catheter systems have been known and used in the medical arts for a number of years in connection with a variety of different kinds of procedures which are used, for example, in various fields of medicine, such as urology, gynecology, cardiology and others. Particularly in connection with the treatment of coronary artery disease, the use of balloon-tipped catheters and their associated syringe systems have become widely used.

Coronary artery disease is the narrowing of the arteries that feed oxygen-rich blood to the heart. Since the heart is a muscle whose primary job is to pump oxygenated blood throughout the body, the heart needs adequate amounts of oxygen to properly function. Thus, when the coronary arteries which are located on the top of the heart and through which oxygenated blood is returned to the heart become narrowed or blocked (a condition known as "stenosis"), angina can result. Angina is a symptom of coronary artery disease characterized by chest pain or pressure that can radiate to the arm or jaw, and is caused by a lack of oxygen-rich blood to the heart muscle. Coronary artery disease with its accompanying symptom of angina results from atherosclerosis, which is a build up of waxy material called plaque inside the arteries. When this happens, under exertion or stress, the heart demands more oxygen but the narrowed coronary arteries cannot supply enough oxygen-rich blood to meet the demand, resulting in angina. Unless corrected, this condition can lead to a fatal heart attack.

Initially, there were two basic ways to treat coronary artery blockages: with medicine or by performing coronary artery by-pass surgery. Various kinds of medication could be administered which would decrease the work of the heart by slowing the heart rate, dilating the blood vessels, or lowering blood pressure. However, such medicinal treatment did not cure coronary artery blockage, which thus remained and which would therefore continue to present a risk that at some point the blockage would become serious enough to require surgical intervention.

In coronary artery by-pass surgery, a blood vessel from the chest or leg is grafted beyond the point of blockage so that the blood detours past the blockage in order to reach the heart. In some severe cases, multiple by-passes are performed. As is well known, coronary artery by-pass surgery is expensive, is a high risk procedure and often requires prolonged hospitalization and recovery periods.

Later on, another method for treating coronary artery disease was developed, called balloon coronary angioplasty, or more technically, percutaneous transluminal coronary angioplasty (PTCA). PTCA is a much less traumatic procedure than coronary artery by-pass surgery. PTCA takes about two hours and can be done under local anesthesia, with the result that often a patient can be back on his feet and active in a matter of days. Because PTCA is much less expensive and less traumatic than by-pass surgery and yet in many cases still effectively removes blockage, PTCA has experienced a dramatic increase in the number of such procedures performed each year. Since coronary artery disease remains the number one cause of death, PTCA may be expected to continue to play an important role in the treatment of coronary artery disease.

In performing PTCA, an introducer sheath is inserted through an incision made in the groin or arm area and into the corresponding artery of, such as the femoral artery. An x-ray sensitive dye is injected into the coronary artery through a catheter that is introduced through the sheath. The dye enables the doctor, through the use of real time x-ray techniques, to clearly view the arteries on a television monitor and to thereby locate the artery blockage. A balloon-tipped catheter with a guide wire at the end of it is then advanced through the artery to the point of the blockage with the help of the x-ray monitor.

As schematically illustrated in FIGS. 1A–1C, the balloon catheter 10 is advanced to the middle of the blockage 12. The catheter 10, which is filled with a fluid and is coupled at its other end to an inflation syringe, is manipulated by the cardiologist. Once the balloon catheter is in place, utilizing the inflation syringe the balloon is inflated for 20 to 60 seconds as shown in FIG. 2B. The balloon is then deflated to permit sufficient blood flow to the heart and this procedure is then repeated typically several times to compress the plaque on the arterial wall, as shown in FIG. 1C. After the results are checked, the balloon catheter and guide wire are then removed.

As will be appreciated, notwithstanding that PTCA is a much less traumatic procedure than coronary artery by-pass surgery, nonetheless exacting control with respect to inflation pressure, and duration of the inflation and deflation periods is essential to the safety of the patient. For example, when the balloon catheter is completely inflated so as to begin compressing the plaque, blood flow to a region of the heart is thereby temporarily shut off. This creates a condition known as myocardial ischemia, which can initiate cardiac arrest. Accordingly, the pressure exerted on the artery by the balloon catheter as well as the duration of the blockage created by inflating the balloon catheter must both be carefully controlled by the attending cardiologist and other personnel. The inflation pressures and duration of each inflation and deflation must be based on the cardiologist's assessment of the health of the patient and the patient's ability to withstand such a temporary stoppage of blood flow to the heart.

In the past, PTCA syringe systems have been equipped with standard analog or Bourdon-tube gauges that are utilized to sense and read the pressure used for purposes of inflating a balloon catheter. Human observation of stop clocks and the like has been used to control the duration of the inflation and deflation.

While these prior art techniques have been widely used with success, there is still a serious risk of human error when using such systems. The gauges used on such syringe systems are often awkward and difficult to accurately read, and are also subject to malfunction. Thus, improper recording of inflation pressure and/or duration of either inflation or deflation may occur. Accordingly, there is a need for the cardiologist and/or clinician to be able to improve the degree of control and precision with respect to monitoring of PTCA data. There is also a need to be able to accurately record the PTCA data so that in the event of any later question with respect to whether the procedure was properly carried out, there is an accurate record from which to answer such questions.

Many types of syringe inflation systems have been proposed or used in the art which, to varying degrees, provide for more careful monitoring and/or recording of PTCA data. Two of the first commercially successful syringe inflation systems which provided digital monitoring of PTCA data are the Intellisystem ® and Monarch ® syringe inflation systems of Merit Medical Systems, Inc., which are produced and sold under U.S. Pat. Nos. 5,135,488 and 5,201,753 (hereinafter the "'488" and "'753" patents) respectively.

The Intellisystem ® syringe inflation system provides an inflation syringe with an attached semiconductor transducer mounted to the syringe barrel. The transducer output is connected by an electrical cable to a bedside monitor that digitally processes the transducer signal to provide a digital readout of various PTCA data, including the magnitude of each inflation and deflation and the duration of each inflation and deflation. The Monarch ® syringe inflation system provides an inflation syringe that has a miniaturized digital monitor mounted to the syringe barrel in an integral fashion.

After the PTCA procedure is complete, with the Intellisystem ® syringe inflation system, the inflation syringe with its attached transducer is disposed of. In the case of the Monarch ® syringe inflation system, the syringe with the attached miniature monitor is all completely disposed of.

There is great concern in the health care industry for keeping health care costs as low as possible. Thus, there is an ongoing need to find ways of providing syringe inflation systems which, like the Intellisystem ® and Monarch systems ®, are effective for monitoring PTCA data, but which are also less costly and minimize disposal of costly components. The present invention addresses this need.

SUMMARY OF THE INVENTION

The system and method of the present invention have been developed in response to the present state of the art, and in particular, in response to the problems and needs in the art not heretofore fully or completely solved by syringe inflation systems used in connection with PTCA procedures. However, it is not intended that the system and method of the present invention will necessarily be limited solely to PTCA procedures, since they will also find useful application with potentially many kinds of procedures which require the utilization of inflatable balloon members for various kinds of medical procedures. Thus, it is an overall object of the present invention to provide a system and method which provide for more cost effective, yet accurate measurement and monitoring of a balloon-type member.

Another important object of the present invention is to provide a system and method whereby state of the art electronic technology can be utilized at lower cost and with less waste to assist the cardiologist or clinician in accurately measuring, monitoring and/or optionally recording inflation pressures as desired when utilizing a syringe system to inflate a balloon catheter or other balloon-type member.

Another important object of the present invention is to provide an improved syringe system and electronic monitoring and recording system which increase the convenience and safe utilization of a balloon catheter or other balloon-type inflation member.

A further object of the present invention is to provide an improved syringe system which is digitally controlled and monitored by a reusable and detachable electronic circuit module that can be detached from the disposable control syringe for re-use in another system upon the completion of a procedure.

These and other objects and features of the present invention will become more fully apparent from the following more detailed description taken in conjunction with the drawings and claims, or may be learned by the practice of the invention.

Briefly summarized, the foregoing and other objects are achieved in an electronically monitored syringe system that is connected to a balloon catheter or other inflatable balloon-type device through tubing. The syringe comprises a barrel and a plunger selectively operable to increase fluid pressure applied to the balloon through the connecting tubing by sliding the plunger further into the barrel, and to then remove the applied pressure by returning the plunger to the rear of the barrel. A transducer for sensing fluid pressure applied by the syringe is placed in fluid communication with the syringe and the connecting tubing. The transducer thereby senses applied fluid pressure and outputs an electrical signal proportional to the sensed pressure. The electrical signal output by the transducer is then electronically processed so as to derive and record therefrom electronic data representing the magnitude of fluid pressure applied to the balloon or other balloon-type member, and so as also to derive the length of time that inflation pressure and deflation intervals are applied to the balloon or other balloon-type member, and the electronic data representing these parameters is then displayed and/or recorded. The system also comprises a display for selectively outputting a visual display of the magnitude of the applied pressure and the corresponding length of time that inflation or deflation is applied to the balloon or other balloon-type member.

The electronic control system used in conjunction with the system and method of the present invention may also be optionally designed to permit the selection and input of various control parameters such as a maximum positive inflation pressure that is to be applied, a maximum duration for applying positive inflation pressure, initializing the date and time of the procedure and/or retrieving and displaying inflation or deflation data previously recorded. In this manner, the system and method of the present invention provide not only more convenient operation of the syringe when inflating or deflating the balloon catheter or other balloon-type member, but also a much safer and more accurate procedure which can be used to effectively alert a cardiologist or clinician when the appropriate levels of pressure and duration thereof have been reached with respect to a particular inflation event. The system is thus efficient and easy to operate while at the same time providing improved convenience and overall safety, and also providing accurate documentation of all inflation data for later reference.

Importantly, the electrical signal output by the transducer is electronically processed by a reusable, detachable electronic circuit module that is operatively couplable to a syringe system. In this manner, the electronic circuit can be easily detached from the disposable syringe and tubing, and then re-used in another syringe system, thereby significantly reducing the cost. In this embodiment, the transducer may be optionally included as part of the detachable and reusable electronic circuit module, or the transducer may be mounted to the syringe barrel. Further, the display may be included as part of the detachable and reusable electronic circuit module, in which case the electronic control system is incorporated entirely within the detachable electronic circuit module. Alternatively, the display may be mounted to a remote console, in which case the electronic control system is incorporated within the remote console and the pressure data is transmitted directly to the remote console by the detachable electronic circuit module.

BRIEF DESCRIPTION OF THE DRAWINGS

The presently preferred embodiments and the presently understood best mode of the invention will be described with additional detail through use of the accompanying drawings, wherein corresponding parts are designated by the same reference numerals throughout, and in which:

FIGS. 5A and 5B taken together constitute a detailed electrical schematic diagram which illustrate, as an example, the presently preferred embodiment and presently understood best mode for implementing the electronic circuit means of the system and method of the present invention.

FIGS. 6E through 6G taken together illustrate a flow chart showing a second presently preferred method for programming the digital processor of the electronic circuit means utilized in the syringe system of FIGS. 2–5 in accordance with another method of the present invention.

FIG. 7A is a perspective illustration of a portion of the syringe system of FIG. 7, with portions of the electronic controller shown in exploded perspective to more particularly illustrate certain details thereof.

FIG. 7C is an illustration of the digital readout display which particularly illustrates the nature of the information displayed thereon when utilizing the electronic control system and syringe of FIG. 7.

FIG. 11B is a perspective illustration of a portion of the syringe system of FIG. 11, with portions of the detachable electronic circuit module shown in exploded perspective to more particularly illustrate certain details thereof.

FIG. 11D is a schematic illustration of the digital readout display which particularly illustrates the nature of the information displayed thereon when utilizing the detachable electronic circuit module of FIG. 11.

DETAILED DESCRIPTION OF THE PRESENTLY PREFERRED EMBODIMENTS

I. THE SYSTEM

A. General Environment and Intended Utility of the System

Figure 1A:
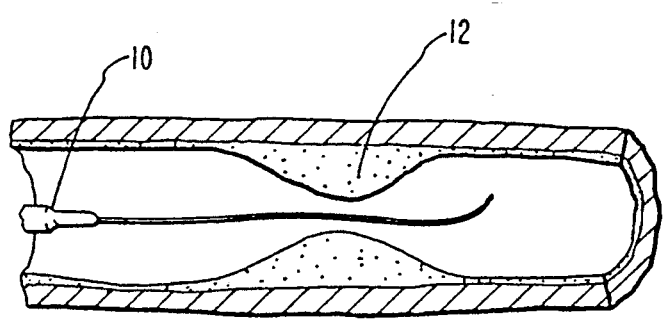
FIGS. 1A–1C are partial cross-sectional views which schematically illustrate a conventional balloon catheter being placed within a vessel such as a coronary artery containing a blockage, and showing the manner in which the blockage is essentially removed by inflation of the balloon catheter.
Figure 1B:
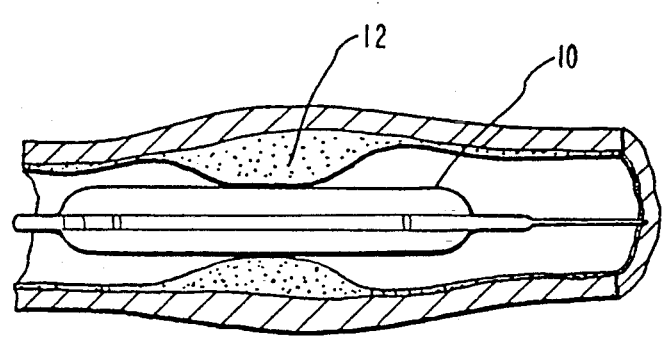
Figure 1C:
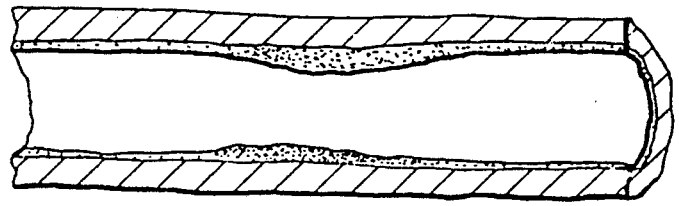

As noted above, the system and method of the present invention have been developed in response to specific needs which have been found to exist in connection with techniques that are currently in use according to the present state of the art which has developed in connection with PTCA procedures. As described in connection with FIGS. 1A-1C, PTCA is a surgical procedure used for treating coronary artery disease wherein a balloon catheter 10 is inserted through an incision made in the groin or in an arm and is then advanced through the artery by means of a guide catheter and assisted by means of an x-ray sensitive dye. The balloon catheter 10 is advanced until it is located at the middle of the blockage 12. Once located at the middle of the blockage 12, the balloon of catheter 10 is then inflated (see FIG. 1B) to a pressure that is typically between 7 and 10 atmospheres for a duration of between 20 to 60 seconds. The balloon is then deflated for a sufficient interval to permit adequate blood flow to the heart, and the procedure is then repeated a number of times, slightly increasing the inflation pressure each time so as to further compress and thereby reduce the blockage 12 created by the buildup of plaque along the wall of the artery. Once this series of inflations is completed and the artery is cleared, as shown in FIG. 1C, the balloon catheter 10 is removed.

While the presently preferred embodiments of the system and method of the present invention are particularly useful in connection with the aforementioned PTCA procedure, the system and method of the invention are not intended to be necessarily limited to use in connection with PTCA. Rather, it is contemplated that the system and method of the invention will find useful application with respect to any procedure requiring the use of an inflatable balloon-type member. Moreover, while in PTCA the inflation pressure which is applied to the balloon catheter 10 is applied hydraulically by means of the syringe and connecting tubing which are all filled with a sterile liquid such as a solution of saline and contrast medium, in some potential applications it may be necessary or desirable to apply the inflation pressure pneumatically. Accordingly, as used herein the term "fluid pressure" is intended to apply either to a hydraulically or a pneumatically applied inflation pressure.

Furthermore, as will be appreciated by those of ordinary skill in the art, while the system and method as described in reference to the preferred embodiments herein illustrate the invention as implemented using state of the art digital processing design and corresponding program instructions, the system and method could also be implemented and carried out using a hardware design which accomplishes the necessary electronic processing, which is thus intended to be embraced within the scope of the invention.

B. The Presently Preferred Embodiments of the Syringe System and Electronic Controller: FIG. 2-5, 7-9 and 11-17.

1. FIGS. 2-5

The system of the present invention is comprised of a syringe that is connected to a balloon catheter or other balloon-type member through tubing. The syringe is used to apply fluid pressure to the balloon of the catheter or other balloon-type member through the tubing so as to inflate the balloon or balloon member when desired, and can also be used to deflate the balloon catheter or balloon member after it has been inflated for a selected duration. The system is also comprised of a transducer means for sensing applied fluid pressure (including the absence thereof during deflation intervals) and for outputting an electrical signal proportional to the sensed fluid pressure. The transducer means is thus preferably in fluid communication with the syringe and the tubing connected to the balloon catheter or other balloon-type member.

Figure 2:
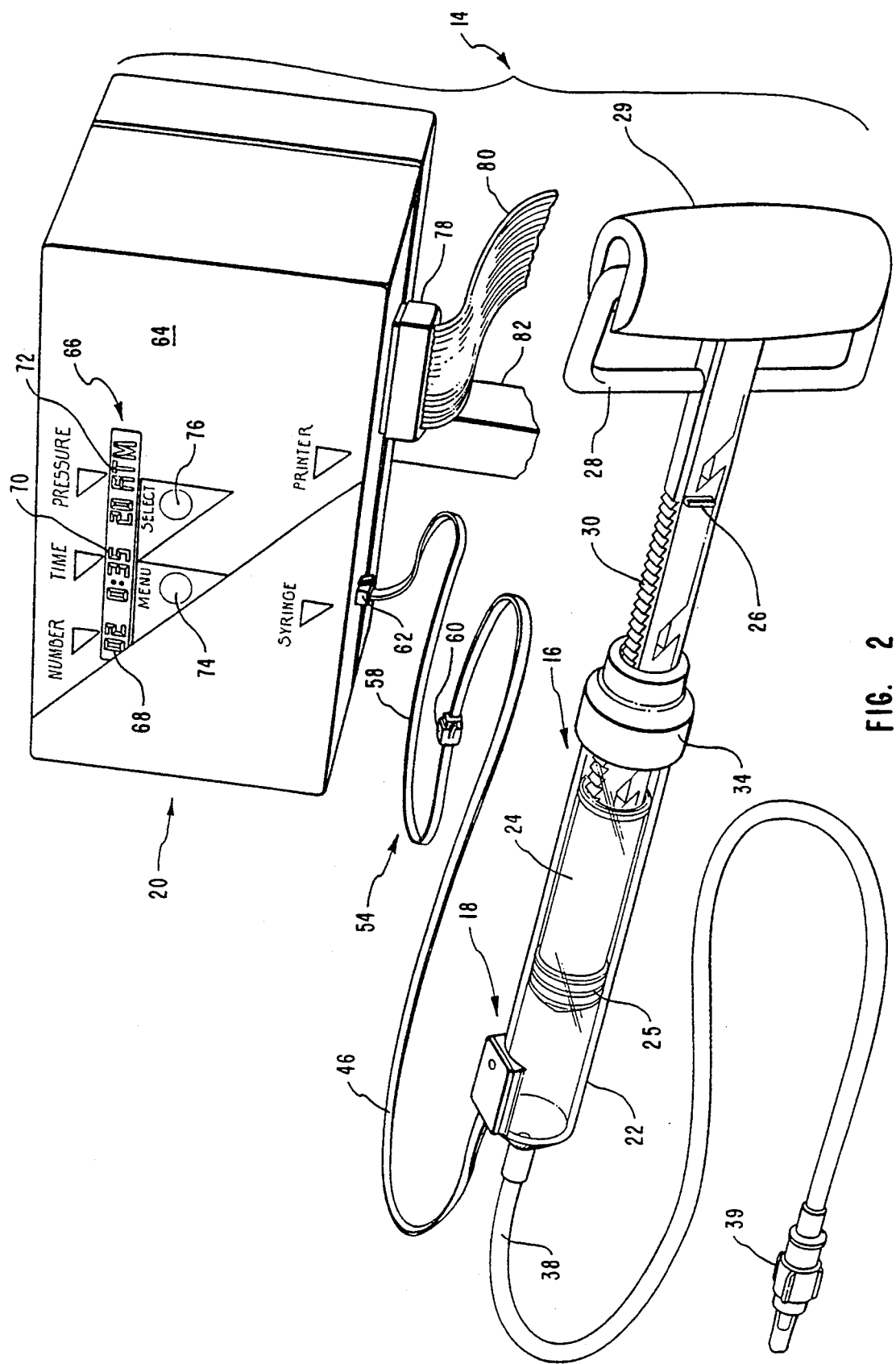
FIG. 2 is a perspective illustration showing the system of the present invention, and in particular illustrating a syringe with tubing for connection to a balloon catheter, and a transducer means mounted on the syringe and electrically connected to an electronic controller.
Figure 3:
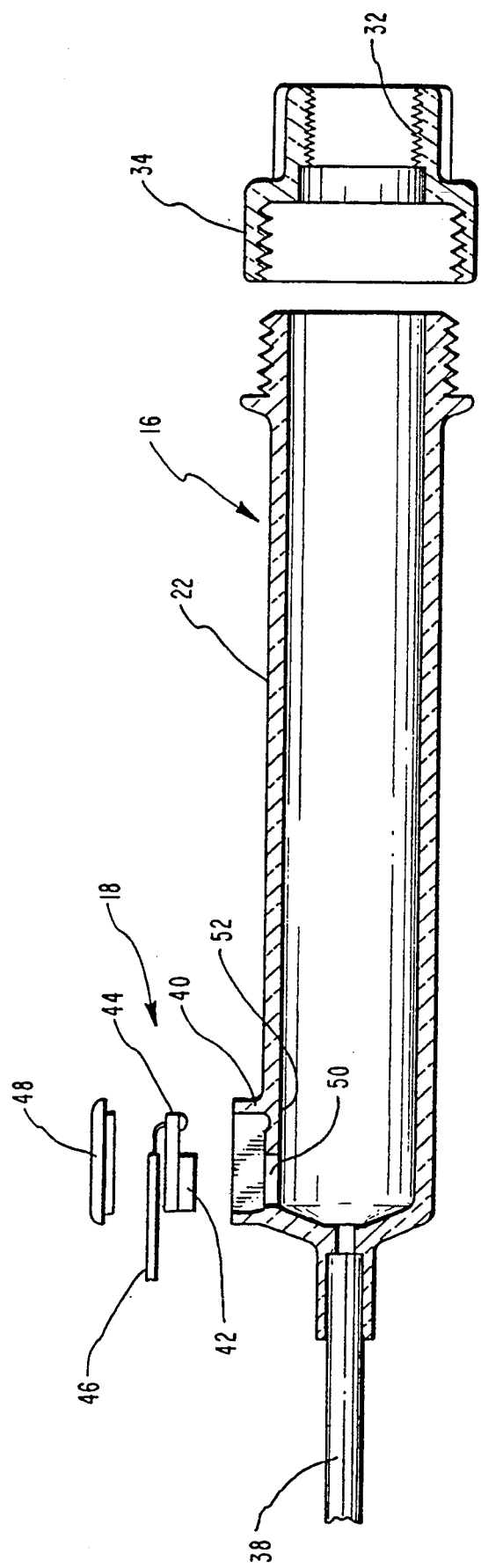
FIG. 3 is a partial cross-sectional view of the syringe barrel that more particularly illustrates one presently preferred structure and method for placing the transducer means in fluid communication with the interior of the syringe and the tubing which is connected to the balloon catheter.
Figure 4:
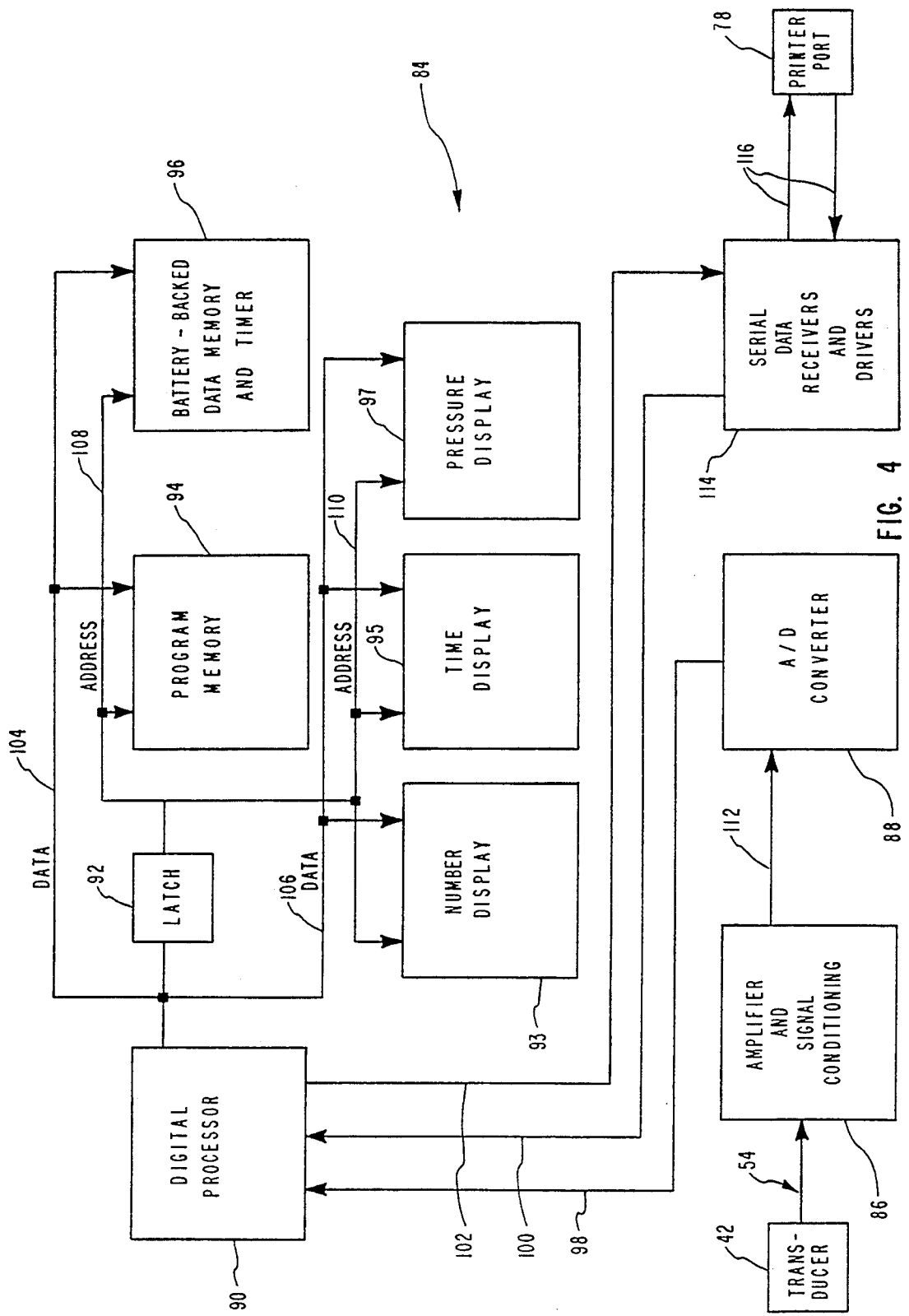
FIG. 4 is a functional block diagram which schematically illustrates the primary components of one presently preferred electronic circuit used in connection with the electronic controller.

In the preferred embodiment illustrated in FIG. 2, the overall system is generally designated at 14 and the syringe is generally designated at 16. With reference to FIGS. 2 and 3 taken together, the syringe 16 is comprised of a barrel 22 typically molded from transparent plastic material to permit inspection of the contents thereof. A syringe plunger 24 (FIG. 2) is slidably mounted within the barrel and is secured within the barrel 22 by means of a cap 34 which can be threaded onto or otherwise securely attached at the end of the barrel 22. The syringe plunger 24 has a threaded portion 30 which mates with corresponding threads 32 (see FIG. 3) of end cap 34.

The proximal end of plunger 24 is provided with a soft rubber bulb 25 which engages the interior of barrel 22 in a fluid-tight fit such that by sliding the syringe plunger 24 further into the barrel 22, positive pressure exerted on the fluid contained within syringe 16 and connecting tubing 38 will be applied to the balloon catheter which is connected to the tubing 38 by means of a rotatable luer connector 39. Similarly, by withdrawing the syringe plunger 24 toward the rear of the barrel 22, the positive pressure exerted on the balloon catheter will be released.

Rapid movement of the syringe plunger 24 is accommodated by means of a trigger mechanism comprising a spring-activated trigger 28 which can be retracted into handle 29 so as to disengage the threads 30 from the corresponding threads 32 of cap 34. This permits the plunger 24 to freely slide in either direction within the syringe barrel 22. By releasing the compression on trigger 28 relative to handle 29, the threads 30 are then permitted to engage the corresponding threads 32 of cap 34 so that thereafter the syringe plunger 24 can only be advanced or retracted by screwing the plunger 24 either clockwise or counter clockwise, respectively. Thus, rapid application or release of pressure applied to the balloon catheter can be accomplished by compressing the trigger 28 against handle 29 followed by movement of the syringe plunger 24 to the position desired for the approximate pressure to be applied. This can then be followed by release of the trigger 28 and screwing the plunger 24, which will permit a slow, gradual adjustment of the syringe plunger 24 to the exact pressure that is desired.

It will be appreciated that insofar as providing for application and release of positive inflation pressure, this function of syringe 16 of the system could be provided by any of a number of syringe systems which are conventional or known in the art. A more complete description of syringe 16 is contained in U.S. application Ser. Nos. 325,561 and 434,460 filed Mar. 17, 1989 and Nov. 13, 1989, now U.S. Pat. Nos. 5,057,078 and 5,047,615, respectively, which are incorporated herein by reference.

The transducer means of the system of the present invention is generally designated in FIGS. 2 and 3 at reference numeral 18. As shown best in FIG. 3, the body of syringe barrel 22 has a small housing 40 formed at the leading end of the barrel as an integral part of the syringe barrel 22. The housing 40 communicates through a small circular opening 50 formed in the sidewall of syringe barrel 22 with the interior of syringe barrel 22 for the purpose of providing fluid communication from the interior of barrel 22 and connecting tubing 38 to the transducer means, as hereinafter more fully described.

As used herein, the term "fluid communication" is intended to mean the pneumatic or hydraulic transmission (direct or indirect) of fluid pressures exerted within the syringe barrel 22 and/or connecting tubing 38 to the transducer means so that such fluid pressures can be sensed by the transducer means. Direct transmission of such fluid pressures would occur, for example, when a diaphragm of a piezoresistive semiconductor transducer is placed into contact (either pneumatically or hydraulically, or a combination of both) with a fluid contained in a closed system, as would be the case in the preferred embodiments illustrated and described herein. Indirect transmission could be said to occur, for example, where the transducer means is coupled to a diaphragm that in turn contacts the fluid contained in a closed system.

Figure 5A:
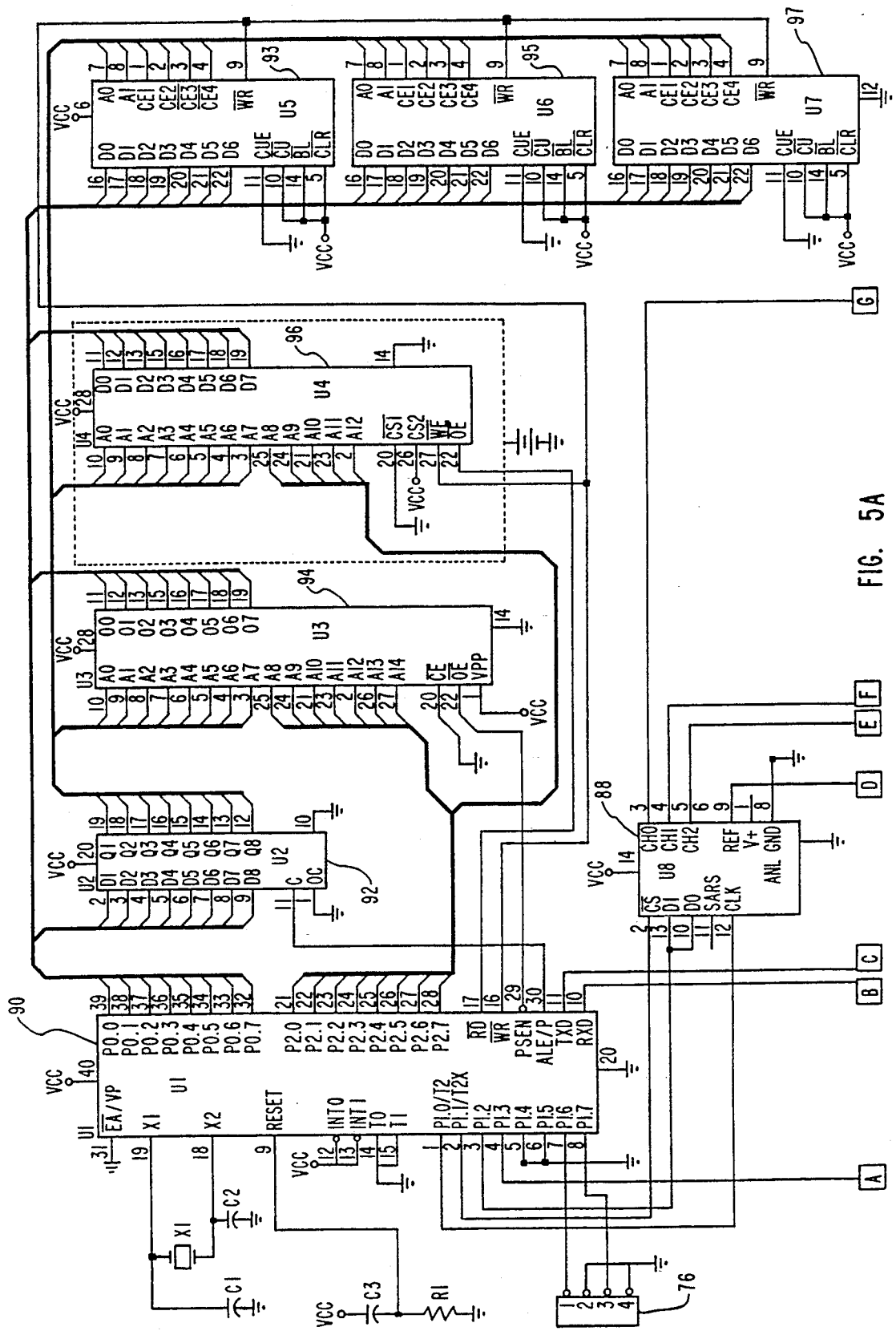
Figure 9A:
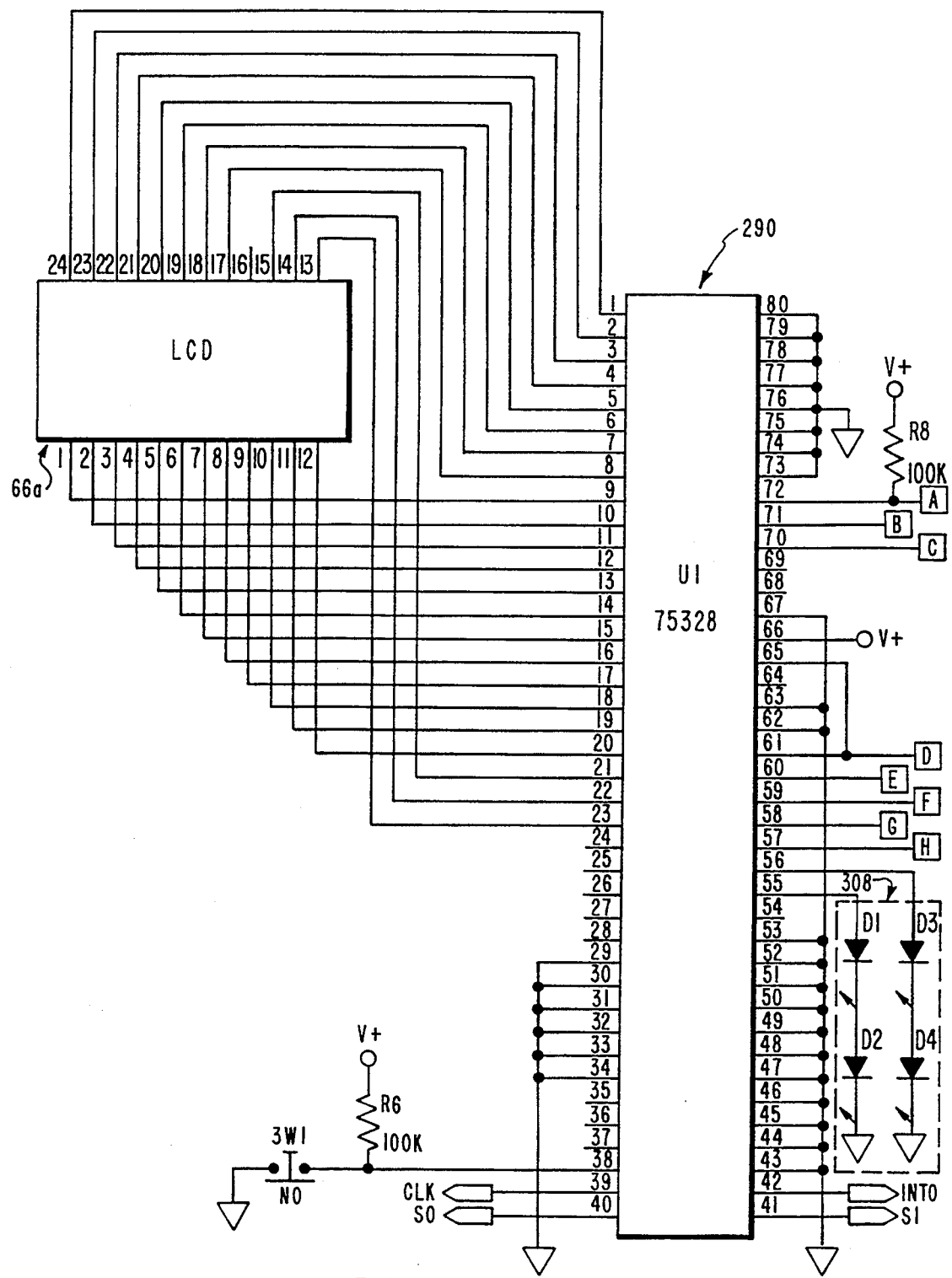
FIGS. 9A and 9B taken together constitute a detailed electrical schematic diagram which illustrate, as an example, the presently preferred embodiment and presently understood best mode for implementing the electronic circuit means of the syringe system of FIG. 7.
Figure 9B:
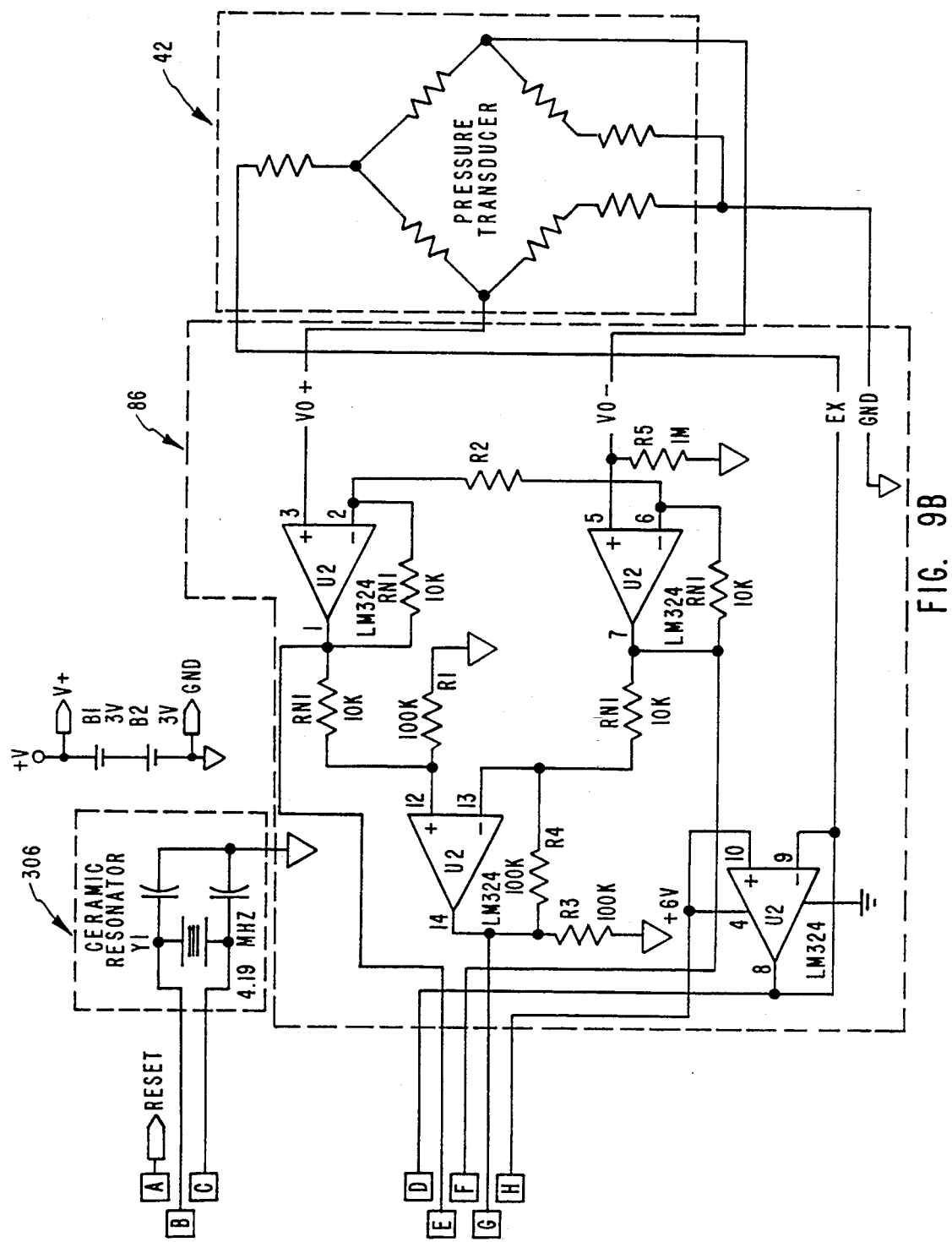

In FIG. 3, the transducer is shown as preferably comprising a piezoresistive semiconductor integrated circuit 42 which provides a Wheatstone bridge, as shown in the detailed electrical schematics at FIGS. 5B and 9B at the corresponding reference numeral. Transducer 42 is in turn attached to a small ceramic substrate 44 which contains additional circuitry for providing temperature compensation and calibration of the transducer 42, and to which is connected the electrical cable 46. The end of electrical cable 46, ceramic substrate 44 and piezoresistive semiconductor transducer 42 are assembled as illustrated in FIG. 3 and placed within housing 40, and then secured by a suitable potting compound and permanently enclosed by means of the cap 48 placed on top of the housing 40. In this manner, the entire transducer assembly is formed as an integral attachment to the syringe barrel 22. Stops 26 (see FIG. 2) are formed on the syringe plunger 24 so as to prevent the bulb 25 of syringe plunger 24 from being inserted to the point where it would otherwise close off the circular opening 50.

The small circular opening 50 may be filled, for example, with a silicone gel which will permit transmission of the fluid pressures exerted by means of syringe 16 through the circular opening 50 so that such pressures can be sensed by transducer 42, while at the same time isolating the integrated circuit 42 and substrate 44 from coming into contact with fluid contained in the syringe barrel 22.

In some prior art type inflation syringes, conventional analog or Bourdon-tube gauges are mounted to the syringe barrel. These types of analog or Bourdon-tube gauges typically include brass fittings which are in direct contact with the contrast media in the syringe. As a result, highly toxic substances, such as copper sulfate and heavy metal residuals, such as lead, have been found to be present in the contrast media as a result of chemical interaction of the brass fitting with the contrast media. While this is not harmful so long as the balloon is not ruptured, if a rupture does occur this toxic substance is released into the patient's cardiovascular system.

One advantage of the above-described syringe and transducer means is the elimination of materials, such as brass, from which such toxic substances are derived. Furthermore, contact of any sort between the contrast media and the transducer and related circuitry is completely prevented, as noted above, by the silicone gel that isolates such from the contrast media while still providing effective fluidic coupling to the transducer diaphragm.

While in the preferred embodiment the transducer means has been illustrated and described as a piezoresistive semiconductor which is integrally mounted to the syringe barrel 22, it should be appreciated that the preferred embodiment is illustrative only and is not to be construed as limiting the scope of the invention. For example, the semiconductor transducer could be located at the end of connecting tubing attached through a T-connector to tubing 38 and could therefore be located at a position remote from the syringe 16, as for example on an I.V. stand or mounted as part of the electronic circuitry contained inside of controller 20. Furthermore, the transducer means could also comprise transducer types other than the piezoresistive semiconductor type illustrated and described in the preferred embodiment, as for example conventional strain gauge transducers which have been known and used in the art for many kinds of different pressure monitoring applications, or fiberoptic transducers.

With continued reference to FIG. 2, the electronic circuit means and display means of the system of the present invention are illustrated in the preferred embodiment as comprising part of controller 20. The specific electronic circuitry which is used for implementing the controller 20, and its method of use for monitoring, displaying and recording PTCA data as illustrated in FIGS. 2-5 is set forth in U.S. Pat. No. 5,135,488 which is incorporated herein by reference, in its entirety.

2. FIGS. 7-9.

Figure 7:
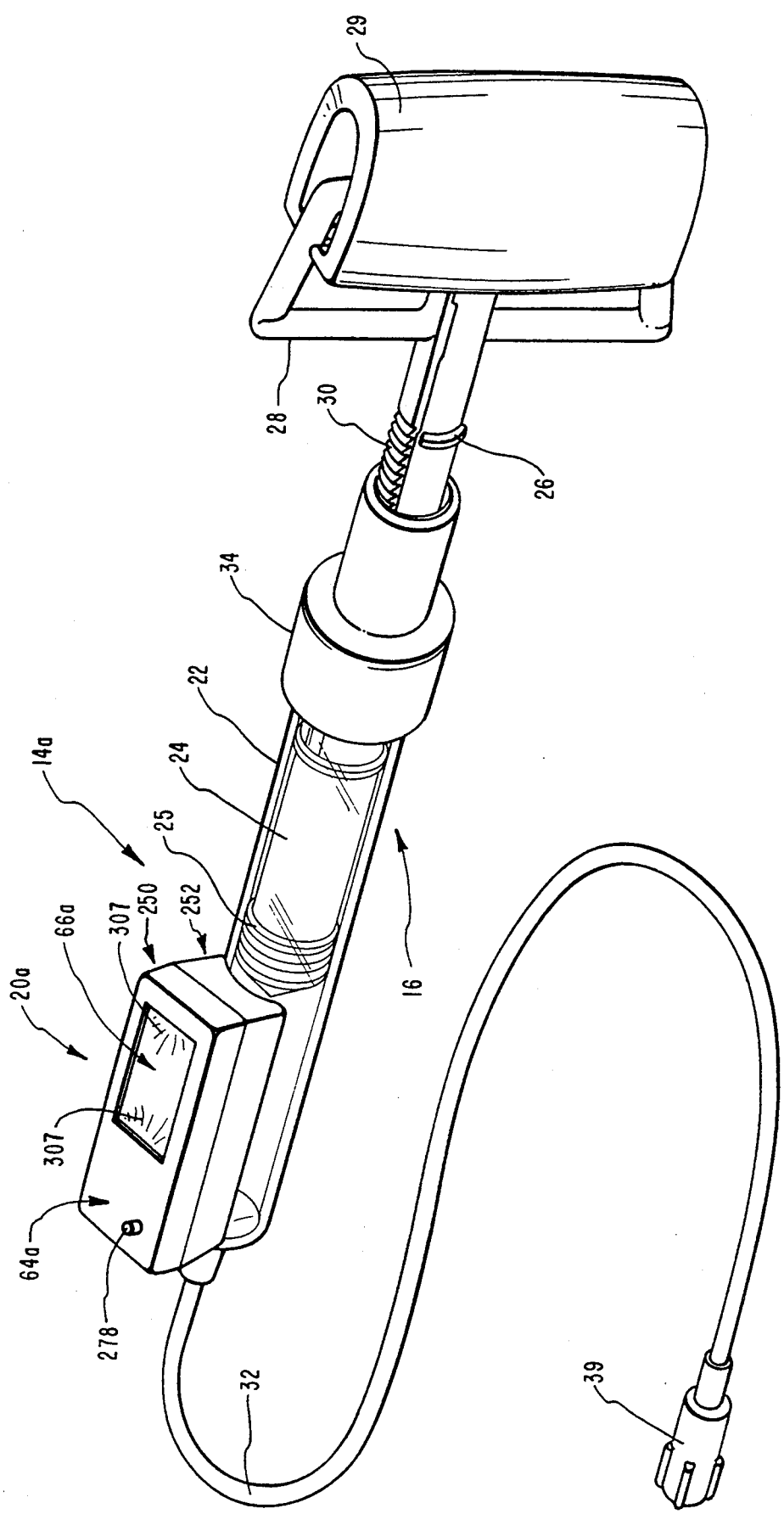
FIG. 7 is a perspective illustration showing a second embodiment of the system of the present invention in which a transducer means together with an electronic controller are all mounted directly onto the syringe barrel so as to form a totally self-contained, disposable syringe system.
Figure 8:
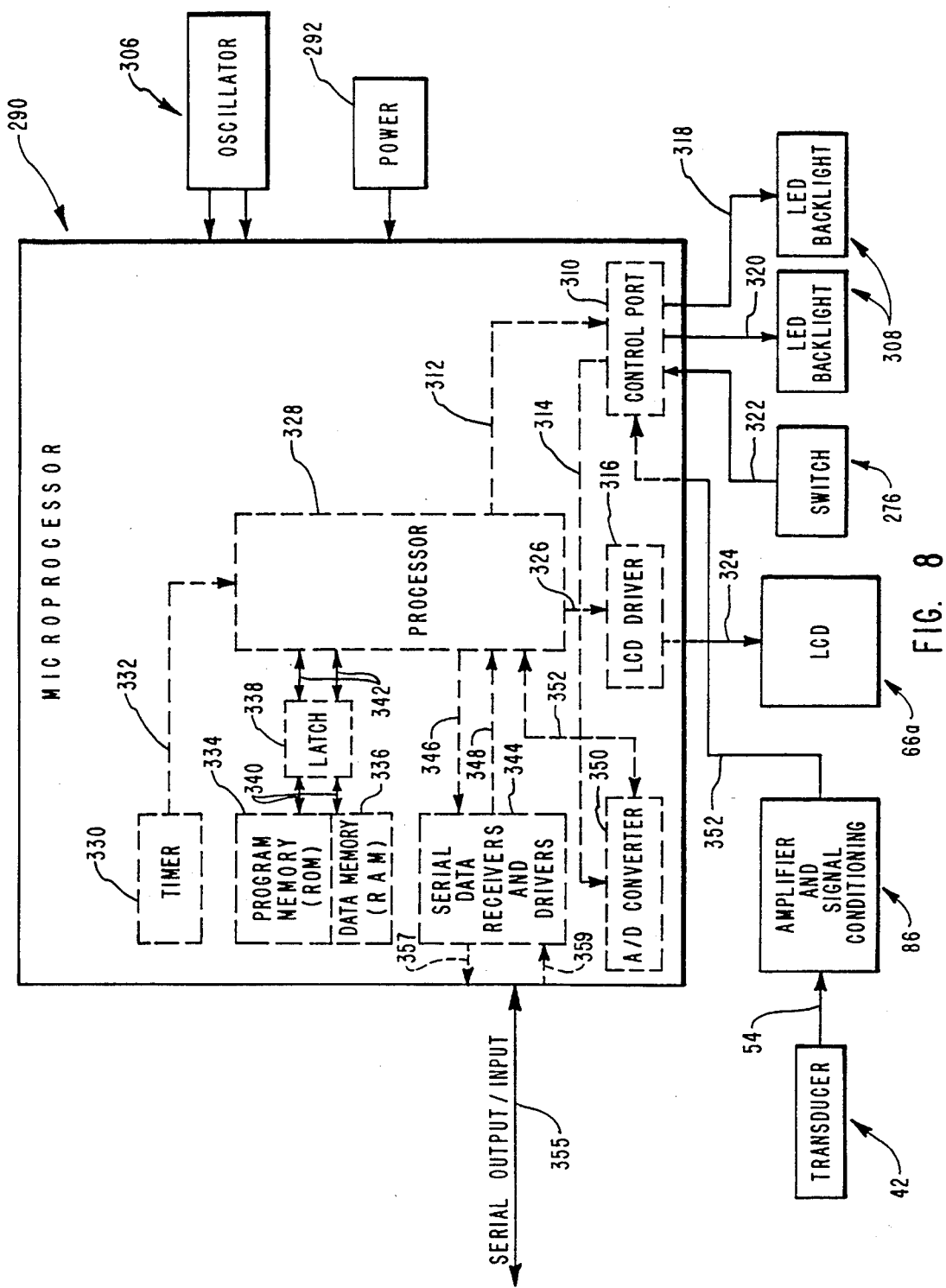
FIG. 8 is a functional block diagram which schematically illustrates the primary components of the digitally controlled electronic circuit used in connection with the syringe system of FIG. 7.

FIG. 7 illustrates an alternative embodiment of the syringe system of the present invention. In the embodiment of FIG. 7, the electronic circuit means and display means of the system of the present invention are designed so as to comprise part of a miniaturized controller which is generally designated at 20a that is battery powered and is mounted directly onto the syringe 16 so as to form a totally self-contained, disposable syringe system 14a. The specific electronic circuitry which is used for implementing the controller 20, and its method of use for monitoring, 12 displaying and recording PTCA data as illustrated in FIGS. 7-9 is set forth in U.S. Pat. No. 5,201,753, which is incorporated herein by reference, in its entirety.

b 3. FIGS. 11-17.

FIGS. 11-17 illustrate several embodiments of the syringe system of the present invention that utilize a detachable and reusable electronic circuit means which is operatively couplable to the syringe system. As will be described in further detail below, the syringe system 14b of FIGS. 11-17 comprises a syringe 16 that has a means for operatively coupling the detachable electronic circuit means to the syringe system. In one presently preferred embodiment, the means for operatively coupling the detachable electronic circuit means is comprised of a housing 400 mounted on the syringe barrel 22. The housing 400 is able to receive a detachable electronic circuit module 398.

The syringe system further comprises a transducer means for sensing the fluid pressure applied by the syringe, and for then generating an electrical pressure signal that is proportional the sensed fluid pressure. When attached to the housing 400, the detachable electronic circuit module 398 receives the electrical pressure signal and electronically process the signal, as will be described in further detail below. As will also be described, the syringe system 14b further comprises a display means for outputting a visual display of the magnitude of the sensed fluid pressure, and of the corresponding length of time the pressure is applied.

Thus, in the embodiments of FIGS. 11-17, the detachable electronic circuit module 398 can be detached from the disposable syringe 16 at the conclusion of a procedure, and can then be sterilized and attached to another syringe and system and re-used. In this manner, only the syringe 16 and tubing 38 of the syringe system is disposed of at the completion of a procedure, while the detachable electronic circuit module 398 of the syringe system can be re-used repeatedly. Consequently, the overall cost of an individual procedure is reduced considerably.

Several embodiments utilizing the detachable electronic circuit module 398 are described below in conjunction with the FIGS. 11-17. It should be noted that the syringe generally designated as 16 in FIGS. 11-17 is, except for housing 400, essentially identical in all respects to the syringe 16 described above in connection with FIGS. 2 and 3 and therefore will not be described in further detail here.

a. FIGS. 11 and 11A-11F.

FIGS. 11 and 11A-11F illustrate one presently preferred embodiment of the syringe system 14b utilizing the detachable electronic circuit module 398. The syringe system 14b comprises a syringe 16 (of which only the end of the syringe barrel 22 is shown) having the housing 400 mounted on the end of the barrel 22. As shown, the housing 400 has sides 404 that are integrally molded, or otherwise permanently attached, to form part of the syringe barrel 22. The housing 400 is rectangular in shape and conforms to the shape of the syringe barrel 22 and is further designed so as to receive the correspondingly shaped detachable electronic circuit module 398 in a tight fitting yet releasable manner.

Figure 11:
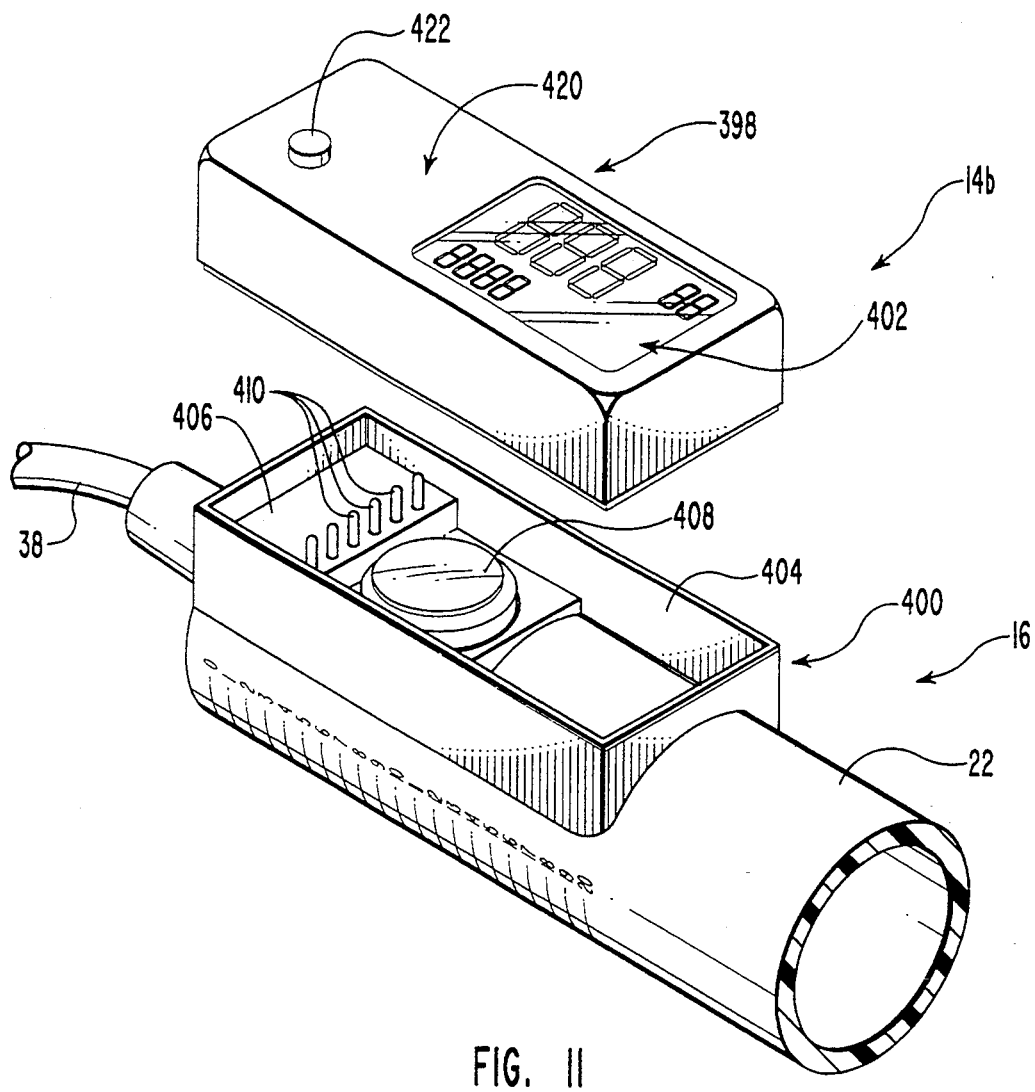
FIG. 11 is a perspective illustration showing yet another embodiment of the system of the present invention in which a reusable, detachable electronic circuit module is detachably mounted to a housing formed on the syringe barrel.

With continued reference to FIG. 11, a transducer housing 406 is also molded and attached to the syringe barrel 22 and is disposed within the housing 400. Located within the transducer housing 406 is the transducer means. As in the case of the embodiment described in FIGS. 2 and 3, the transducer means is comprised of an integrated circuit and is preferably a piezoresistive semiconductor transducer 42 (see FIG. 11B) that is mounted directly onto a ceramic substrate 44. In addition, a power means, as for example a battery 408, is mounted to the syringe barrel 22 within the housing 400. Battery 408 provides electrical power to the transducer 42 and to the circuitry contained on the detachable electronic circuit module 398 when the detachable electronic circuit module 398 is operatively coupled to the housing 400.

In the embodiment illustrated in FIG. 11, an electrical connection is established between the detachable module 398 and the transducer 42 when the module 398 is inserted into the housing 400. The electrical connection is accomplished via a conductive means that provides for a releasable electrical connection. The conductive means is comprised of, for example, a plurality of electrical prongs 410, mounted to the substrate 44 (see FIG. 11B) within transducer housing 406, together with a corresponding plurality of electrical pins 412, which are exposed on the bottom plate 414 of the detachable electronic circuit module 398 (illustrated in FIG. 11A). As is shown in the schematic diagram of FIG. 11E, three of the electrical prongs 410 provide a conductive path for the electrical pressure signal that is output by the transducer 42. Similarly, two of the electrical prongs 410 are connected to the battery 408 thereby providing a conductive path for electrical power. In an alternative embodiment, one additional electrical prong is connected to the serial output of a static memory device 565, as shown in FIG. 11F. In this embodiment, the static memory device 565, which will be described in further detail below, is also permanently mounted to the syringe barrel 12 on the substrate 44.

Figure 11A:
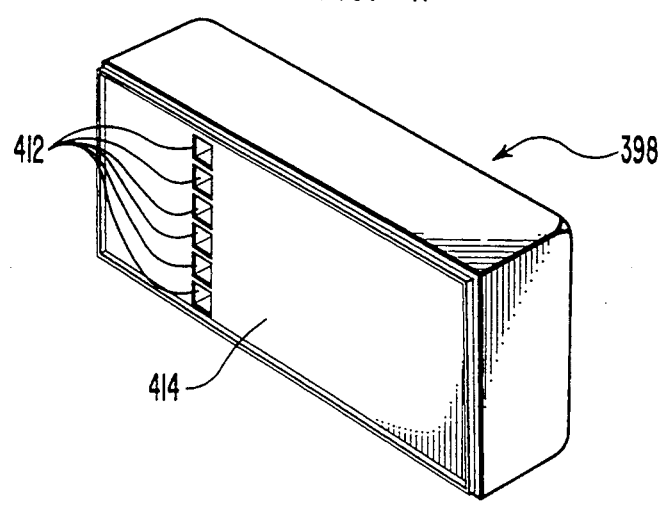
FIG. 11A illustrates in perspective the bottom portion of the detachable electronic circuit module of FIG. 11.

As is shown in FIG. 11A, the exposed base of each electrical pin 412 is a square-shaped conductive pad. The pins 412 extend upwardly from the bottom plate 414 of the detachable electronic circuit module 398 and are hermetically sealed so as to withstand various sterilization techniques and to prevent water, saline solution or other liquids from entering the interior of the detachable electronic circuit module 398. As is discussed in further detail below, the 65 electrical pins 412 are aligned, and electrically interconnected with, a corresponding electrical connector 428 (illustrated in FIG. 11C) having sockets 427 that receive the pins 412 in electrical connection. Connector 428 provides electrical connection with the printed circuit board 418.

Thus, when the detachable module 398 is received within the housing 400 and is thereby attached to the syringe barrel 22, the electrical prongs 410 are placed in electrical contact with the bottom of the correspondingly located electrical pins 412 and an electrical connection is established. Preferably, the electrical prongs 410 are spring actuated so as to be urged upwardly and thereby maintained in electrical contact with the bottom of the electrical pins 412.

Figure 12A:
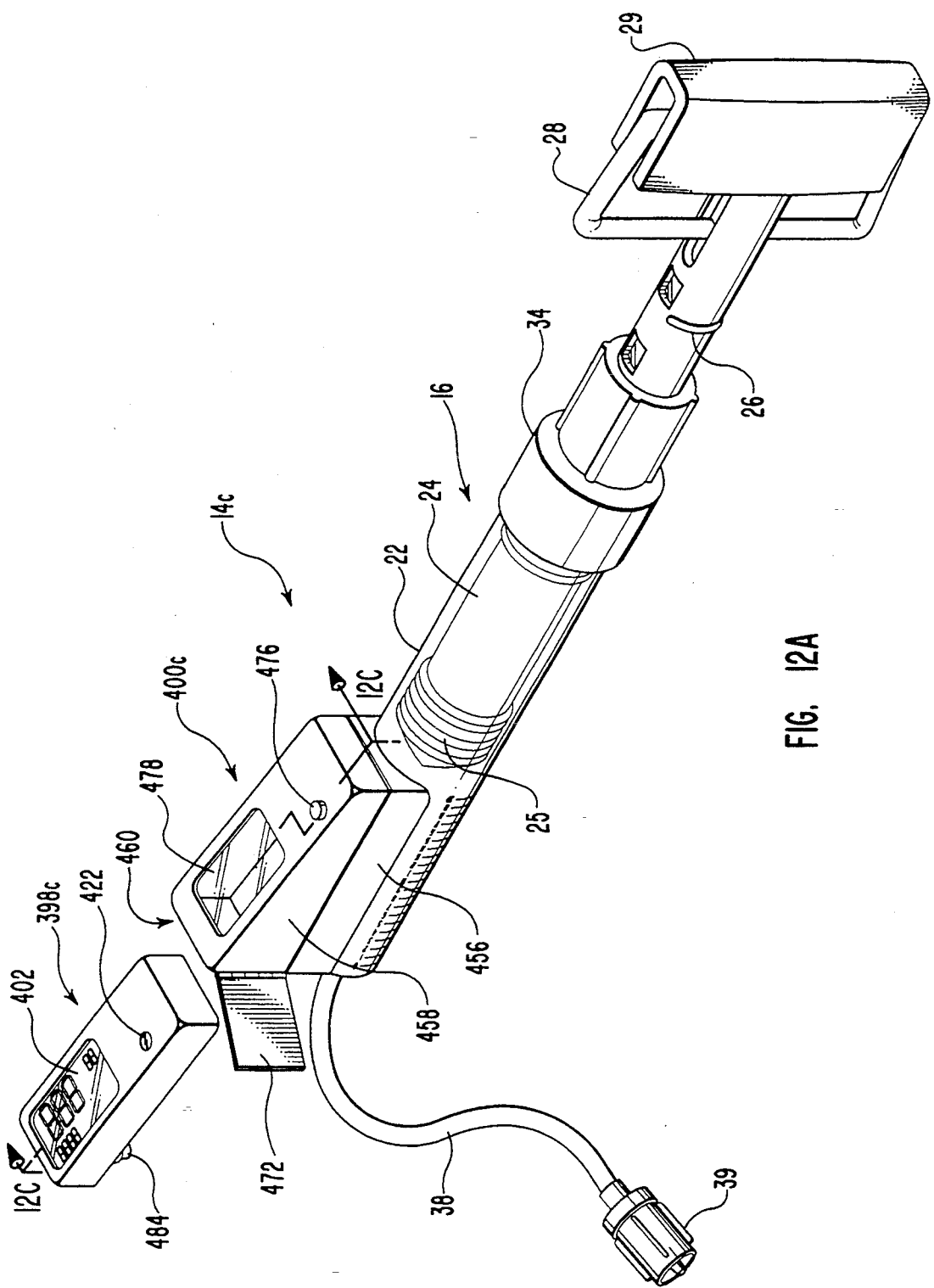
FIG. 12A is a perspective illustration showing a second embodiment of the detachable electronic circuit module and a housing disposed on the syringe barrel for receiving the detachable electronic circuit module.
Figure 12B:
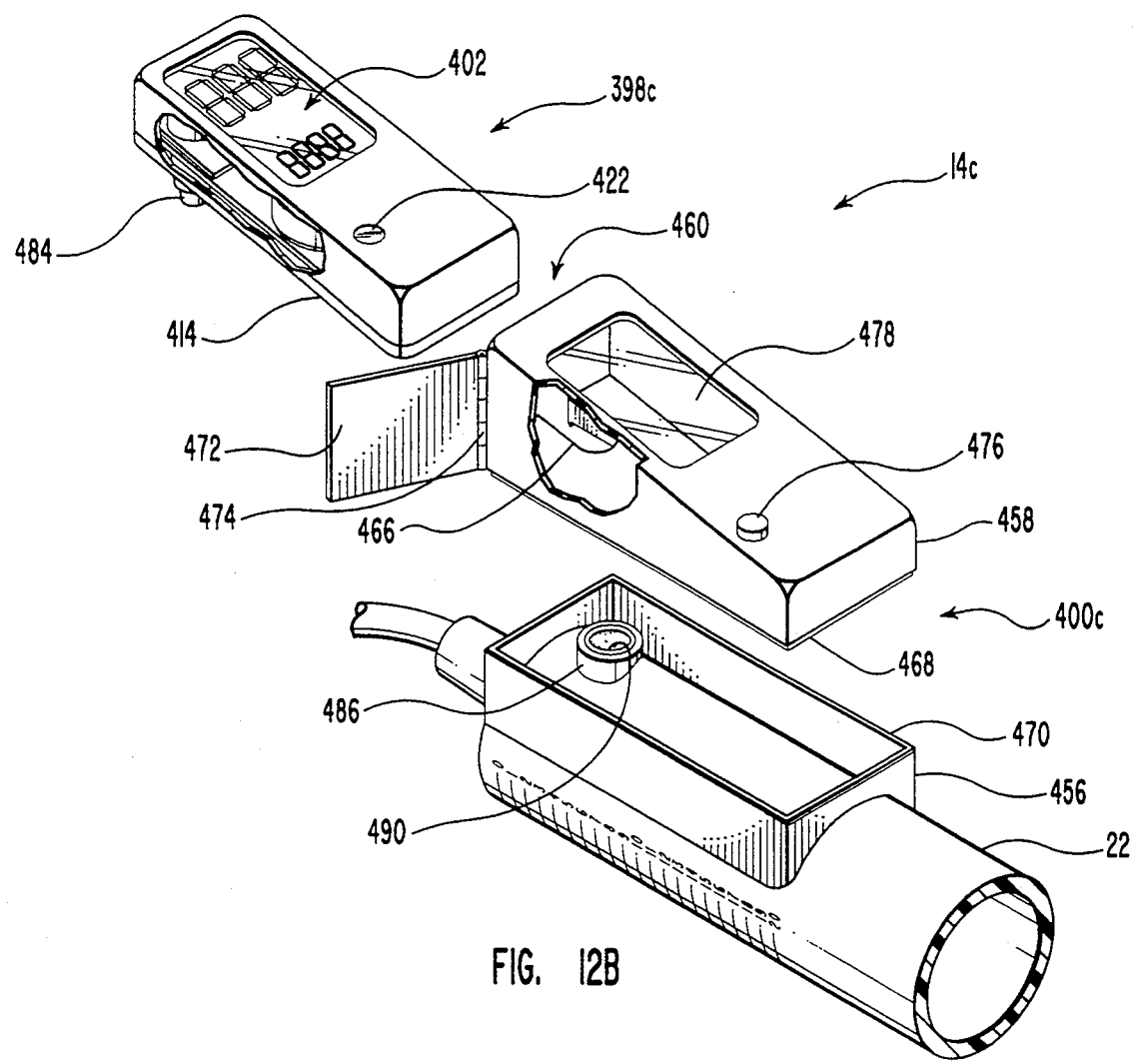
FIG. 12B is an exploded illustration which shows in greater detail the detachable electronic circuit module and housing of FIG. 12A.
Figure 12C:
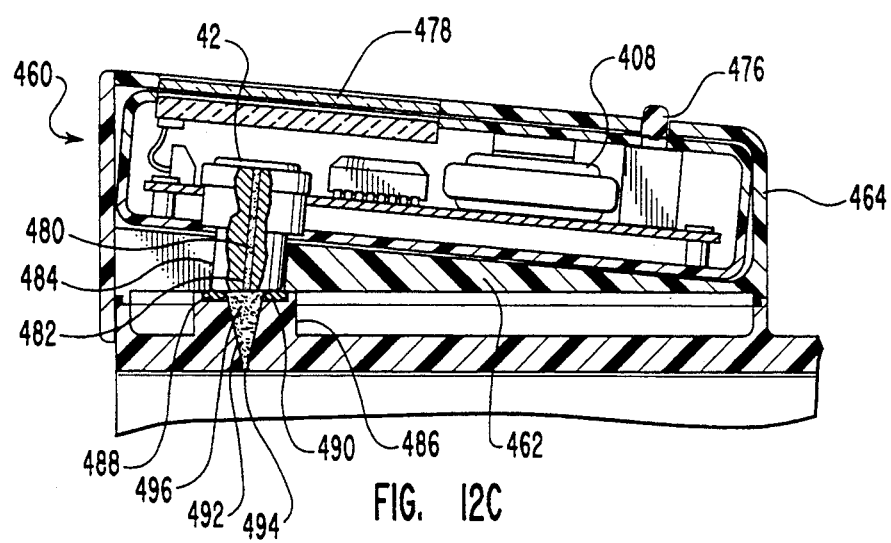
FIG. 12C is a partial, cross-sectional view of the detachable electronic circuit module and housing of FIGS. 12A and 12B with the detachable electronic circuit module disposed in the housing and operatively coupled in fluid communication with the inflation syringe system.

In the embodiment of FIG. 11 both the transducer 42 and the battery 408 are mounted to the syringe barrel 22. As will be appreciated however, the transducer 42 and/or the battery 408 could, in the alternative, be housed within the detachable module 398. As will be further appreciated, in the event that both the transducer 42 and the battery 408 are housed within the detachable module 398, there is no need for the prongs 410 or pins 412, since all connections are made directly on the printed circuit board 418, as illustrated in FIGS. 12A–12C, described in further detail below.

With further reference to FIG. 11, the detachable electronic circuit module 398 includes as an integral component the display means, as for example an LCD digital readout designated generally at 402. In addition, there is a control panel generally designated at 420, which is provided with a single button control switch 422. The button control switch 422, which will be more fully described, is used to turn the detachable electronic circuit module 398 on, and is also used to recall and display maximum inflation pressure and the duration of inflation for the last inflation event.

Referring now to FIG. 11B, the detachable module 398 is comprised of an upper housing portion 424 that is a generally rectangular shaped molded piece. The upper housing portion 424 further has a transparent window 426 formed in its upper surface through which the LCD digital readout 402 may be viewed. Also illustrated is the generally rectangular bottom plate 414, which is affixed to the upper housing portion 424 so as to completely seal and enclose the circuitry therewithin. Preferably, except for the window 426, the upper and bottom portions 424, 414 are molded from an opaque plastic material.

Importantly, the form of attachment between the upper and bottom portions 424, 414 must insure that a hermetic, fluid tight seal is formed, so as to prevent water, saline solution or other liquids from entering the interior of the detachable electronic circuit module 398, so as to permit sterilization and re-use.

Figure 11C:
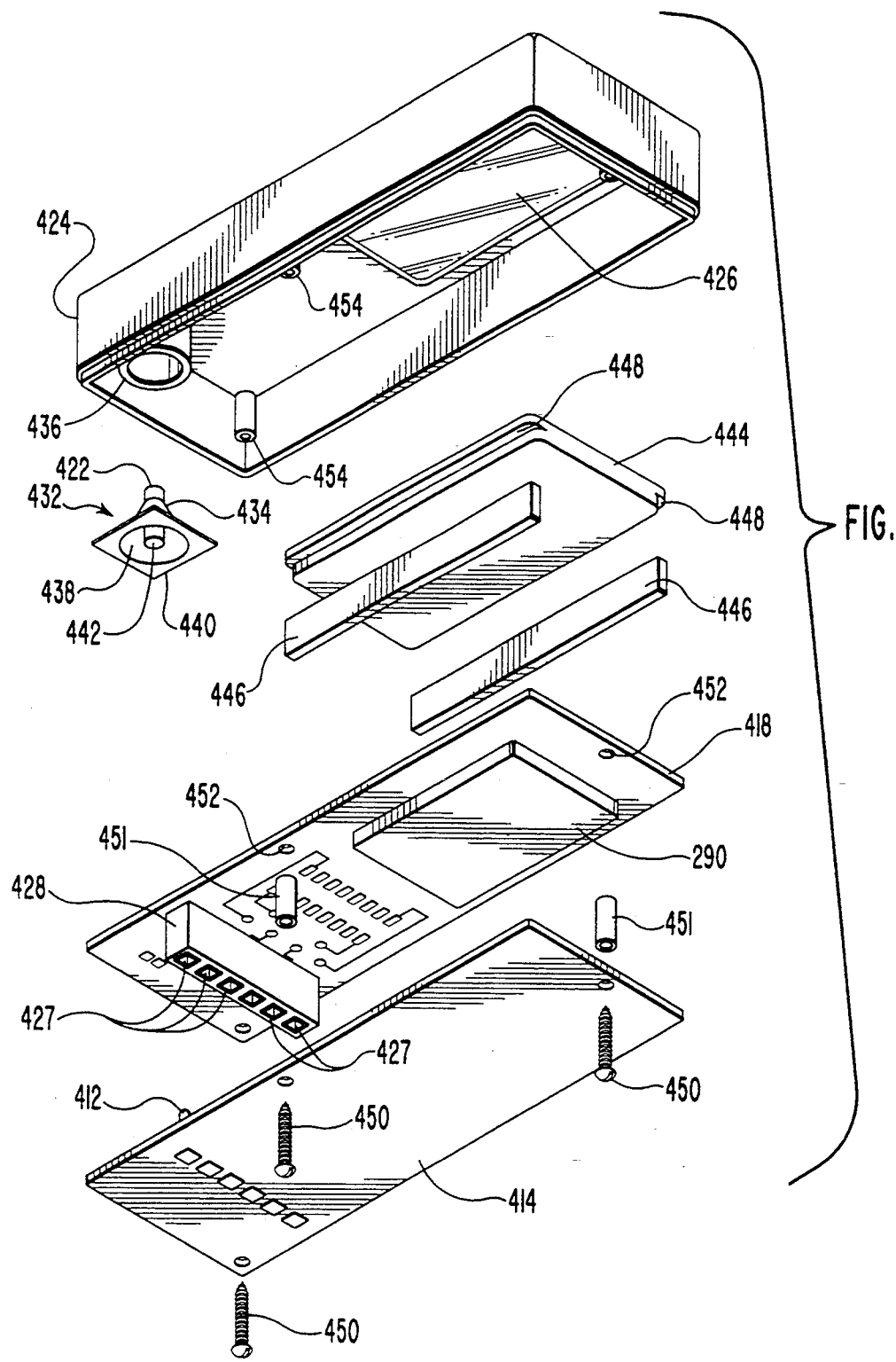
FIG. 11C is an exploded perspective illustration which shows in greater detail some of the primary components and assembly constituting the detachable electronic circuit module for the embodiment of the syringe system illustrated in FIG. 11.
Figure 11E:
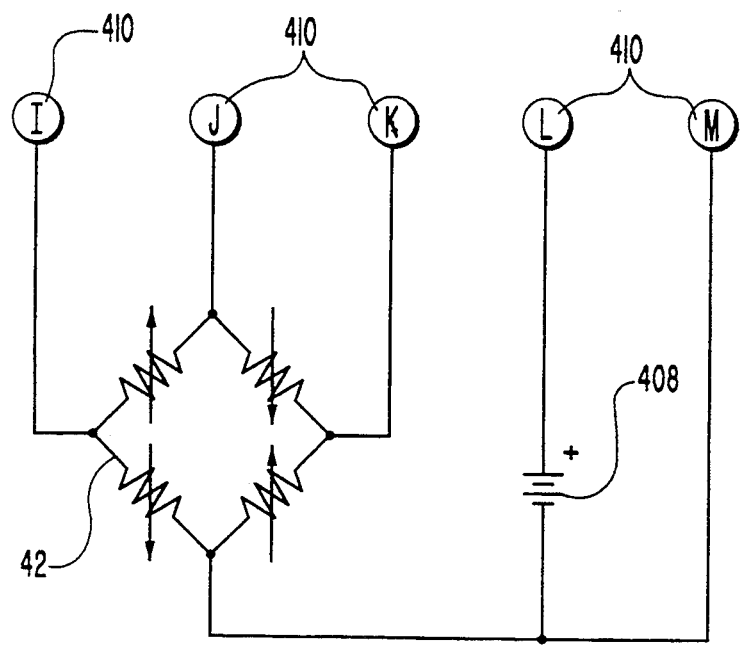
FIG. 11E is an electrical schematic diagram which illustrates, as an example, the manner in which the battery, the transducer and the electrical prongs are electrically interconnected.
Figure 11F:
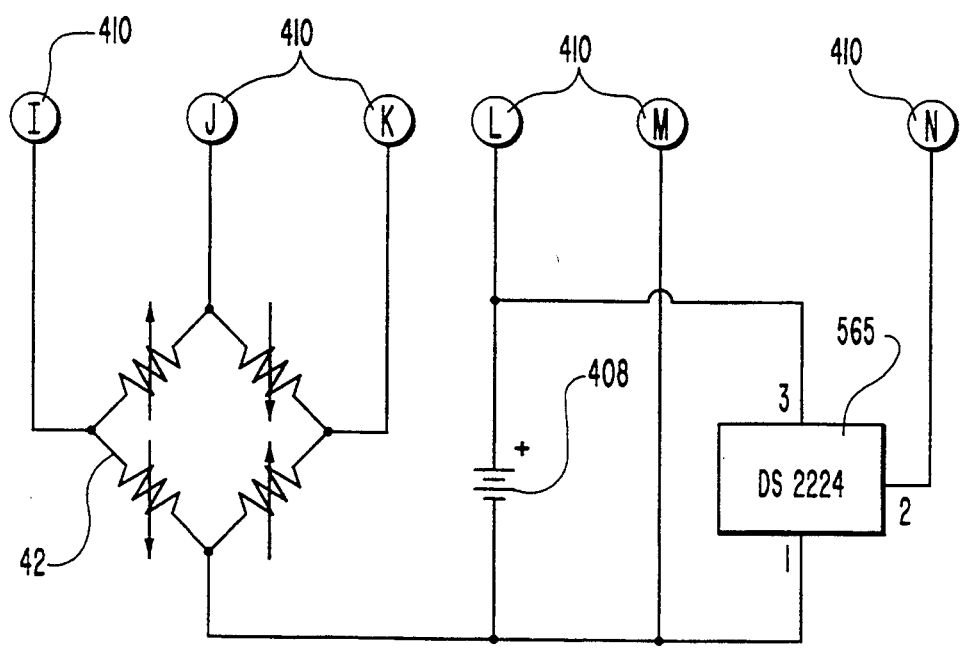
FIG. 11F is an electrical schematic diagram which illustrates an alternative embodiment of how the battery, the transducer, a memory device and the electrical prongs are electrically interconnected.

Disposed within the detachable module 398 is a printed circuit board 418 (shown in FIG. 11C). The printed circuit board 418 contains the microprocessor 290 and related circuitry that receives, monitors and processes the electrical pressure signal so as to generate, store, retrieve and/or display the PTCA inflation or deflation data.

FIG. 11C further illustrates the other components carried within the detachable module 398. As is shown, there is a resilient control switch generally designated at 432 which is comprised, for example, of an elastomeric button n button control switch 422. The control switch 432 has an upper cylindrical extension 434 that extends through an opening in well 436 which is formed in the upper housing portion 424 so that the button control switch 422 can be finger-actuated by pressing it. The control switch 432 also is comprised of an integral conically shaped skirt 438 which terminates in a generally square shaped base 440. This base 440 entirely covers the base of well 436 so that when the entire assembly is completed, the switch 432 is fluid tight and will thus not permit water, saline solution or other liquids to enter the detachable module 398 through the location of the button control switch 422, and is further able to withstand various sterilization techniques. Accordingly, the extension 434 extends downwardly and rests against the upper side of the printed circuit board 418 so that the button control switch 422 is held in a position which extends through the opening of well 436 into the position as shown in FIG. 11 and 11B but at the same time the base 440 also seals the well 430. When the control switch button 422 is pushed downwardly, the circular base 442 portion of the resilient control switch 432 is pushed into contact with a conductive pad (not shown) on the upper side of the printed circuit board 418 thereby making the necessary electrical contact to activate the electronic components, as hereinafter more fully described. The elastomeric properties of conical skirt 438 will return the button control switch 422 upwardly when it is released.

With continued reference to FIG. 11C, the microprocessor 290 is mounted to the underside of the printed circuit board 418. The upper side of printed circuit board 418 carries conductive pads (not shown) which are electrically connected to an LCD circuit 444 by means of conductive rubber Z strips 446 which also vertically support the LCD 444 so that it is held in engagement with the upper housing portion 424 of the detachable module 398 so as to be viewed through the transparent window opening 426. The LCD circuit 444 further includes channels 448 which are adapted to receive the upper edge of the conductive rubber Z strips so as to provide the electrical interconnection between the LCD 444 and the printed circuit board 418.

In the preferred assembly of the upper housing portion 424 of the detachable module 398, the elastomeric control switch 432 is placed into the well 436, the LCD circuit 444 is positioned over the transparent window opening 426, the elongated conductive rubber Z strips 446 are positioned at the side edges of LCD circuit 444 in the corresponding longitudinal channels 448, and then the printed circuit board 418 is placed over the top of all of those components. Pins or anchors 450 are then inserted through corresponding holes 452 in the printed circuit board 418 and bottom plate 414 and into corresponding spacers 451 and then into receiving holes 454 in the upper housing portion 424. The pins are bonded, threaded press fit or otherwise anchored into the holes 454.

The nature of the information displayed on the digital readout is best illustrated in FIG. 11D. The syringe system 14b is designed to digitally display the same information as in the embodiment of FIGS. 7-9 and specifically discussed in connection with FIG. 7C. Further, the information is displayed in accordance with the procedure set forth for the embodiment of FIGS. 7-9. The syringe system 14b is designed to digitally display the maximum inflation pressure, as illustrated at 296, as well as the duration of the inflation as illustrated at 298. Three annunciators are also designed to be displayed. Reference numeral 300 identifies a "LAST INFLATION" annunciator. This annunciator is displayed each time the button control switch 422 is pushed, at which time the maximum inflation pressure 296 and the inflation duration 298 are displayed in connection with the last inflation event.

This information is stored in a single register of microprocessor 290 and recalled when the button control switch 422 is pressed, if the system is at zero or negative pressure. For each inflation event (e.g., once pressure increases beyond about one-half atmosphere), the inflation pressure 296 and the duration of inflation 298 are displayed as real time parameters which will be continuously incremented during the inflation event while the inflation pressure is being increased. Once the user releases the inflation pressure so that the pressure drops to near zero, the inflation event is determined to be completed, and the maximum pressure and duration for that event can then be recalled and displayed by pressing button control switch 422.

Two additional annunciators as identified at reference numerals 302 and 304 are also designed to be selectively displayed. These annunciators identify, respectively, maximum and minimum pressure values which are programmed into the system. For example, typically minimum pressures which are programmed into the controller would be on the order of −0.4 atmospheres whereas maximum inflation pressures which would typically be programmed would be on the order of 20 to 25 atmospheres in the case of an angioplasty control system. These values could of course be varied depending upon the particular application for the syringe system.

The detailed description of the electronic circuitry contained in the functional block diagram of FIG. 8, and the accompanying electrical schematic diagrams of FIGS. 9A and 9B is the same, with the exception of two differences, as the circuitry contained within the detachable module 398. Although that detailed description will not be repeated here, the two primary differences will be addressed.

First, as noted in the discussion directed to FIG. 8, in the embodiment of FIGS. 7-9 the transducer 42 is electrically connected (as is schematically shown at 54 in FIG. 8) to the circuit components which serve as the amplifier and signal conditioning circuitry 86 by means of the conductive rubber Z strip 260 illustrated in FIG. 7A. In contrast, in the embodiment of FIG. 11, the transducer 42 is electrically connected to the circuit components which serve as the amplifier and signal conditioning circuitry 86 by the plurality of electrical prongs 410 and electrical pins 412, as previously described.

Figure 7B:
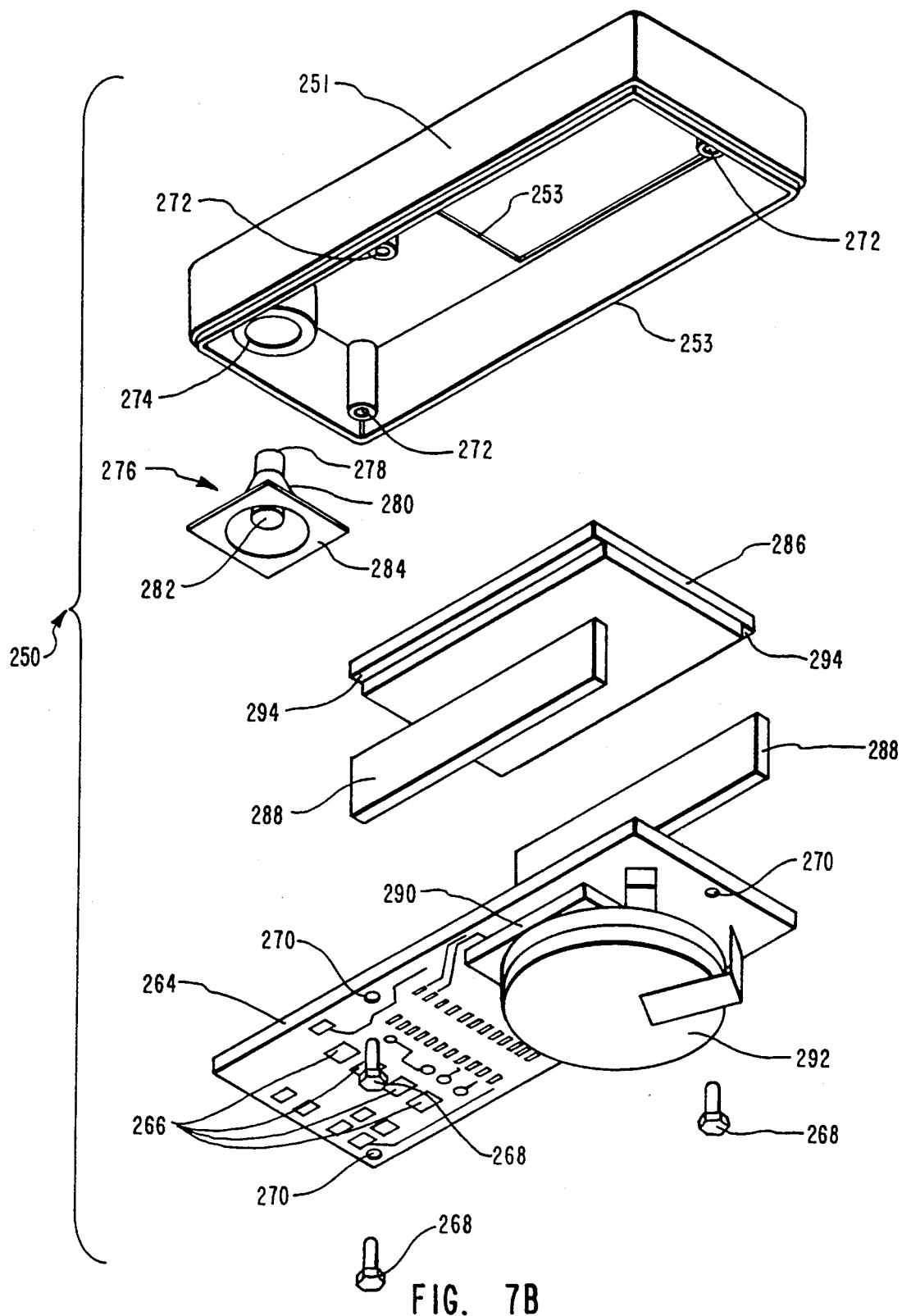
FIG. 7B is an exploded perspective illustration which shows in greater detail some of the primary components and assembly constituting the electronic controller for the embodiment of the syringe system illustrated in FIG. 7.

The second primary difference is with respect to the physical orientation of the battery 408. As noted in the discussion with respect to the embodiment of FIGS. 7-9, a battery 292 (shown in FIG. 7B) is mounted to the underside of the microprocessor 290. In contrast, in the preferred embodiment of FIG. 11, the battery 408 is disposed directly on the syringe barrel 22. Note however, that as discussed, the battery 408 could optionally be mounted within the detachable module 398, in which case the battery 408 may be physically oriented in a manner similar to that illustrated in FIG. 7B.

In all other respects, the description directed to the electronic circuitry set forth in the functional block diagram of FIG. 8, and the accompanying electrical schematic diagrams of FIGS. 9A and 9B applies to the circuitry contained within the detachable module 398. Further, the appropriate pin connections and the identification of each corresponding integrated circuit component illustrated in the schematic diagram of FIGS. 9A and 9B and taken in conjunction with the part number identification information set forth in Table II at the end of the description also applies to embodiment of FIGS. 11 and 11A-11D.

b. FIGS. 12A-12C.

Another presently preferred embodiment of a syringe system utilizing a detachable electronic circuit means is shown in FIGS. 12A-12C. In the embodiment illustrated in FIG. 12A, the syringe system, generally designated at 14c, comprises a syringe 16 having a means for operatively coupling the detachable electronic circuit module 398c to the syringe 16, as for example a housing, generally designated as 400c, mounted on the end of the syringe barrel 22. As shown, the detachable electronic circuit module 398c can be operatively coupled to the syringe 16 by placing it within the housing 400c. When received by the housing 400c, the detachable electronic circuit module 398c is held in a tight fitting yet releasable manner and, further, is fully encapsulated. When so enclosed, the detachable electronic circuit module 398c is held in a sealed, airtight and sterile manner. In this embodiment, the detachable module 398c does not have to be sterilized prior to re-use. Rather, a non-sterile detachable module 398c can be placed and sealed within the housing 400c of a sterilized syringe 16 and the sterile syringe system 14c is thereafter ready for use.

As better shown in FIG. 12B, the housing 400c is comprised of a lower housing assembly 456 and an upper housing assembly 458. The lower housing assembly 456 is a rectangular member wherein the top is open. The lower housing assembly 456 is firmly bonded and mounted to the syringe barrel 22, or may optionally be formed as an integral part of the syringe barrel 22.

With continued reference to FIG. 12B, the upper housing assembly 458 is fashioned as a generally rectangular member with one end having an entrance 460. Preferably, the walls of the upper housing assembly 458 are of a generally uniform thickness, except for the bottom wall 462 (see FIG. 12C). The bottom wall 462 has a greater thickness at the entrance end 460 which then tapers to the opposite end 464. As further illustrated in FIG. 12B, the bottom wall 462 also has a U-shaped notch 466 formed therein at the entrance end of the upper housing assembly 458. The U-shaped notch 466 is formed to receive a sensing port 486 on syringe barrel 22, and thus permits the detachable electronic circuit module 398c to be inserted into the housing 400c such that the transducer 42 (see FIG. 12C) can be placed in fluid communication with the fluid pressures exerted within the syringe barrel 22, as will be more fully described below.

With continued reference to FIGS. 12B and 12C, the bottom periphery 468 of the upper housing assembly 458 is notched and corresponds in size and in shape to the top periphery 470 (also notched) formed by the open top of the lower housing assembly 456. The two housing assemblies 456, 458 are thus firmly bonded together at the corresponding peripheries 468, 470 to form an enclosure capable of receiving the detachable electronic circuit module 398c through the entrance end 460 (as is shown in FIG. 12A).

In the embodiment of FIGS. 12A–12C, the housing 400c further comprises a hinged door, for selectively opening and closing the entrance end 460 of the housing 400c. FIGS. 12A and 12B illustrate how a door 472 is attached via a hinge assembly 474 to the entrance end 460 of the upper housing assembly 458 of the housing 400c. The door 472 is illustrated as being in its opened position so that the detachable electronic circuit module 398c may be inserted through the entrance end 460 and into the housing 400c. When closed, the door 472 will seal the entrance end 460 of the housing 400c in a manner such that the housing 400c encloses the detachable module 398c in an airtight and sterile manner. At the conclusion of the procedure, the door 472 may be opened, the detachable module 398c retrieved for further use, and the syringe 16 discarded.

With continued reference to FIG. 12B, the housing 400c further includes an access switch 476. The access switch 476 is formed through the top of the upper housing assembly 458 and is positioned so as to be aligned with the button control switch 422 located on the detachable electronic circuit module 398c. Preferably, the access switch 476 has elastomeric properties such that when it is depressed by a user, the access switch 476 extends downwardly so as to depress the button control switch 422. The access switch 476 will then retract once pressure is released and thus disengage the button control switch 422. The access switch 476 thereby allows the user to manipulate the button control switch 422 when the detachable electronic circuit module 398c is disposed within the housing 400c.

FIGS. 12A and 12B further illustrate how the upper assembly portion 458 of the housing is formed with a transparent viewing portion 478. The viewing portion 478 allows for the user to view the display 402, when it is disposed within the housing 400c.

In the embodiment of FIGS. 12A–12C, the transducer 42 and the battery 408 (see FIG. 12C) are both contained as part of the detachable electronic circuit module 398c, rather than being placed on the syringe 16, as is the case with the embodiment illustrated in FIG. 11 and discussed above. Consequently, there is no need for a conductive means for establishing an electrical connection between the syringe and the detachable electronic module 398c, since it is all self-contained. There is, however, a mechanical fluid interface between the fluid pressure generated within the syringe barrel 22 and the transducer 42 contained in on the detachable electronic circuit module 398c.

With continued reference to FIG. 12C, pressure generated by the syringe 16 is transmitted to the diaphragm of the transducer 42 via a fluid pressure transmitting medium, as for example a silicone gel column 480. The gel column 480 is disposed entirely within an elongated cylindrical bore 482 that is formed through the cylindrically shaped transducer port 484. The transducer port 484 extends downwardly from the bottom plate 414 of the detachable electronic circuit module 398c.

Referring now to FIGS. 12B and 12C together, a pressure sensing port 486 is formed on the syringe barrel 22 within the housing 400c. The exterior of the sensing port 486 is cylindrical in shape, and as can be seen in FIG. 12C, the interior has a first and a second recess formed therein. The first interior recess 488 is located at the top end of the sensing port 486 and contains an elastomeric sealing member 490. This first recess 488, together with the elastomeric member 490, forms a cylindrical diameter that is capable of receiving in a tight fitting manner the outside diameter of the transducer port 484. The second recessed portion of the sensing port 486 is a conically shaped bore 492. The upper diameter of the conically shaped bore 492 is greater than the diameter of cylindrical bore 482 that contains the gel column 480 to ensure a fluid coupling between gel contained in the bore 484 and gel contained in the conical bore 492. The conically shaped bore 492 extends through the wall of the syringe barrel thereby forming a small circular opening 494. Disposed entirely within the conically shaped bore 492 is a second fluid pressure transmitting medium, as for example silicone gel 496. Thus, fluid pressures exerted by means of the syringe 16 will be transmitted through the silicone gel 496 and 480 to transducer 42. In all other respects, the detachable electronic circuit module 398c of FIG. 12 is essentially identical in its structure and operation, and in the PTCA inflation or deflation data displayed, to the detachable electronic circuit module 398 described above in connection with FIGS. 11 and 11A–11D.

In operation, the detachable electronic circuit module 398c will be placed and sealed within the housing 400c. In so doing, the gel column 484 will be operatively coupled to gel 496 contained in the pressure sensing port 486, as is illustrated in FIG. 12C. Thus, pressures exerted within the syringe barrel 22 will be transmitted through the gel 480, 496, to the transducer 42. In this manner, the transducer 42 is able to sense the pressure exerted and output the corresponding electrical pressure signal, which can then be processed by the circuitry contained in the detachable electronic circuit module 398c, as discussed in conjunction with FIG. 11 above.

c. FIGS. 13–17

Figure 13:
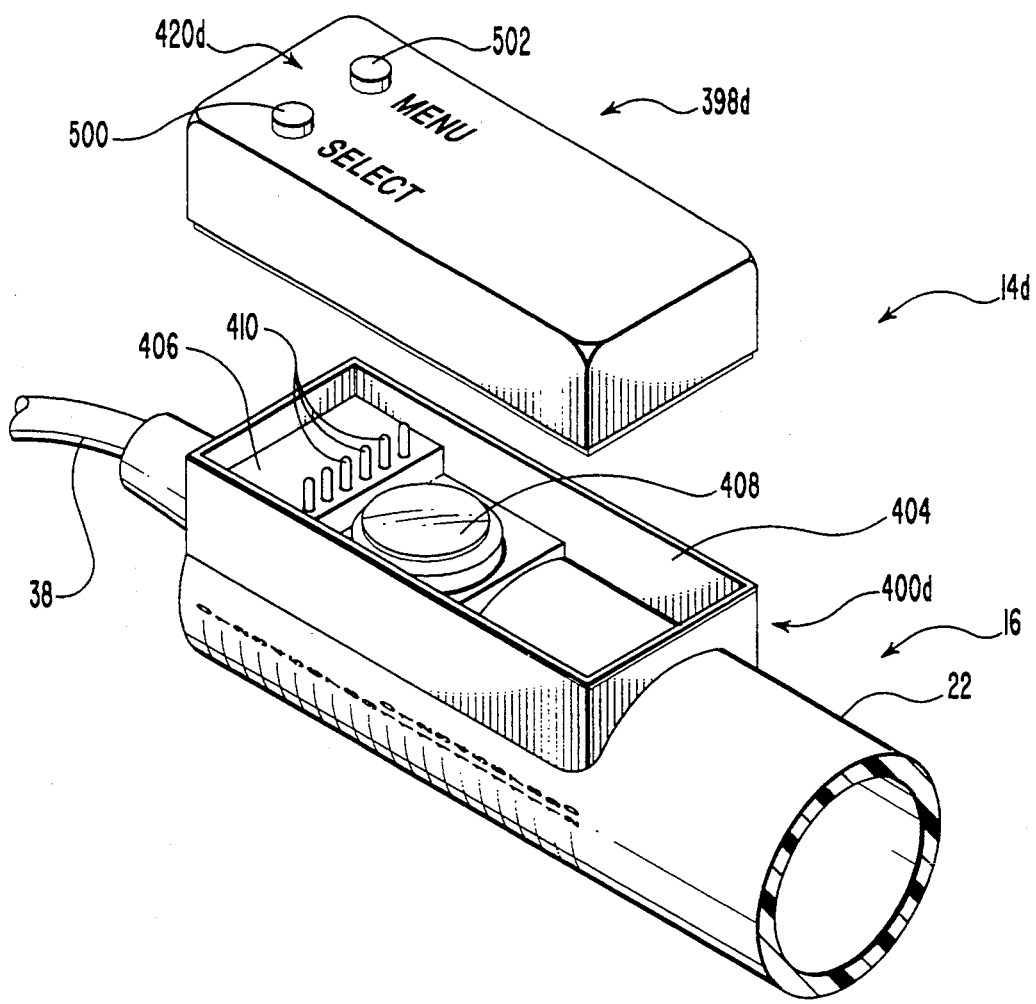
FIG. 13 is a perspective illustration showing still another embodiment of the detachable electronic circuit module.

FIG. 13 illustrates yet another embodiment of a syringe system 14d utilizing a detachable electronic circuit means. The syringe system is comprised of a syringe 16 (partially shown), a transducer 42, a detachable electronic circuit module 398d, and means for operatively coupling the detachable module 398d to the syringe 16, as for example a housing, generally designated as 400d, mounted on the end of syringe barrel 22. Syringe system 14d further includes a remote console means, such as a remote console 498 having an integral graphic display 402 (shown in FIG. 15).

When the detachable electronic circuit module 398d is operatively coupled to the syringe via the housing 400d, the transducer 42 senses the applied fluid pressure and outputs the electrical pressure signal, which is received by the detachable module 398d via the conductive means as described above. As will be described in further detail below, circuitry contained within the detachable electronic circuit module 398d then processes the pressure signal and wirelessly transmits it and related information as transmission data to the remotely located remote console 498 (shown in FIG. 15). Circuitry contained within the remote console 498 then further processes the transmission data transmitted by the detachable module 398d and then displays the corresponding inflation or deflation data on the graphic display 402.

With further reference to FIG. 13, the transducer 42, the battery 408, the housing 400d and the manner of electrically interconnecting the detachable electronic circuit module 398d with the syringe 16 via a conductive means are each substantially the same as was set forth above in conjunction with FIGS. 11 and 11A. That discussion will not be repeated here.

Disposed on the upper portion of the detachable electronic circuit module 398d is a control panel, generally designated at 420d. The control panel 420d is provided with a select switch 500 and a menu switch 502. Disposed within the detachable electronic circuit module 398d is a printed circuit board similar to that shown in FIG. 11C and described above. The printed circuit board contains the microprocessor 290 and related circuitry (shown in FIG. 16 and described in detail below) that receives, monitors, processes, and then wirelessly transmits the electrical pressure signal as transmission data to the remote console 498. Further disposed within the detachable electronic circuit module 398d are two resilient control switches (not shown) that interface with select and menu switches 500, 502 disposed on the control panel 420. The resilient control switches are similar in all respects to the resilient control switch 432 described in FIG. 11C above.

Figure 16:
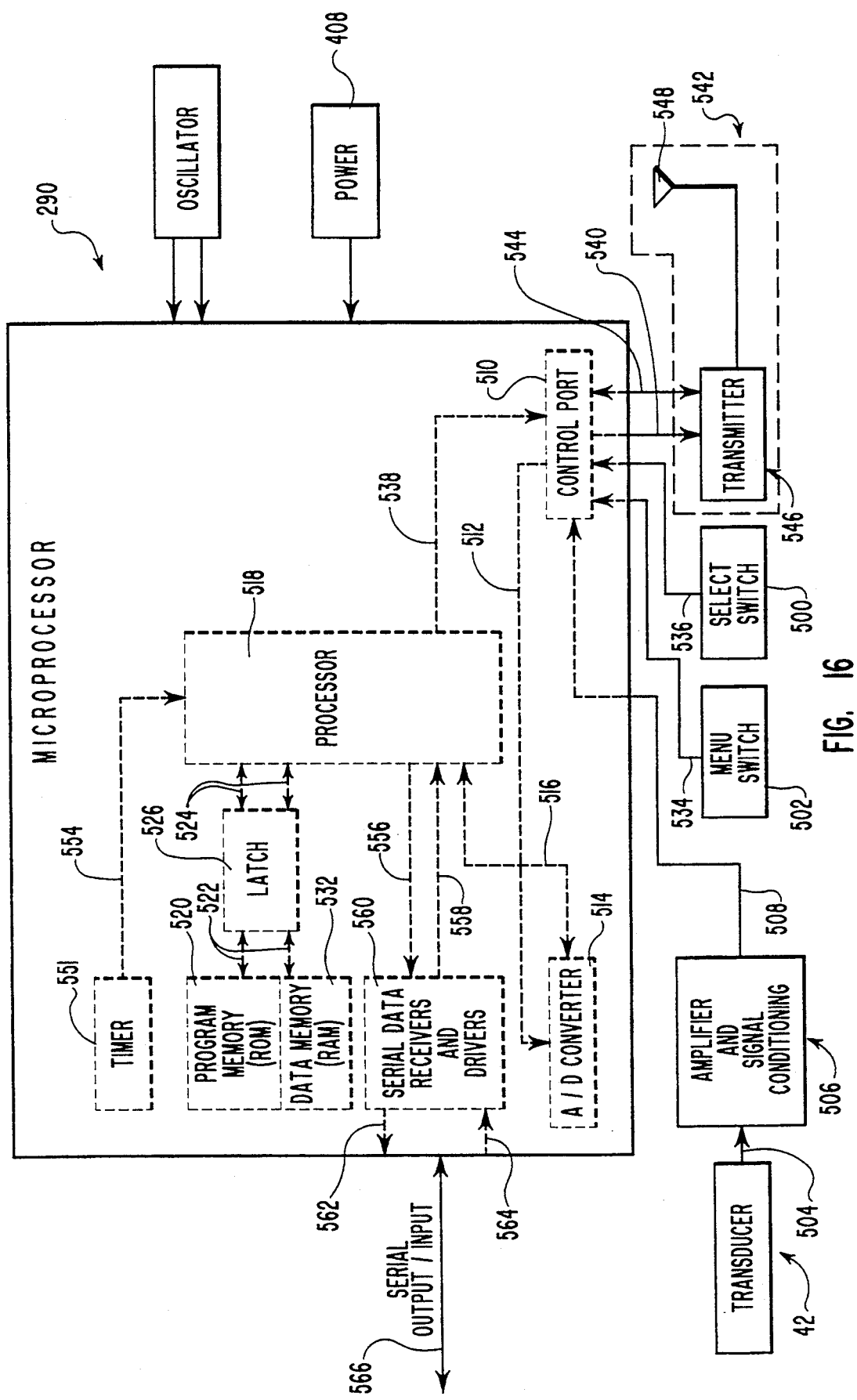
FIG. 16 is a functional block diagram which schematically illustrates the primary electrical components of one presently preferred embodiment of the detachable electronic circuit module shown in FIG. 13.

The electronic circuitry contained within the detachable electronic circuit module 398d is illustrated in further detail in the functional block diagram of FIG. 16. The detachable electronic circuit module 398d comprises, by way of example, means for amplifying and conditioning the electrical pressure signal output by the transducer means; means for converting the amplified signal from an analog to a digital form; digital processor means for processing the digital form of the electrical pressure signal so as to derive therefrom transmission data which represents inflation or deflation data; data memory means for storing the transmission data derived by the digital processor means; program memory means for storing machine-readable instructions utilized by the digital processor means to derive and store the transmission data; and transmission means for converting the digital transmission data into a transmission signal and for wirelessly transmitting the transmission data to the remote console 402 via the transmission signal.

With continued reference to FIG. 16, the transducer 42 is essentially the same as the transducer described in connection with the previous embodiments. An electrical connection is established between the detachable module 398d and the transducer 42 when the module 398d is inserted and detachably coupled into the housing 400d. The electrical connection is accomplished via a conductive means. The conductive means provides for a releasable electrical connection and is preferably comprised of a plurality of electrical prongs (shown in FIG. 13), together with a corresponding plurality of electrical pins (not shown) which are exposed on the bottom of the detachable electronic circuit module 398d. Thus, conductive means in this embodiment is the same as the conductive means described above in connection with the embodiment of FIGS. 11 and 11A. In this manner, transducer 42 is electrically connected, as is schematically shown at line 504, to the amplification and signal conditioning circuitry, generally designated at 506. A presently preferred embodiment of the amplifier and signal conditioning circuit 506 is identical to the corresponding circuit components designated at 86 in FIG. 9B and described above in connection with the embodiment of FIGS. 7-9.

From the amplifier and signal conditioning circuit 506 the amplified analog signal is then input, as is schematically represented at line 508 to a control port 510 which is internal to the microprocessor's 290 integrated circuitry. From control port 510, the signal is input as schematically indicated at line 512 to an analog to digital (A/D) convertor 514 which is also internal to the microprocessor's 290 integrated circuitry. The A/D convertor 514 serves as a means for converting the amplified electrical pressure signal from the analog to a digital form.

The particular integrated circuit which is used for microprocessor 290 is the same as the microprocessor identified in FIG. 9A as integrated circuit U1 and which is also identified in Table II at the end of the detailed description. It should be appreciated that any particular circuit component and circuit design that are referred to are intended merely as an example of the presently preferred embodiment and the presently understood best mode of implementing the overall functions which are represented by the block diagram of FIG. 16. Of course other circuit designs could be devised that would work satisfactorily, using either software-based digital processing circuitry or hardware-based circuit designs.

With continued reference to FIG. 16, the digitized electrical pressure signal is input as schematically indicated at line 516 to the digital processor 518. The digital processor 518 is controlled by the programmed instructions stored in program memory (ROM) 520, which are communicated as schematically illustrated at lines 522 through a latch 526 to the digital processor 518. The particular program instructions carried out by the digital processor 518 are more particularly illustrated and described in reference to the flow charts of FIGS. 18A and 18B, as hereinafter more fully described. The program instructions are addressed by the digital processor 518, as schematically represented by the lines 524 through latch 526.

Briefly summarized, the instructions stored in program memory 520 are utilized by the digital processor 518 to derive from the digitized electrical pressure signal transmission data that is representative of the applied inflation pressure which is being exerted by the syringe 16 on the balloon of the catheter, as well as other control and status signals. Program instructions then cause the digital processor to supply the transmission data to the transmission means to be wirelessly transmitted to the remote console 498.

The data memory means of the detachable module 398d is provided, in the embodiment of FIG. 16, by a scratch pad random access memory (RAM) 532 which is also accessed through latch 526 by digital processor 518. The data memory 532 is used to queue up transmission data as data packets, which can then be transmitted to the remote console 498.

The microprocessor circuit 290 monitors the status of the menu switch 502 and the select switch 500 via the control port 510, as is schematically illustrated at lines 534 and 536. In this manner, the microprocessor 290 can detect when a user has depressed either of the switches 500, 502 and then transmit that status information as transmission data to the remote console 498. Manipulation of the menu and select switches 502, 500 allow the user to control the selectable functions that are performed at the remote console 498, as is described in further detail below in conjunction with FIG. 17.

The microprocessor circuit 290 outputs the pressure and time values, the status of the select and menu switches, and other control and status information as transmission data to the control port 510, as is schematically illustrated at line 538. This transmission data is then submitted to a transmission means, via line 540, that is external to the integrated microprocessor circuit and is schematically illustrated as the components within the dotted box 542. The transmission means converts the transmission data into a transmission signal and then transmits it to the remote console 498 for further processing and display, as will be discussed in further detail below.

Illustrating one presently preferred embodiment, the detachable electronic circuit module 398d of FIG. 13 utilizes a transmission means which is comprised of a RF Transmitter circuit 546. Transmission data is then wirelessly transmitted to the remote console 498 via the radio frequency signal generated by RF transmitter circuit 546.

In the present best mode of the invention, the RF transmitter circuit 546 is comprised of RF transceiver circuitry capable of implementing the EIA CEBus (IS-60) Radio Frequency (RF) physical layer utilizing a spread spectrum technology which conforms with Federal Communications Commission Part 15 rules. The RF transceiver circuitry is comprised of a Spread Spectrum Carrier TM RF Transceiver integrated circuit having the tradename of CELinx rf, which is manufactured and sold by Intellon Corporation of Ocala, Fla. This Spread Spectrum Carrier TM circuit, covered in U.S. Pat. No. 5,090,024, is based on a direct sequence method of spreading the digital data into a broad spectrum or band. Each bit of the digital signal is spread into a unit symbol using a forward or reverse sequence of seven substates each consisting of a 360 bit chipping sequence. The bit chipping sequence approximates a forward or reverse frequency sweep from 4.2 to 6.3 Megahertz. This sequence is further modified by a 15-bit phase modulation function. The combined effect of the 360 bit chipping sequence, the 7 substate sequence and the 15-bit phase modulation function is an even spreading of the digital information across a 2.1 Megahertz band. The use of a spread spectrum method allows the system to benefit from increased signal gain inherent in processing the signal using spreading and despreading algorithms to encode the transmitted signal. This processing gain allows the system reliability to increase without increasing the power output from the transmitter.

Thus, referring to FIG. 16, the microprocessor circuit 290 encodes and formats the transmission data and then passes the transmission data to the RF transmitter circuit 546 via line 540. Microprocessor circuit 290 also monitors and controls the operation of the RF transmitter circuit 546, as is schematically shown at line 544. RF transmitter circuit 546, under the programmed control of microprocessor circuit 290, will then transmit the transmission data to the remote console 498 via the predetermined carrier frequency transmission signal, as discussed above.

Figure 14:
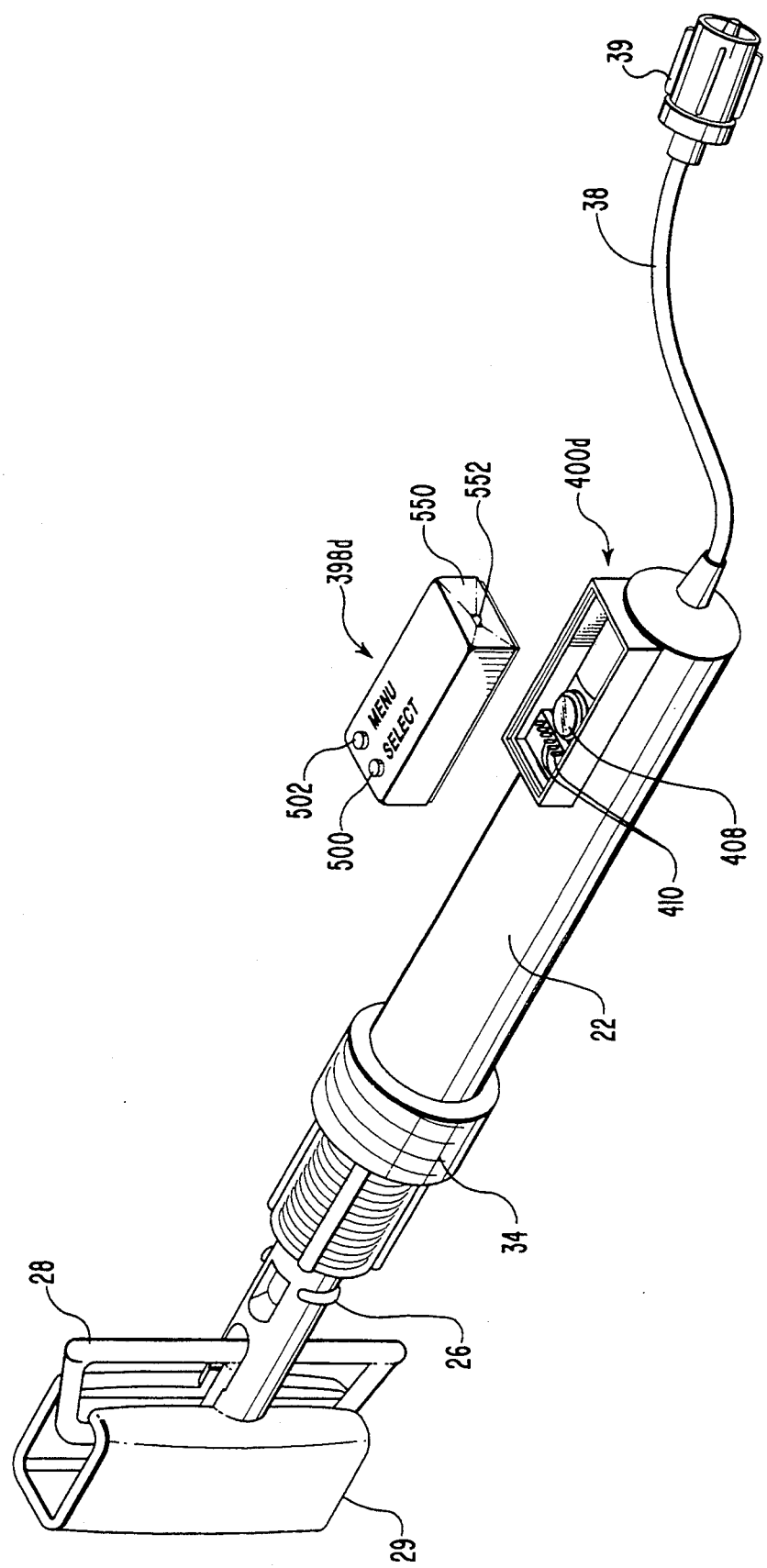
FIG. 14 is a perspective illustration showing another embodiment of the detachable electronic circuit module.

In yet another presently preferred embodiment of the transmission means, the detachable electronic circuit module 398d will utilize an infrared (IR) transmitter circuit for transmitting data to the remote console 498. In this embodiment, pressure values and other control data are output as transmission data from the microprocessor 290 via line 540 to the IR transmitter circuit. The transmission data will be converted into a IR transmission signal and then transmitted via a modulated infrared light beam to the remote console 498. This embodiment is illustrated in FIG. 14, wherein it is shown how the detachable electronic circuit module 398d will be comprised of a diffuser 550 and at least one infrared light source 552 through which the modulated infrared light beam will be transmitted.

With continued reference to FIG. 16, timer 551 communicates as schematically indicated by line 554 with the digital processor 518, and is internal to the integrated circuitry contained on the microprocessor circuit 290. Serial data receivers and drivers also communicate as schematically illustrated at lines 556 and 558 with the digital processor 518, and are internal to the integrated circuitry of the microprocessor. The serial data receivers and drivers can be used for outputting a variety of data through a serial communication output/input line as schematically indicated at lines 562, 564 and 566. Power for the microprocessor and other circuit components is supplied by the power means, as for example battery 408.

Figure 15:
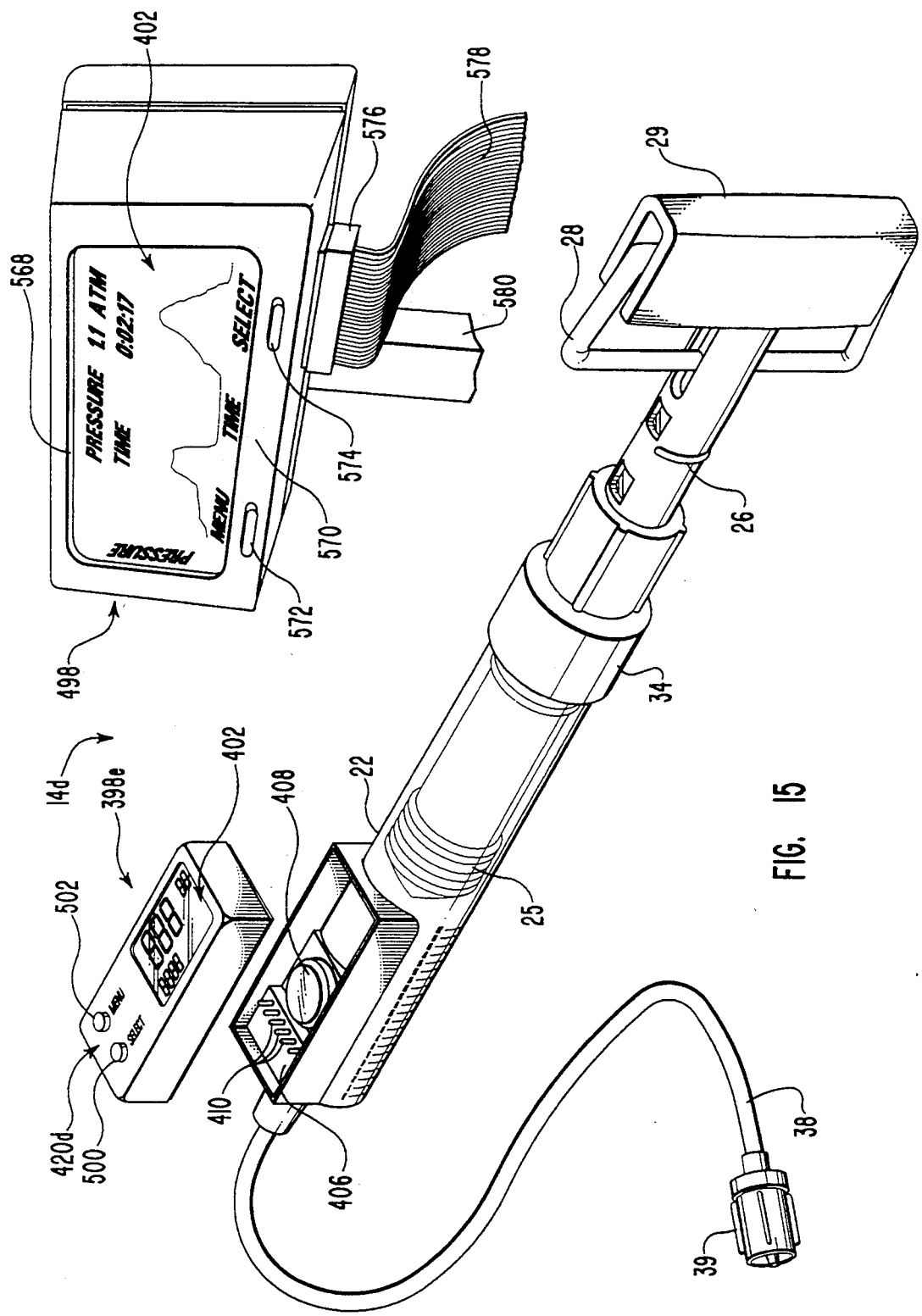
FIG. 15 is a perspective illustration showing yet a further embodiment of the detachable electronic circuit module, and a perspective view of the remote console and integrated graphic display.

Reference is now made to FIG. 15, wherein an alternative embodiment of the detachable electronic circuit module, designated at 398e, is shown. In this embodiment, detachable module 398e includes a transmission means, as for example an RF transmitter circuit 546 or IR transmitter circuit. Thus, detachable module 398e is essentially equivalent to detachable module 398d as shown in FIGS. 13 and 14. However, detachable module 398e also includes as an integral component a display means, as for example the LCD digital readout designated generally at 402. Thus, detachable module 398e is also essentially equivalent to detachable module 398 shown in FIG. 11.

In this way, detachable module 398e can be used to wirelessly transmit transmission data to the remote console 498 where inflation or deflation data will be displayed on graphic display 568. Further, the inflation or deflation data can also be viewed on the LCD digital readout 402, as discussed above in conjunction with FIG. 11.

FIG. 15 also illustrates one presently preferred embodiment of the remote console 498. The specific electronic circuitry which is used for purposes of processing the transmission data transmitted by the detachable electronic circuit module 398d is more particularly illustrated in the functional block diagram of FIG. 17, as will be described below. The graphic display 402 of the system is shown in the illustrated embodiment as being electrically connected and mounted as an integral component of the remote console 498. Preferably, graphic display 402 is capable of displaying inflation data both graphically and alphanumerically and in a manner that is readable from various angles and distances.

The remote console 498 is further comprised of a control panel 570. Disposed on the control panel is a menu switch 572 which, when activated, will cause a series of optionally selectable functions to be displayed on the graphic display 402. Select switch 574 of control panel 570 can then be used to input various control parameters as well as causing the remote console 498 to retrieve and display previously recorded inflation data. The function of the menu and select switches 572, 574 is essentially the same as the menu and select switches of controller 20 described above in conjunction with FIG. 2, and will not be further described here. Also, as noted above, transmission data representative of the status of the menu and select switches 502, 500 that are disposed on the detachable electronic circuit module 398d is also received by the remote console 498, thereby causing those switches 502, 500 to invoke the same functions as the menu and control switches 572, 574 that are disposed on the remote console 498.

Remote console 498 is also equipped with a conventional connector 576 for a printer cable 578 so that data which is recorded by the remote console 498 can be selectively printed out for permanent documentation and later reference.

Remote console 498 can be located on a stand 580 or at any other point where it can be seen by the cardiologist or clinician using the system. The remote console 498 can be switched on or off using a conventional switch (not shown) located on the console. For power, the remote console 498 is plugged into a conventional AC wall outlet, and the remote console 498 is also equipped with a battery-backed memory which provides an internal clock and timer and which retains data in memory after the remote console is switched off.

Figure 17:
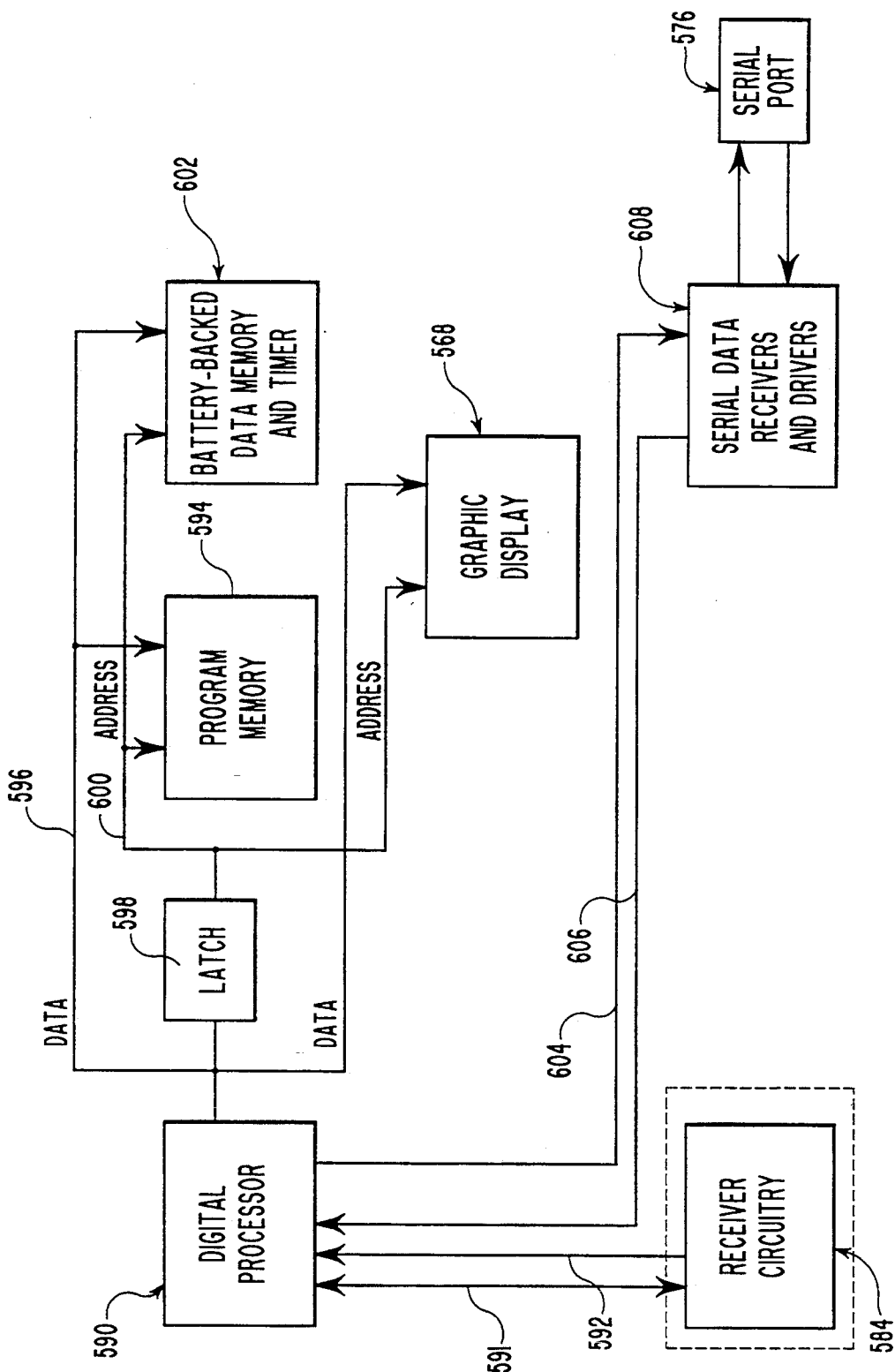
FIG. 17 is a functional block diagram which schematically illustrates the primary components of the electronic circuit used in connection with the remote console shown in FIG. 15.

With reference next to FIG. 17, the electronic circuitry contained in the remote console 498 is more particularly illustrated. In the presently preferred embodiment, the remote console 498 comprises, by way of example, receiver means for receiving the transmission data transmitted by the transmission means contained in the detachable electronic circuit module 398d and for converting lo the received transmission data into a digital form; second digital processor means for monitoring the transmission data and for processing the transmission data so as to derive, store and display digital inflation or deflation data which represents the magnitude of the applied pressure and the length of time the pressure is applied to the member; second data memory means for storing the digital inflation or deflation data derived by the second digital processor means; and second program memory means for storing machine-readable instructions utilized by the second digital processor means to monitor the transmission data and to derive, store, retrieve and display the digital inflation or deflation data.

With particular reference to the presently preferred embodiment of the remote console 498 in FIG. 17, the receiver means, is comprised of circuitry contained within the box 584. In one preferred embodiment, the receiver means receives the transmission data that is wirelessly transmitted from the detachable electronic circuit module 398d via a radio frequency. Thus in this embodiment, the receiver means is comprised of the same CELinx rf transceiver module manufactured by Intellon Corporation and described above. The received transmission data is then sent, via line 592, to the second digital processor 590.

In another presently preferred embodiment, the receiver means will be comprised of an infrared receiver circuit 584. Thus, transmission data will be transmitted to the remote console 498 via a modulated infrared signal, which will be detected and captured by a infrared sensor portion of infrared receiver circuit 584. The infrared receiver circuit 584 will convert the transmission data into a digital form, and that data will be sent to the second digital processor 590, as is schematically shown at line 592.

Also, in this embodiment, the infrared receiver circuit 584 will be comprised of multiple infrared sensors (not shown) that are appropriately positioned throughout the room in which the syringe inflation procedure is being conducted. For instance, IR sensors will be placed on the ceiling at each corner of the room. This positioning of multiple sensors insures that transmission data will not go undetected, because the infrared signal will be received regardless of where in the room the detachable electronic circuit module 398d is positioned.

With continued reference to FIG. 17, it is illustrated that from the receiver circuitry 584, the digital form of the transmission data is input, as is schematically represented at line 592, to the second digital processor 590. The second digital processor 590 is controlled by machine-readable instructions stored in program memory 594, which are communicated by a data bus, schematically illustrated as 596, running between digital processor 590 and program memory 594. The particular program instructions carried out by the digital processor 590 are more particularly illustrated and described in reference to the flow chart of FIGS. 19A–19J which will be described in greater detail in part two of the detailed description. The program instructions are addressed by the digital processor 590 through latch circuit 598 and the address bus represented at line 600.

Briefly summarized, the instructions stored in program memory are utilized by second digital processor 590 to derive from the digitized transmission data received from the detachable electronic circuit module 398d the inflation or deflation data, and to display that inflation or deflation data on the graphic display 568. The inflation or deflation data are also automatically recorded by second digital processor 590 and stored in the battery-backed data memory 602. The data is output from the graphic display 568 by way of data bus 596. The second digital processor 590 can also be programmed to display the positive inflation pressure which is output on the graphic display 568 in units of either atmospheres or pounds per square inch, as selected by the user by actuating either of the menu and select switches 502, 500 disposed on the detachable electronic circuit module 398d or on the remote console 498 (572, 574), as hereinafter more fully explained.

Second digital processor 590 can also be utilized according to the programmed instructions contained in program memory 594 to monitor and thus assist in the control of the maximum positive inflation pressure to be applied to the balloon catheter by inputting on the graphic display 568 a maximum positive pressure using the menu and select switches 502, 500. Once the maximum positive inflation pressure is reached, the second digital processor 590 will cause a portion of the graphic display 568 to flash, thereby signalling the system user that the maximum positive inflation pressure has been reached. This advantageously assists the system user in more carefully controlling and identifying the procedure used with respect to each inflation event.

In a similar manner, a selected duration for which positive inflation pressure is to be applied to the balloon catheter can also be input on the graphic display 568, again by using the menu and select switches 502, 500. Accordingly, the programmed instructions contained in program memory 594 will thereafter cause the second digital processor 590 to begin counting the duration once positive inflation pressure begins to be applied. The count will be output by processor 590 on the graphic display 568, which will then flash once the selected duration has been reached, thereby signaling the system user that positive inflation pressure has been applied for the desired length of time. Again, this significantly enhances the ability of the overall system to carefully assist in controlling the inflation procedures according to the selected parameters.

Data memory 602 is battery-backed so as to retain all data stored therein even when remote console 498 is powered off. Data memory 602 is further comprised with an electronic timer so as to provide for date and time data, and for clocking any selected maximum duration times input as described above.

Each of the control parameters which are input on the graphic display 568, via the selective operation of menu and select switches 502, 500, are input and stored in the data memory 602. In this manner, the appropriate control parameters are utilized by the program stored in program memory 594 and are also saved for later reference. In a similar manner, once a positive inflation pressure is applied the second digital processor 590 will automatically time the duration of the positive pressures and this information will likewise be recorded and stored in the data memory 602 for later reference, along with a numerical identification input to the graphic display 568 which identifies whether the particular inflation event is the first time the balloon catheter has been inflated or whether the inflation is a subsequent inflation. In this manner, each time the balloon catheter is inflated it is discretely identified and the maximum inflation pressure and time duration data corresponding to that inflation event are not only displayed but are also automatically recorded and stored in the data memory 602.

With continued reference to FIG. 17, a latch circuit 598 is used to control the gating of address data from second digital processor 590 to the respective memories 574 and 602 and graphic display 568, as is conventional in the art.

In addition to the graphic display 568, the system of the present invention also provides for output of the recorded data from second digital processor 590 through serial data lines 604, 606 to a serial data receiver and driver circuit 608, which in turn is connected to a printer port 576 to which printer cable 578 is connected.

The supply voltage used for driving the circuitry contained within the remote console means is supplied by means of a transformer (not shown) which is connected at its output to a full wave bridge rectifier (not shown) in a manner similar to that described above for controller 20 in FIG. 4, and will not be repeated here.

II. The Method

Attention is next turned to a detailed description of the presently preferred methods by which the system of the present invention is used to monitor, display and automatically record PTCA inflation or deflation data.

A. FIGS. 6A-6G.

The method by which controller 20 is programmed to carry out monitoring, display and recording of PTCA data as illustrated in FIGS. 6A-6G is described in detail in U.S. Pat. No. 5,135,488 incorporated herein by reference in its entirety.

B. FIG. 10.

Figure 10:
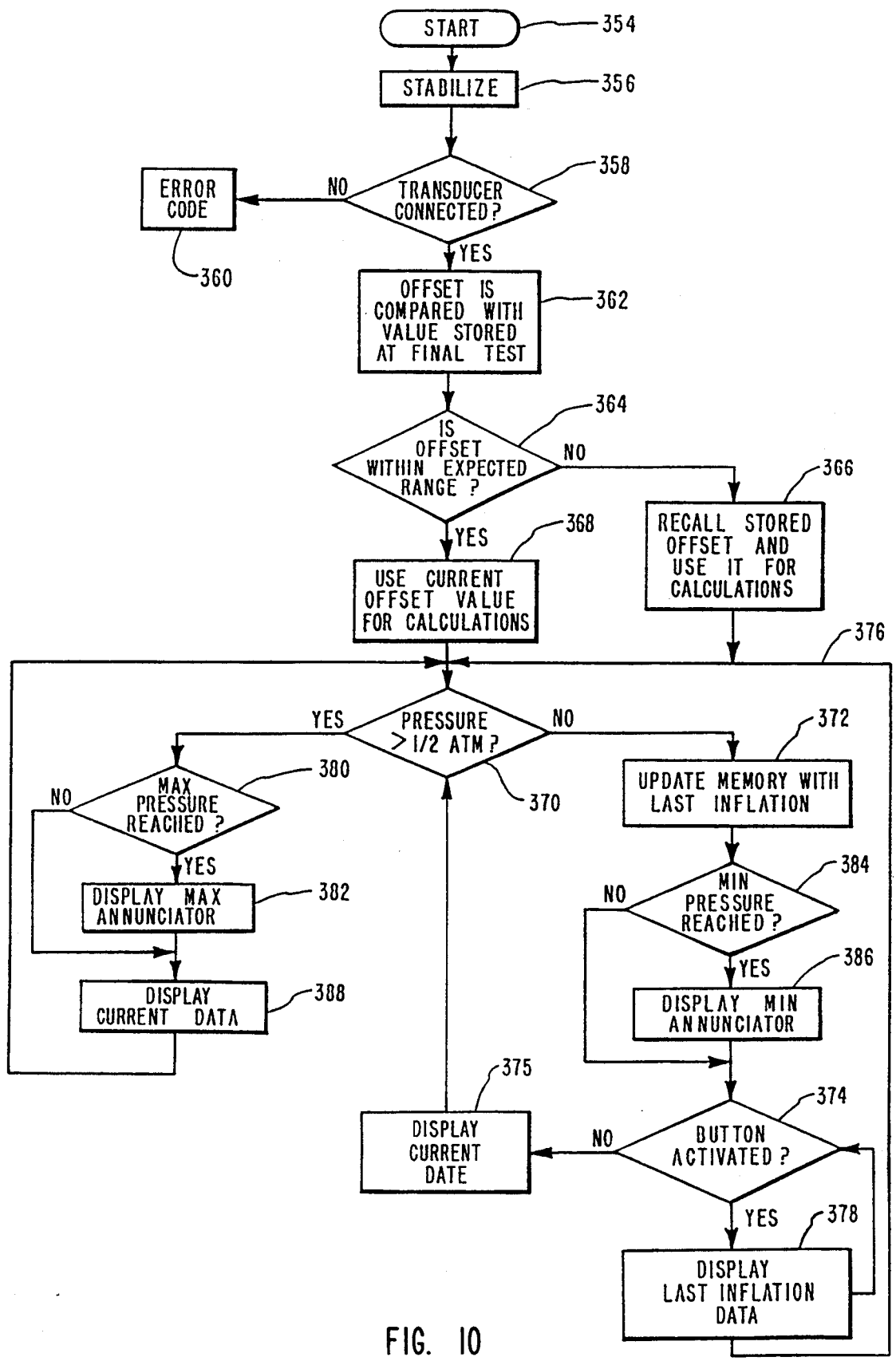
FIG. 10 illustrates a flow chart showing one presently preferred method for programming the digital processor of the electronic circuit means which is utilized for the syringe system in the embodiment of FIG. 7.

The method by which controller 20a is programmed to carry out monitoring, display and recording of PTCA data as illustrated in FIG. 10 is described in detail in U.S. Pat. No. 5,201,753, incorporated herein by reference in its entirety.

C. FIG. 20.

Figure 20:
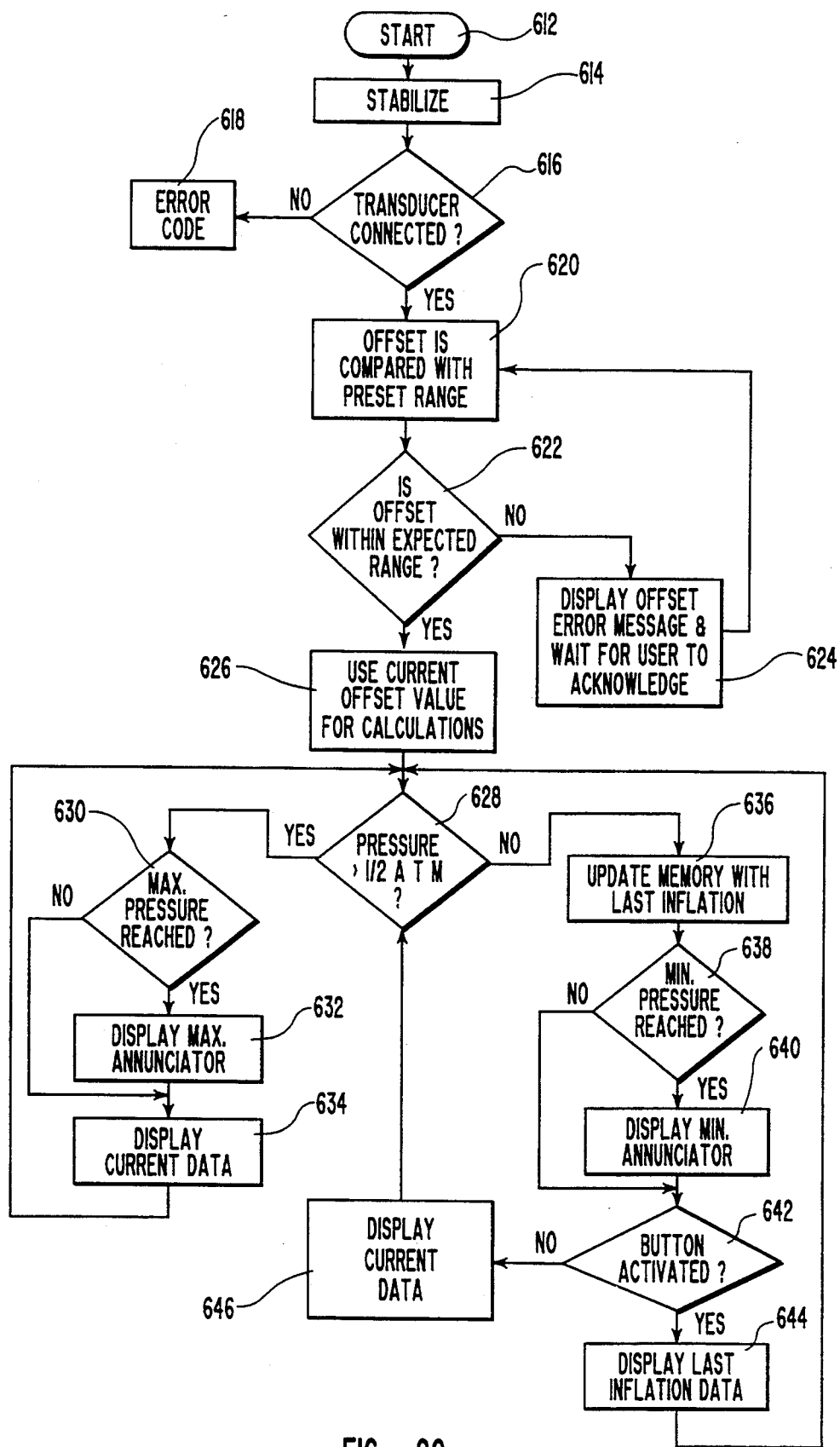
FIG. 20 illustrates a flow chart showing one presently preferred method for programming the digital processor of the detachable electronic circuit module shown in FIG. 11.

The embodiment of the program instructions as illustrated in the flow chart of FIG. 20 is particularly designed for programming the microprocessor 290 described in connection with the detachable electronic circuit module 398 of the syringe system 14b and illustrated in FIGS. 11 and 11A-11D.

As discussed above in connection with FIGS. 11 and 11A-11D, the microprocessor 290 and its related circuitry contained within the detachable electronic circuit module 398 is essentially the same as the microprocessor 290 and circuitry of the controller 20a of FIGS. 7-9. Thus, the program instructions of FIG. 20 differ from those of FIG. 10 only with respect to the instructions involving the calibration of the transducer 42. In FIG. 20, the microprocessor 290 checks to make certain that the transducer 42 is connected to the rest of the circuitry at step 616. If the transducer 42 is connected, the microprocessor 290 moves to the next step to determine the transducer's offset at zero pressure.

As noted in conjunction with FIG. 10, the preferred setup protocol is for a system user to measure offset at no pressure, and then use that value for subsequent pressure calculations. But, as was also noted in connection with the embodiment of FIG. 10, each transducer 42 undergoes a final test in conjunction with a specific controller 20a so as to determine a default zero offset value. Thus, if the user forgets to measure the offset at zero value, the system of FIG. 10 will default to this previously stored default value.

However, in the embodiment of FIGS. 11 and 11A-11E, a single default offset value cannot be established since the detachable electronic circuit module 398 is intended to be reused with a number of transducers. Consequently, no single default zero offset value can be assigned to a detachable module 398. Thus, in FIG. 20 at step 620, the microprocessor 290 attempts to determine the transducer's offset while no pressure is being applied by the syringe. This measured offset value is then compared with a predetermined and preset pressure range at step 622. If the current measurement of offset falls within the preset range, then the microprocessor 290 will proceed to step 626 and use the measured offset value in all subsequent calculations of the actual applied pressure. If, however, the user begins to apply pressure before determining the zero offset, then that will be detected at step 622 because the measured offset value will fall outside of the preset range. In that case, the microprocessor 290 will move to step 624, display an "offset error" message on the display 402, and wait for the user to acknowledge before proceeding again with step 620. The microprocessor 290 will repeat this procedure until the measured offset value falls within the preset range. In this manner, the user is forced to calibrate the transducer 42 at zero pressure. This insures that subsequent pressure readings are accurate and reliable.

Once the transducer offset value is determined, the remaining steps illustrated in FIG. 20 are identical in every respect to the steps in FIG. 10. Thus, that discussion will not be repeated here.

In the embodiment outlined in FIG. 11F, the addition of a static memory device 565 such as Dallas Semiconductor's DS2224 will allow the critical parameters, such as the zero offset of a particular transducer 42, to be stored in memory 565 for later recall by the detachable electronic circuit module 398 at connection N (which is available at an electrical prong 410) via the serial input/output line 566 shown in FIG. 16. Other critical parameters, such as sensitivity and pressure range can also be recalled once the connection between the detachable electronic circuit module 398 and the syringe is made. In this embodiment the method described in connection with FIG. 10 applies, wherein the previously stored offset value for the transducer 42 is recalled from memory.

D. FIGS. 18A–18B.

Figure 18A:
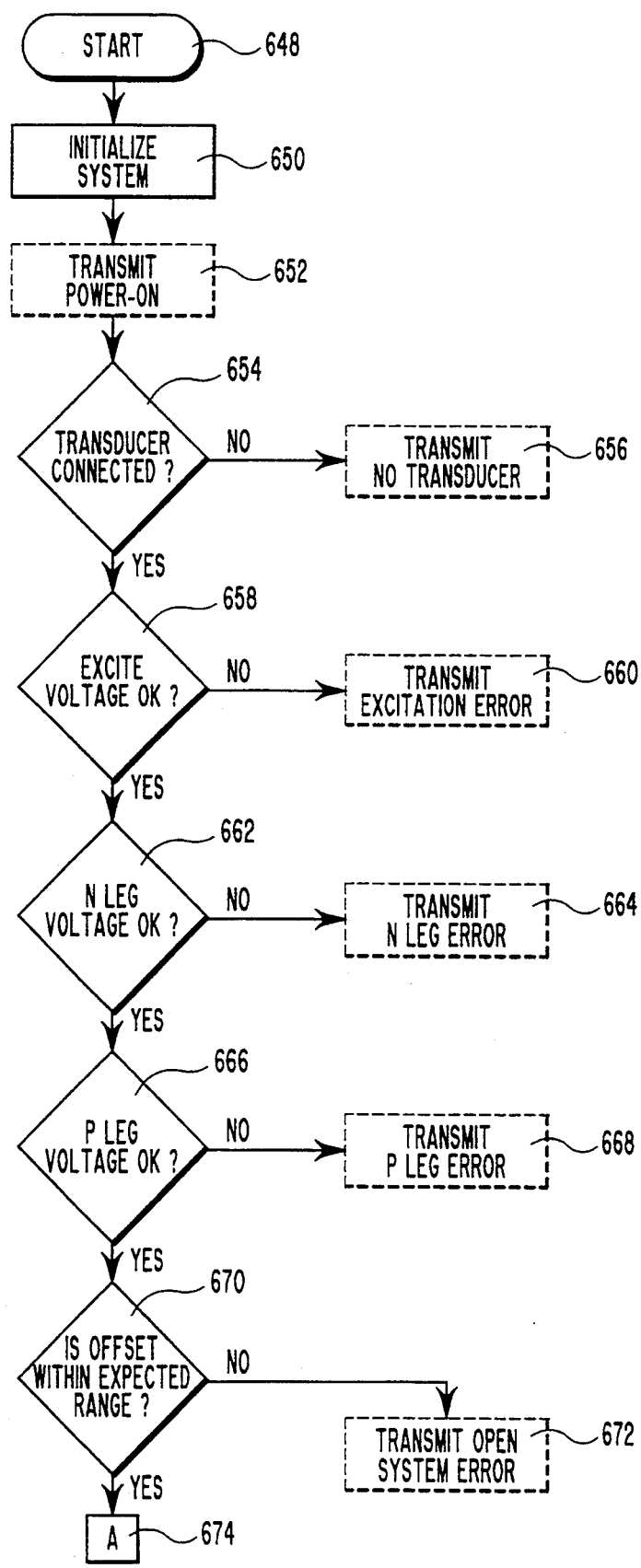
FIGS. 18A through 18B taken together illustrate a flow chart showing one presently preferred method for programming the digital processor of the detachable electronic circuit module shown in FIG. 16.
Figure 18B:
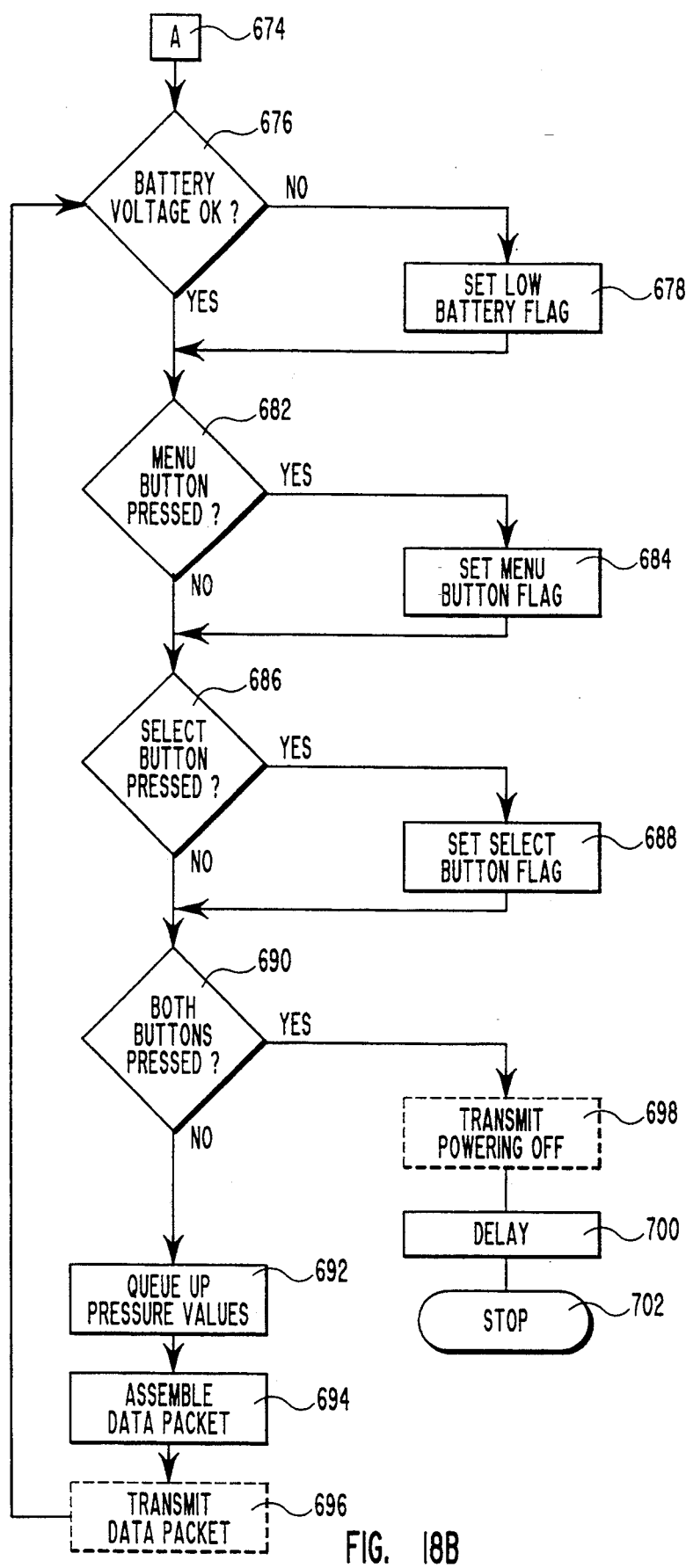

The embodiment of the program instructions as illustrated in the flow chart of FIGS. 18A and 18B is particularly designed for programming the microprocessor 290 described in connection with the detachable electronic circuit module 398d of the syringe system 14d of FIGS. 13–17, wherein transmission data is wirelessly transmitted to the remote console 498.

Referring to FIG. 18A and starting at step 648, once menu button switch 502 and select button switch 500 are activated simultaneously the detachable electronic circuit module 398d is powered on. At step 650, the processor 290 and its associated electronics system are initialized, and the appropriate program instructions are loaded into the digital processor portion 518 of the microprocessor 290. The microprocessor 290 then moves to step 652 at which time a status flag indicating that the detachable electronic circuit module 398d has been powered on is transmitted to the remote console 398d via the transmission circuitry 542 (FIG. 16).

The microprocessor 290 then performs a series of diagnostic steps. At step 654, the microprocessor 290 checks to make certain that the transducer 42 is connected to the rest of the circuitry contained in the module 398d. If not, a status flag indicating "no transducer" is transmitted to the remote console 498 at step 656. If transducer 42 is connected, microprocessor 290 proceeds to step 658 and checks the excitation voltage of the transducer 42. If the excitation voltage is incorrect, a status flag indicating "excitation error" is transmitted to the remote console 498 at 660. If the excitation voltage is correct, the microprocessor then proceeds to step 662 where the N-Leg voltage of the transducer 42 is checked. If incorrect, a status flag indicating "N-Leg error" is transmitted to the remote console 498 at 664. If N-Leg voltage is correct, microprocessor 290 proceeds to step 666 and checks the P-Leg voltage of the transducer 42. Again, if incorrect, a status flag indicating the error is transmitted to the remote console 498 at step 668. If correct, the microprocessor 290 proceeds to step 670.

At step 670, the microprocessor 290 determines the zero pressure of the transducer 42 and compares that value to a predetermined offset range. If the value falls outside of that range, a status flag indicating an "open system error" is transmitted to the remote console 498 at step 672. If the value falls within the range, the microprocessor 290 proceeds to step 676, shown on FIG. 18B. At step 676, the microprocessor 290 checks the battery voltage level. If the voltage level is sufficient, the microprocessor proceeds to step 680. If the voltage level is below a selected point, the microprocessor 290 warns the user by setting a "low battery status" flag at step 678, which will subsequently be transmitted to remote console 498, before continuing to step 680.

Having completed all of the diagnostic steps, the microprocessor 290 begins to monitor the electrical pressure signal from the transducer 42, which signal has been digitized and input to the digital processor 518 as previously described in connection with FIG. 16. Thus, the processor 518 proceeds to step 682 and begins to monitor the status of the menu and select control switches 502 and 500 disposed on the control panel 420d of the detachable electronic circuit module 398d. At step 682, the microprocessor 290 checks to see if the menu button 502 is being pressed by the user. If not, the processor 290 proceeds directly to step 686. If menu button 502 is pressed, the processor 290 sets the "menu button" flag at step 684 and then proceeds to step 686. At step 686, microprocessor 290 determines whether the select button 500 is being pressed by the user. If not, the processor 290 proceeds to step 690. If select button is pressed, processor sets the "select button" flag at step 688 before proceeding to step 690.

At step 690 the microprocessor 290 determines if the menu button 502 and select button 500 are being pressed simultaneously. Pressing both buttons simultaneously causes the detachable electronic circuit module 398d to power off. In that case, the processor 290 jumps to step 698 and transmits a "powering off" data packet message to the remote console 498. The processor 290 will then delay for a period of time to allow the remote console 498 to receive and respond to the message, as is indicated at step 700. The processor 290 will then halt the program at step 702.

If both the menu and select buttons 502, 500 are not being simultaneously pressed, the processor will proceed to step 692 and queue up the pertinent transmission data. The processor 290 then, at step 694, assembles a data packet, comprising transmission data such as the pressure values, the status of the menu and select buttons 502, 500, battery voltage status, or other relevant status information. In the preferred embodiment, the data packet will include the current pressure value as well as pressure values from the previous two or three transmissions. This insures that pressure values are not inadvertently lost if, for instance, a particular transmission fails. The processor 290 then causes the data packet to be wirelessly transmitted, via the transmitter circuitry, to the remote console 498 at step 696. After transmission, the processor returns to step 676 and continues to process, as described above.

Thus, the detachable electronic circuit module 398d will, once it has powered on and run through a diagnostic procedure, continuously transmit transmission data to the remote console 498. This will continue until the user simultaneously presses the menu and select buttons 502, 500, and thereby powers off the detachable electronic circuit module 398d.

E. FIGS. 19A–19F.

FIGS. 19A–19F illustrate the presently preferred embodiment of the instructions which may be utilized to control the second digital processor 590 contained within the remote console 498 discussed above in conjunction with FIG. 17.

Figure 19A:
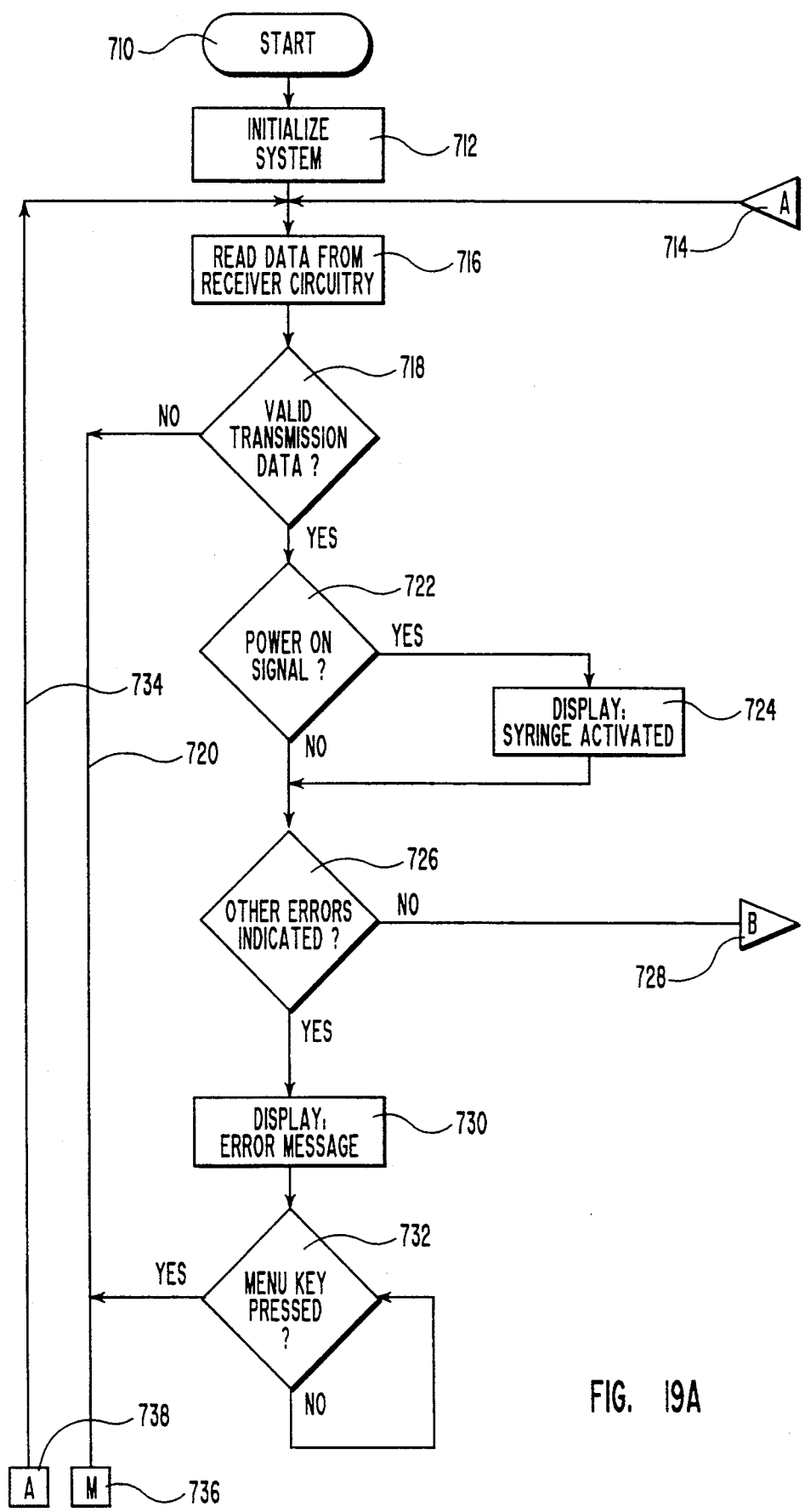
FIGS. 19A through 19F taken together illustrate a flow chart showing one presently preferred method for programming the processor of the remote console shown in FIG. 17.

With reference to FIG. 19A, when the remote console 498 is powered on, the program starts as indicated at step 710 and then moves to step 712 which causes the system to initialize. During initialization, the appropriate program instructions are loaded from program memory 594 into the digital processor 590 (shown in FIG. 17). The system then moves to step 716 which causes the processor 590 to read the data contents of the receiver circuitry (584 in FIG. 17). The processor 590 then, in step 718, checks whether the contents of the receiver circuitry 584 constitutes valid transmission data that has been transmitted by the detachable electronic circuit module 398d. If the transmission data is not valid, the process will move as indicated at flag 736 to the portion of programmed instructions illustrated in FIG. 19B.

If however the transmission data is valid, the processor 590 will move to step 722, and check whether the detachable electronic circuit module 398d has transmitted a "power on" signal. If so, the processor will cause a message to be output on the graphic display 568 signifying that the syringe has been activated at step 724, and then proceed to step 726. If a "power on" signal has not been transmitted, the processor 590 will proceed directly to step 726, where it will check to see if any other errors have been detected and transmitted by the detachable electronic circuit module 398d. If there are not any other errors indicated, the processor moves as indicated at flag 728 to the portion of the programmed instructions illustrated in FIG. 19E, described in further detail below. If there are errors detected, the processor 590 will cause a corresponding message to be displayed on the graphic display 568 indicating that a particular error has occurred at step 730. The processor will then await acknowledgement from the user by waiting for the user to press the menu switch 502, as is indicated at step 732. Once the user has depressed the menu switch 502, the process will move, as indicated at flag 736, to the portion of the programmed instructions illustrated in FIG. 19B.

Figure 19B:
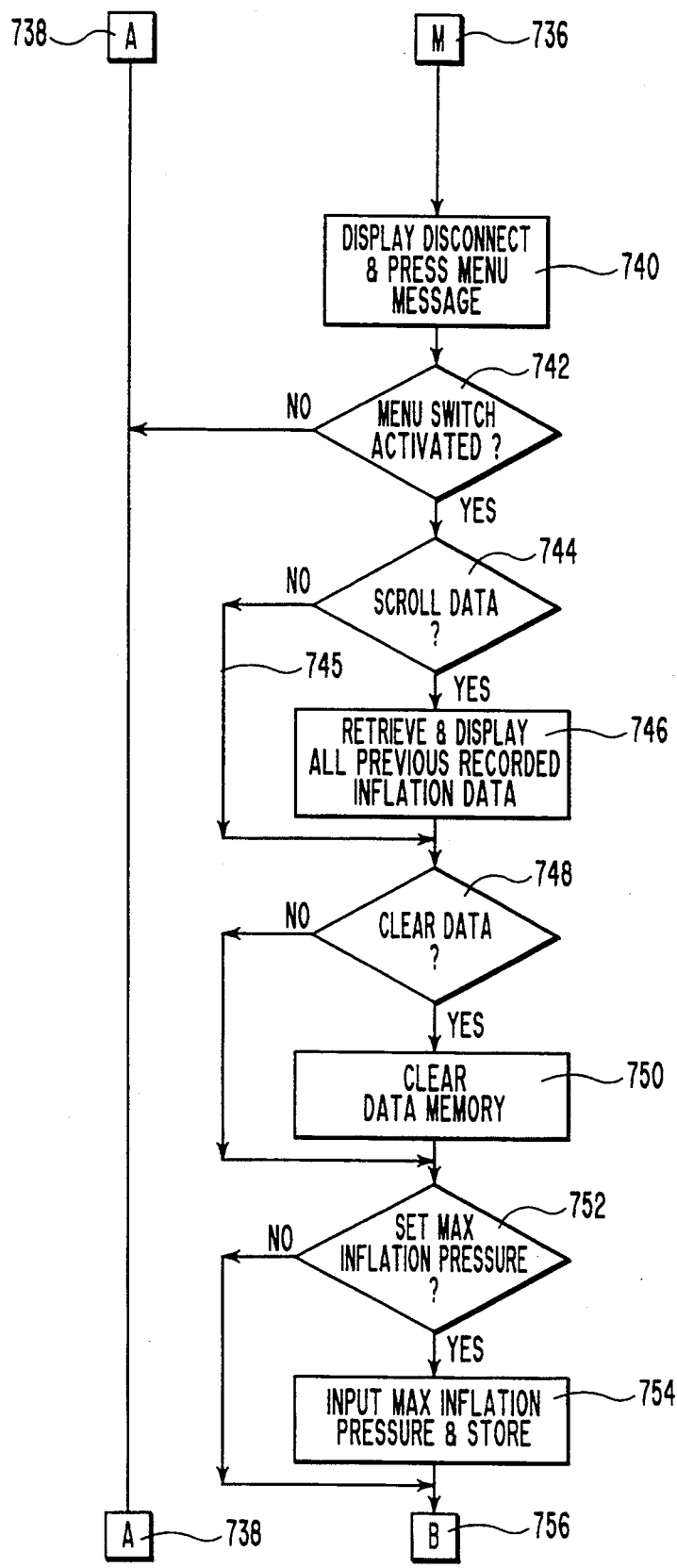

As is indicated at step 740 in FIG. 19B, the processor 590 will cause a message to be displayed on the graphic display 568 signifying that the detachable electronic circuit module 398d is not communicating with the transducer 42 and instruct the user to press the menu switch 502. The processor then moves to step 742 to check whether the menu switch 502 has been activated and if not returns to step 716 as schematically illustrated at 738 and continues in that loop until the menu switch 502 is activated by the user.

Once the menu switch is activated at step 742, the processor then moves to step 744 and causes the graphic display 568 to display a message inquiring whether the inflation data previously recorded by the system 14d is to be scrolled at the graphic display 568. If the system user desires to review the previously recorded inflation data, the select switch 500 is activated and the processor 590 then proceeds to step 746 which causes all of the previously recorded inflation data for each inflation event to be retrieved in sequence and displayed. If at step 744 the system user does not wish to scroll the previously recorded inflation data, the menu switch 502 is activated which causes the processor 590 to skip step 746 as schematically illustrated at line 745 so as to proceed with the next inquiry as represented at step 748.

At step 748 the system causes a message to be displayed on the graphic display 568 inquiring whether previously recorded inflation data which has been previously stored in the data memory 602 is to be cleared. If the select switch 500 is activated this causes the processor 590 to clear the previously recorded inflation data from data memory 602, as indicated at step 750. If the previously recorded inflation data is not to be cleared from data memory 602, the menu switch 502 is activated which causes the system to skip step 750 and to move to the next inquiry as represented at step 752.

Figure 19C:
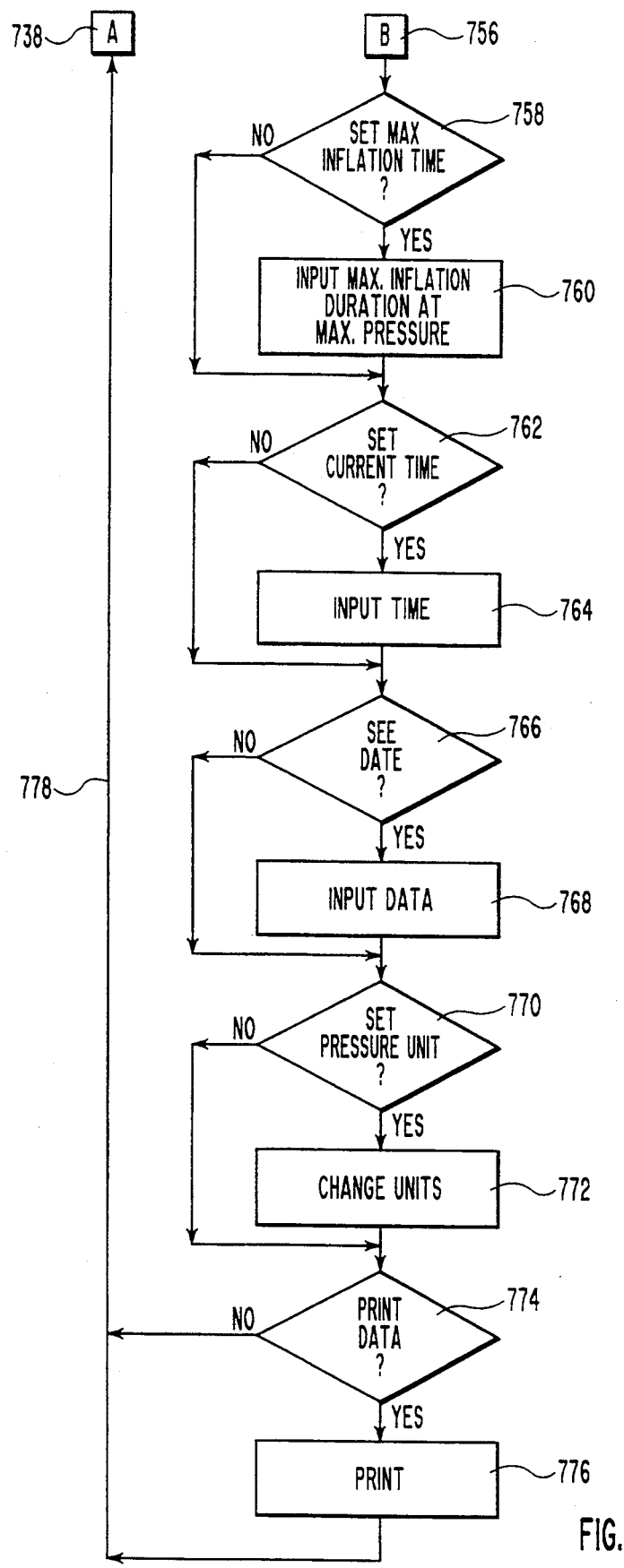

At step 752 the system causes the graphic display 568 to display an inquiry with respect to whether an upper limit is to be set with respect to the maximum positive inflation pressure to be applied with respect to the next inflation event. If so, the select switch 500 is activated and is used to input the selected maximum positive inflation pressure through the data transfer bus 596 (FIG. 17), to the data memory 602 for later reference, at step 754. If a maximum inflation pressure is not selected at step 752, the menu switch 502 is activated which causes the system to skip step 754 and move to the next inquiry, via flag 756, as represented at step 758 (FIG. 19C).

At step 758 the system displays a message at the graphic display 568 inquiring whether the maximum duration for application of positive pressure is to be selected. If so, the select switch 500 is again activated which causes the system to move to step 760 and the select switch 500 is then used to input at the graphic display 568 the selected duration. This selected duration is input by means of the corresponding graphic display circuitry 568 (see FIG. 17) through the data transfer bus 596 to the data memory 602 for later reference.

In a manner similar to that described above in connection with the preceding inquiry steps, the system continues to inquire whether the current time and date are to be displayed, as represented at steps 762 and 766, respectively. If so, by utilizing the select switch 500 as described above, the current date and time may be entered at the graphic display 568. However, the internal clock that is part of the circuitry in processor 590 will typically make it unnecessary to enter these parameters. The system then moves through the series of steps represented at 770, 772, 774, and 776 where it determines the pressure units to be displayed at the graphic display 568 as well as determining whether data is to be printed. After the print inquiry has been responded to by utilization of the appropriate menu or select switch 502, or 500, respectively, the system returns as illustrated at line 778 to step 716.

As will be appreciated from the foregoing, the portion of the program instructions which are carried out according to the flow chart of FIGS. 19A-19C pertains to that part of the program which permits a series of optionally selectable functions to be sequentially displayed for purposes of inputting various control parameters which are later utilized in displaying and automatically recording the data, as well as utilizing these control parameters to alert the system user when selected limits are reached with respect to maximum positive inflation pressure and duration of positive inflation pressures.

Figure 19D:
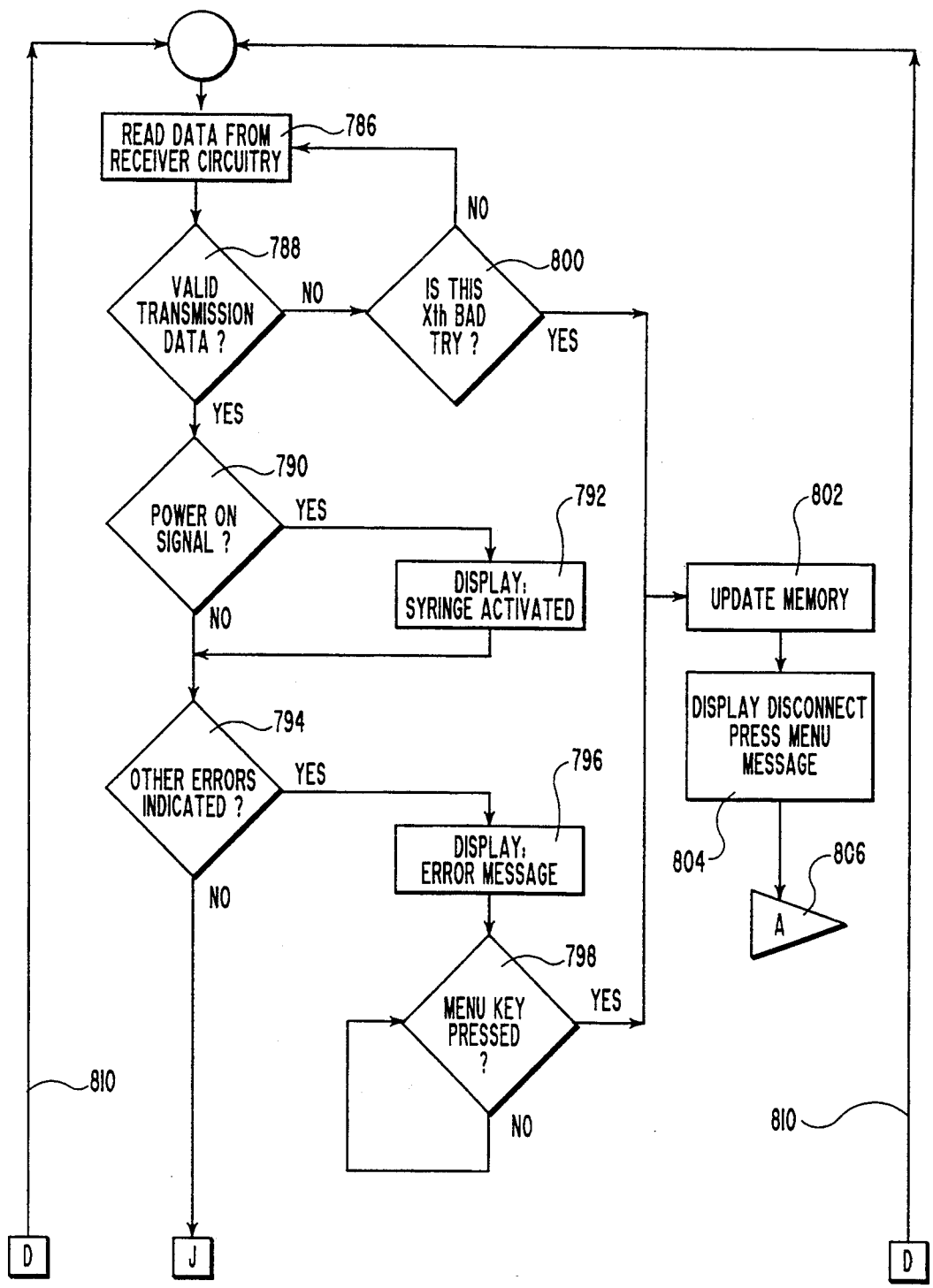
Figure 19E:
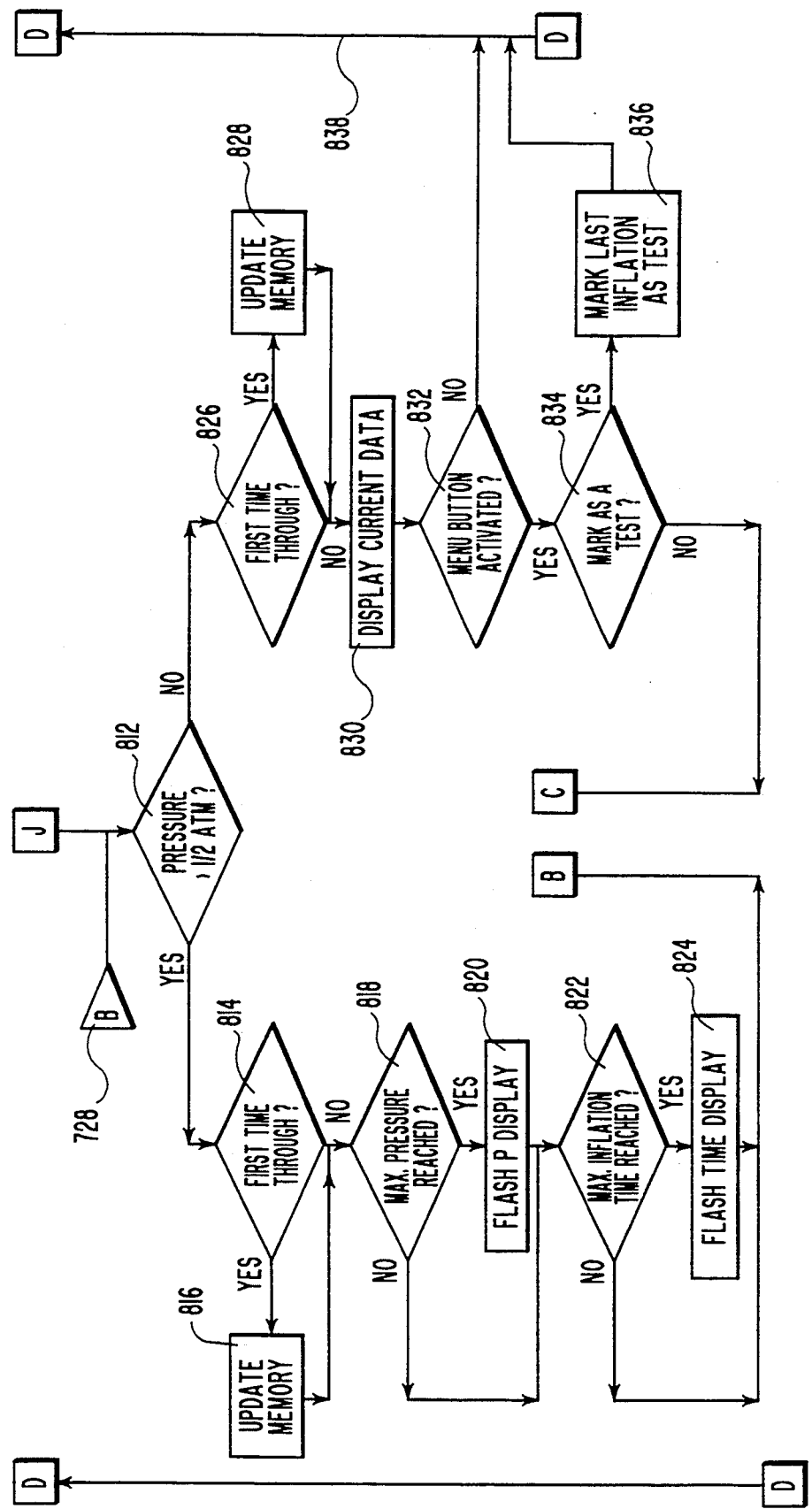
Figure 19F:
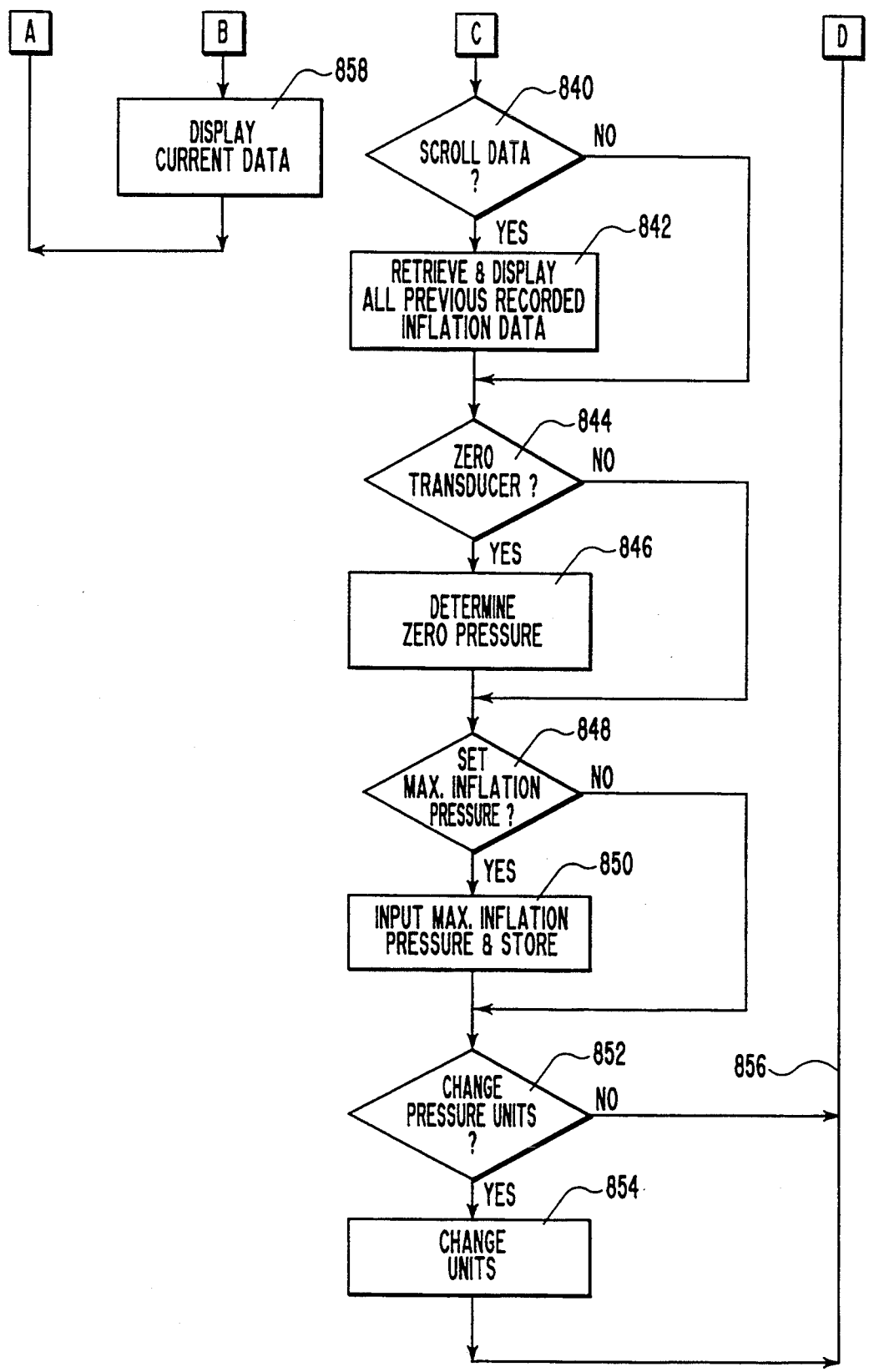
Figure 19G:
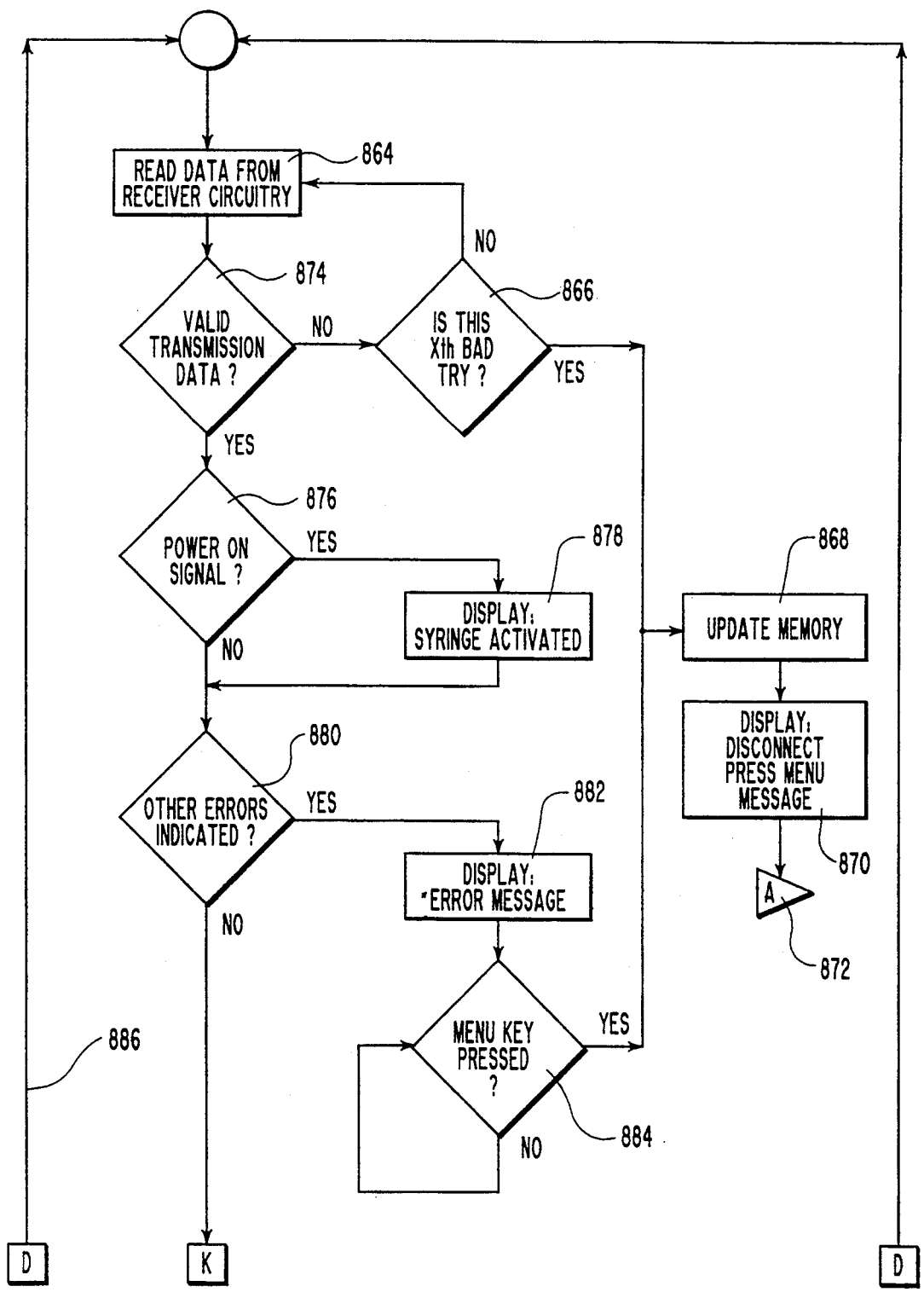
FIGS. 19G through 19J taken together illustrate a flow chart showing a second presently preferred method for programming the digital processor of the remote console shown in FIG. 17.

Once it is determined that the transducer 42 is properly connected to the detachable electronic circuit module 398d, the remote console 498 processor 590 moves to that portion of the program illustrated in FIGS. 19D–19F, as is indicated at flag 728 (FIG. 19E), where it then starts as schematically indicated at step 812. At this portion of the program, processor 590 begins to monitor the pressure values transmitted by the detachable electronic circuit module 398d.

Thus, if the pressure which is sensed at transducer 42 is less than one-half atmosphere, the system moves to that portion of the program which commences with step 826. At that step the system first determines whether it is in the first pass through of the loop started by step 826 and if so moves to step 828 where the data memory 602 is updated. The effect of updating the data memory 602 at step 828 is that the time with respect to termination of the last inflation is recorded and stored in the data memory 602. Once that step has been completed, the system then moves to step 830. In the alternative, if at step 826 the system determines that it is not the first pass through this loop of the program, the system moves directly to step 830 and displays the current data with respect to the inflation number, duration time, and pressure. The system then moves to step 832 where the processor 590 checks the status of the menu switch 502.

If the menu switch 502 is activated in this condition the system moves to the next step 834 where the last inflation data can be marked as an initial test or not, as desired by the system user. If the initial inflation is merely a test it is marked at step 836 prior to returning to step 786 (via line 838), otherwise the system moves to step 840 (FIG. 19F) to determine whether any previously recorded inflation data is to be scrolled. If the data is scrolled the system moves to step 842 and retrieves and displays in sequence all previously recorded inflation data for each prior inflation event, otherwise the system jumps to step 844.

Similarly, the system can also proceed through steps 844, 848, and 852 which will permit the transducer 42 to again be zeroed (step 846), or to set a new maximum positive inflation pressure (step 850) or to change the pressure units (step 854) by entering any of these selections using the select switch 500. The system then returns to step 786 via line 856.

Once the inflation pressure applied to the balloon catheter begins to exceed a predetermined level, as for example about one-half atmosphere, by insertion of the syringe plunger 24, the system moves from step 812 to the program step 814 (FIG. 19E). At that step the system determines whether this is the first time through the part of the program loop which begins with step 814 and if so updates the data memory 602 at step 816. The effect of updating the data memory 602 at step 816 is that the processor 590 causes the duration of the previous inflation to be recorded. After update memory step 816 has been performed, or in each subsequent pass through step 814, the system then moves to step 818 where the system checks to determine whether the inflation pressure has reached any selected maximum positive inflation pressure input for this inflation event. If the selected maximum inflation pressure is reached the system moves to step 820 and causes a pressure display readout portion on the graphic display 568 to begin flashing so as to signal the system user that the selected maximum inflation pressure has been reached. If the selected maximum inflation pressure has not been reached or if none was selected, the system then jumps to step 822.

At step 822 the system checks to determine whether any selected duration has yet been clocked with respect to a selected duration for application of positive pressure and if so then moves to step 824 so as to cause a time display portion on the graphic display 568 to begin flashing, thereby signalling the system user that the selected duration has been achieved. If no duration is input or if the selected duration has not been reached the system moves to step 858 (FIG. 19F) which causes the system to display the current data with respect to the inflation pressure being applied and the length of time that positive inflation pressure has been applied. The system then returns to the beginning of the loop at step 786.

At step 786, processor 590 reads the new contents of the receiver circuitry 584 (FIG. 17). The system then checks whether this newly read data is valid transmission data at step 788. If the data is not valid, the system will continue to read the contents of the receiver circuitry 584 for a predetermined number of iterations, as is indicated at step 800. Having exhausted the predetermined number of iterations, which indicates that the communications link between the detachable electronic circuit module 398d and the remote console 498 has been lost, the system will proceed to step 802 where data memory 602 will be updated so as to mark the time of disconnection. The system will then cause the graphic display 568 to display a "disconnect" message to the user and instruct the user to press the menu switch 502, and then will return to step 716, as is indicated at flag 806.

If data read from the receiver circuitry 584 is valid at step 788, the system will proceed to step 790. There, the system checks the "power on" flag generated by the detachable electronic circuit module 398d. If the flag is set, the system will cause the graphic display 568 to display a "syringe activated" message before proceeding to step 794. If the power on flag is not set, the system will proceed directly to step 794.

At step 794, the system will continue checking the status flags transmitted by the detachable electronic circuit module 398d, as discussed above in connection with FIGS. 14A and 14B. If those flags indicate any error conditions, the system will cause the graphic display 568 to display an appropriate error message and will then wait for the user to acknowledge by pressing the menu key 502 at step 798. When the menu key is pressed, the system will update memory 602 at step 802 (so as to mark the time of disconnection), display a "disconnect" message on the graphic display 568 and instruct the user to press the menu switch 502 at step 804, and then return to step 716, as is indicated at flag 806. If no errors are indicated, the system will proceed to step 812 (FIG. 19E) and continue to monitor and process the inflation data transmitted by the detachable electronic circuit module 398d, in the same manner as described above.

F. FIGS. 19G–19J.

Figure 19H:
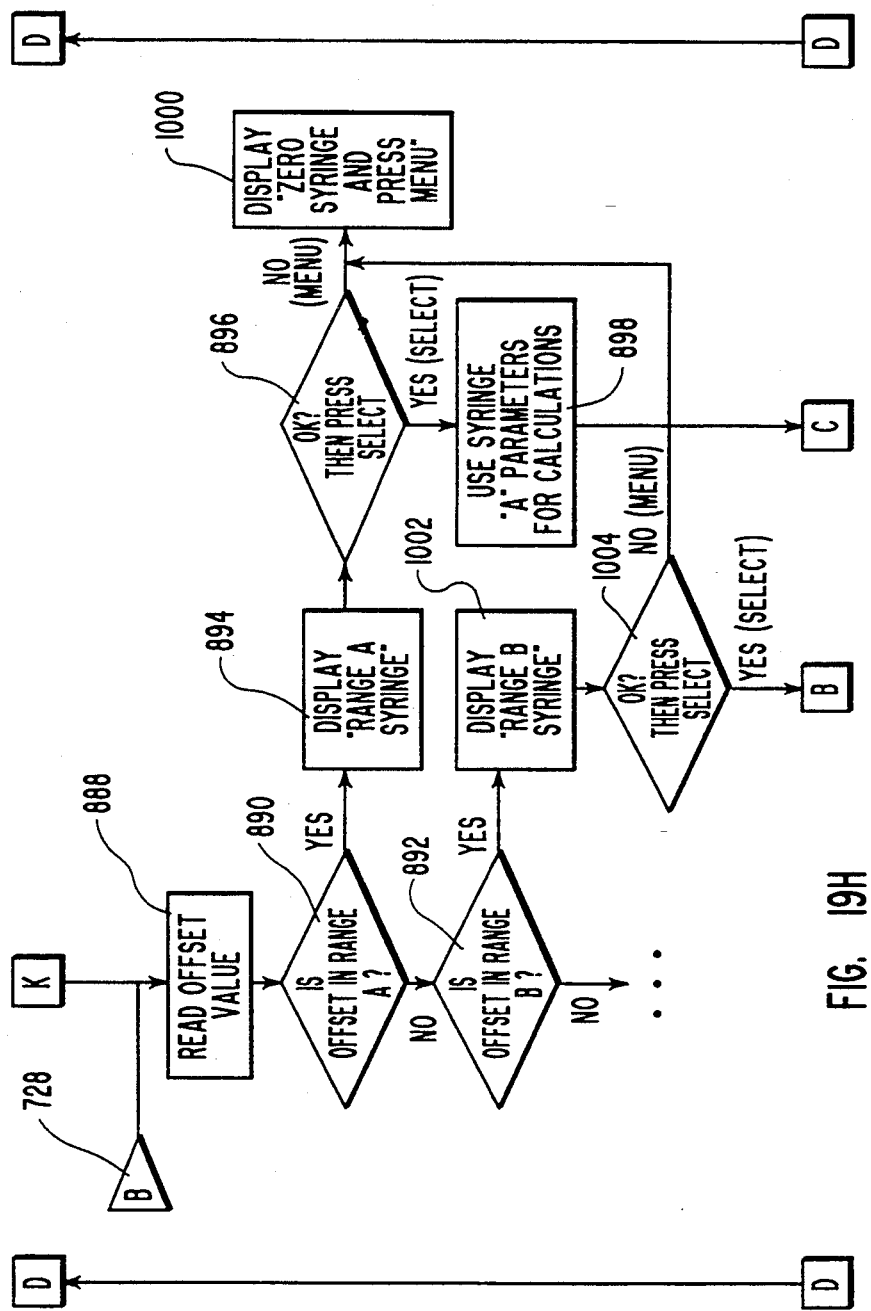

An alternative embodiment for programming and controlling the processor 590 contained within the remote console 498 is illustrated in FIGS. 19G–19J. This portion of the program instructions can be used in place of those instructions illustrated in FIGS. 19D–19F. As with those instructions, once the transducer 42 is properly connected to the detachable electronic circuit module 298D, the remote console 498 processor 590 moves to the portion of the program illustrated in FIGS. 19G–19J as indicated at Flag 728 (FIG. 19H).

At step 888, the system proceeds to step 888 (FIG. 19H) where the microprocessor 590 proceeds to read the offset value of the connected transducer 42. The transducer offset value is the actual pressure which is read by the transducer 42 when there is no pressure applied by the syringe system 14d.

This offset is then compared to a plurality of offset values which have previously been stored in the program memory 594 of the microprocessor 590. By taking the difference between the actual offset value and the other previously stored offset values which have been programmed into the microprocessor 590, it can be determined whether the actual measured offset value is within any one of a number of preselected ranges for the offset value.

For example, as illustrated in FIG. 19H at step 890, it may be determined whether the measured offset is within a first range, range A. If so, the system then displays a message at step 894 to the system user which identifies to the user the particular offset range which was identified and the type of syringe which corresponds to that range of offset values. In other words, the transducer 42 may be designed so that it has a selected value of offset at the time the transducer circuit is manufactured.

Figure 6A:
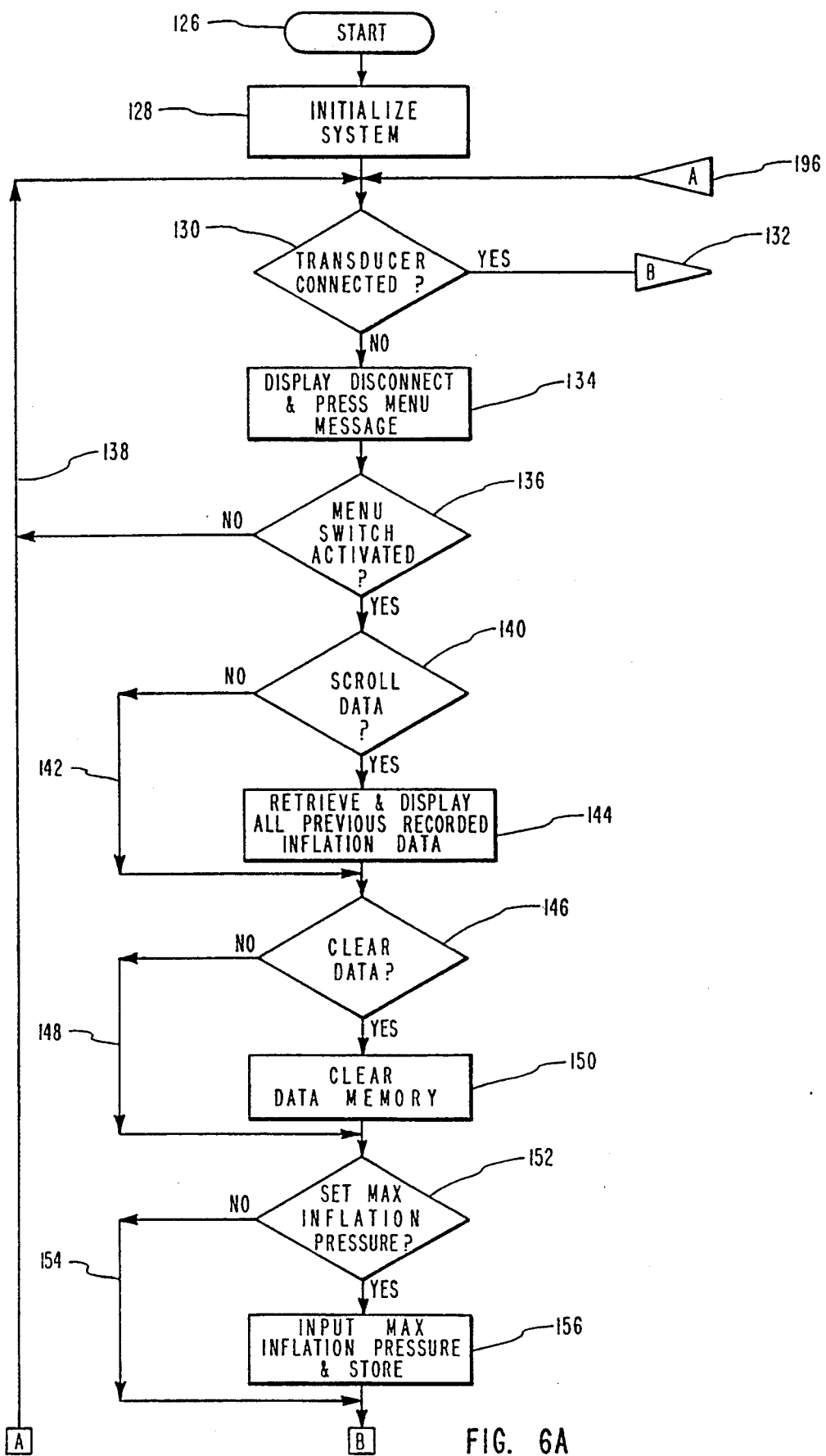
FIGS. 6A through 6D taken together illustrate a flow chart showing one presently preferred method for programming the digital processor of the electronic circuit means in accordance with the method of the present invention.
Figure 6B:
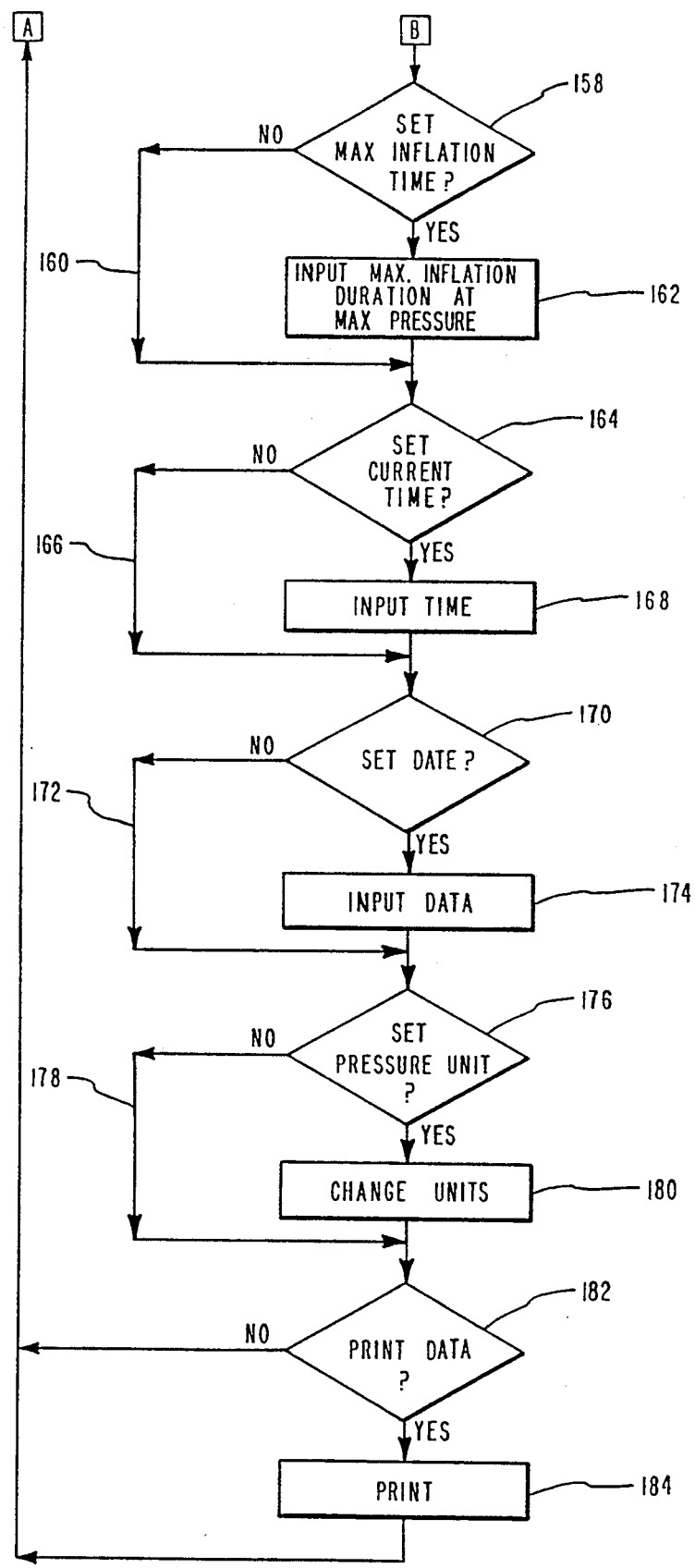
Figure 6C:
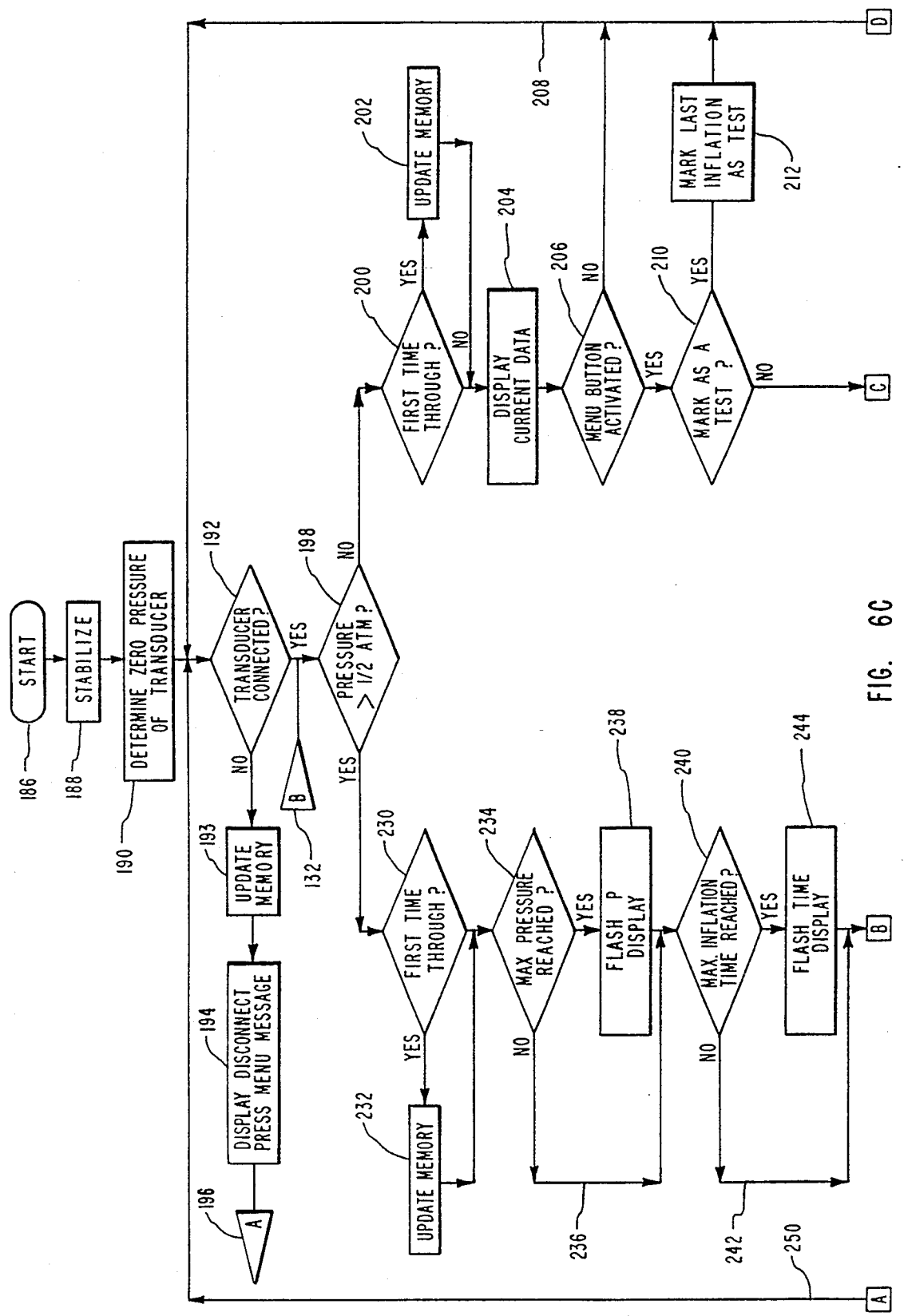
Figure 6D:
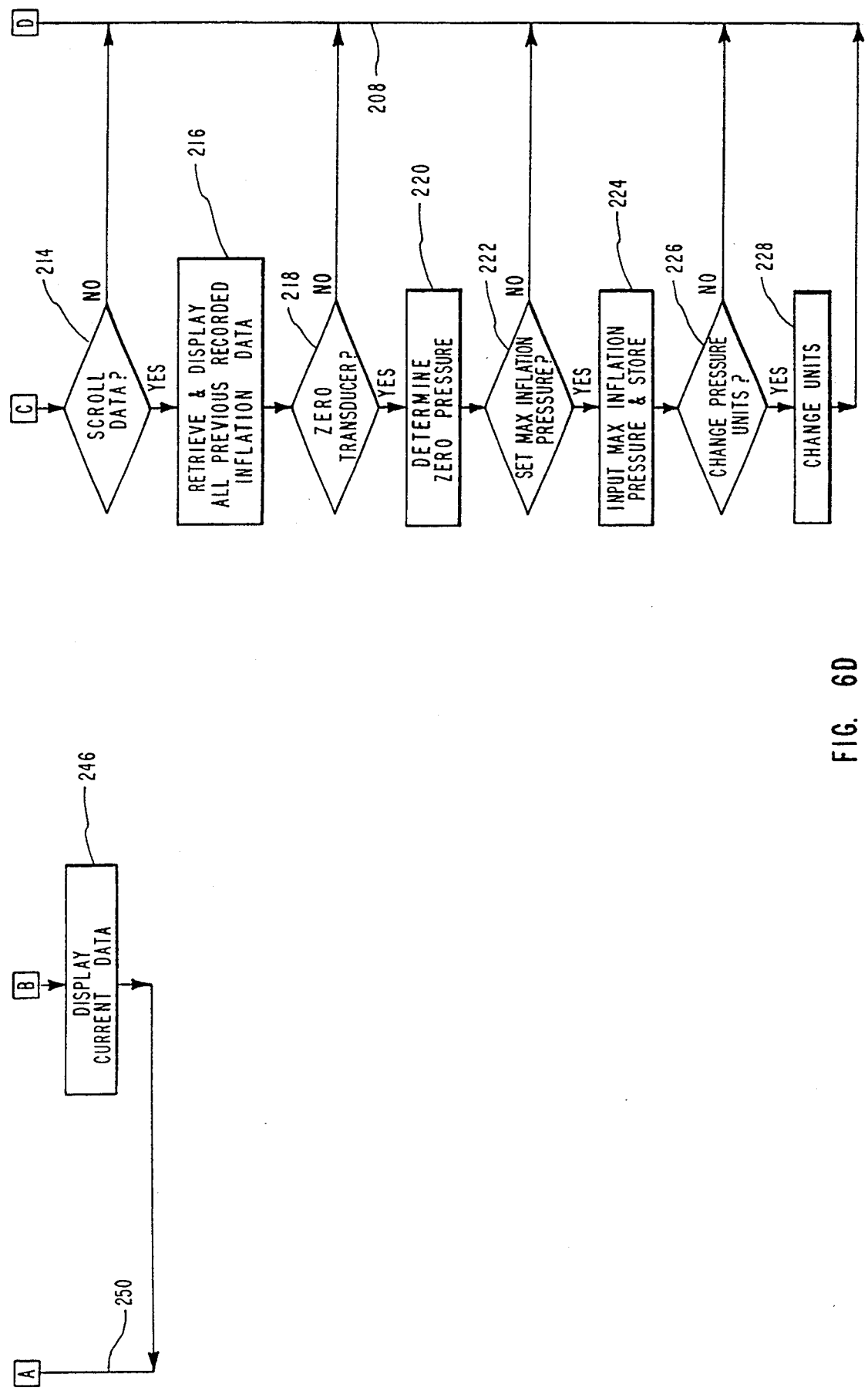
Figure 6E:
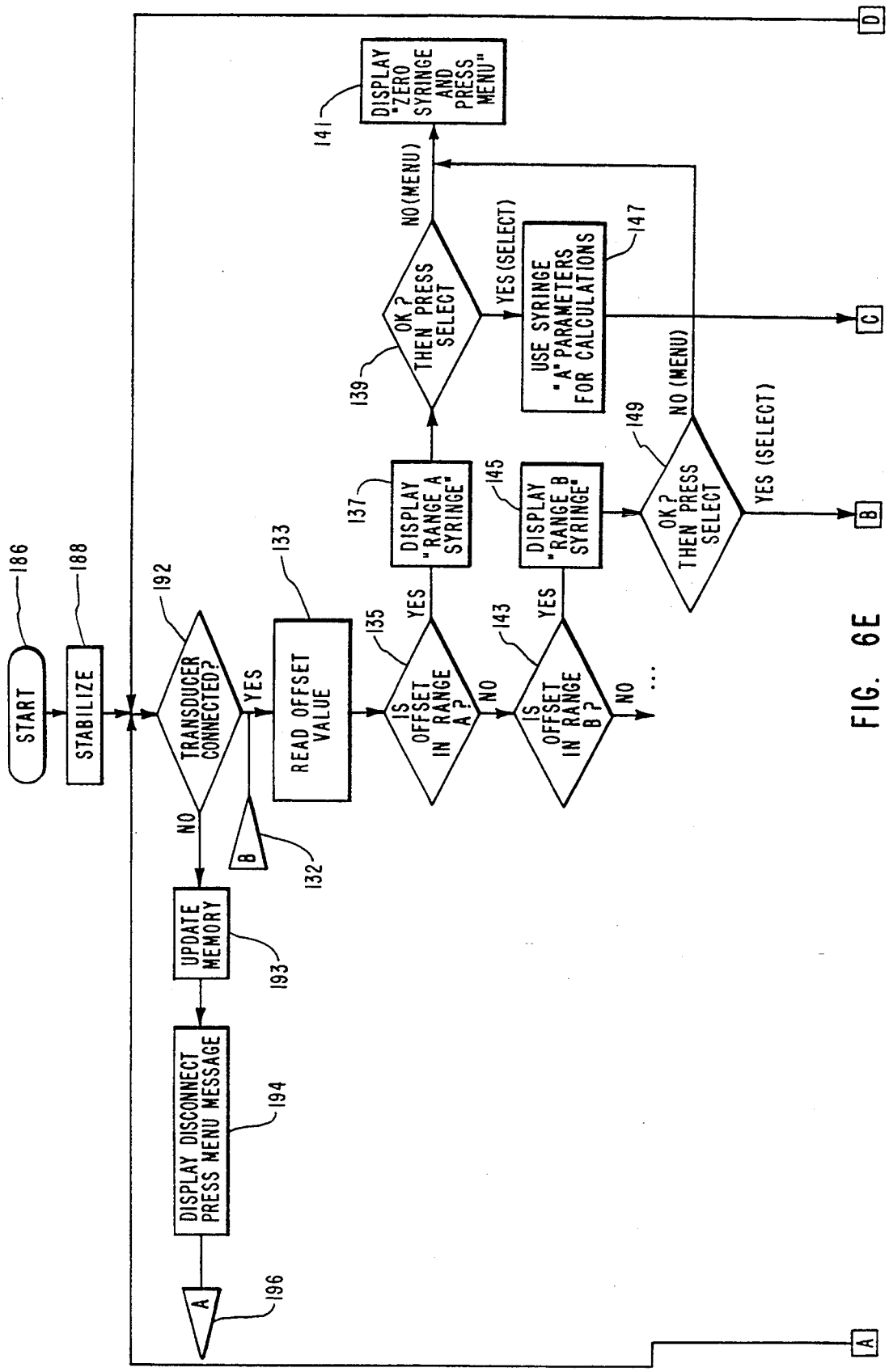
Figure 6F:
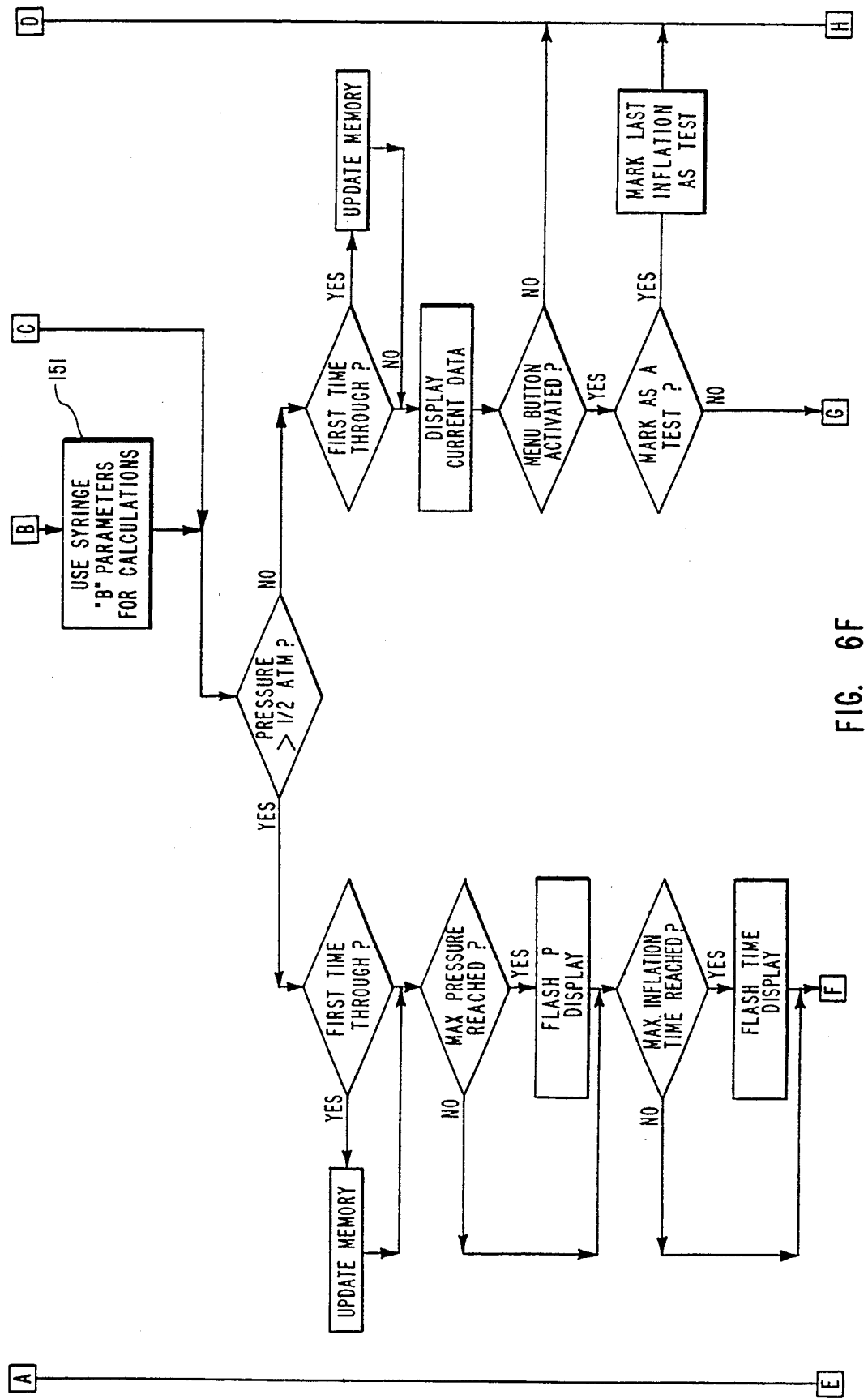

As discussed in conjunction with the same method described for controller 20 in FIG. 6E, this method can advantageously be used to identify different types of syringes that may be useful for different types of applications or patients. In this manner, the system can identify whether the correct type of syringe has been placed into use for the intended application or the type of patient for which the procedure is being conducted.

Figure 19I:
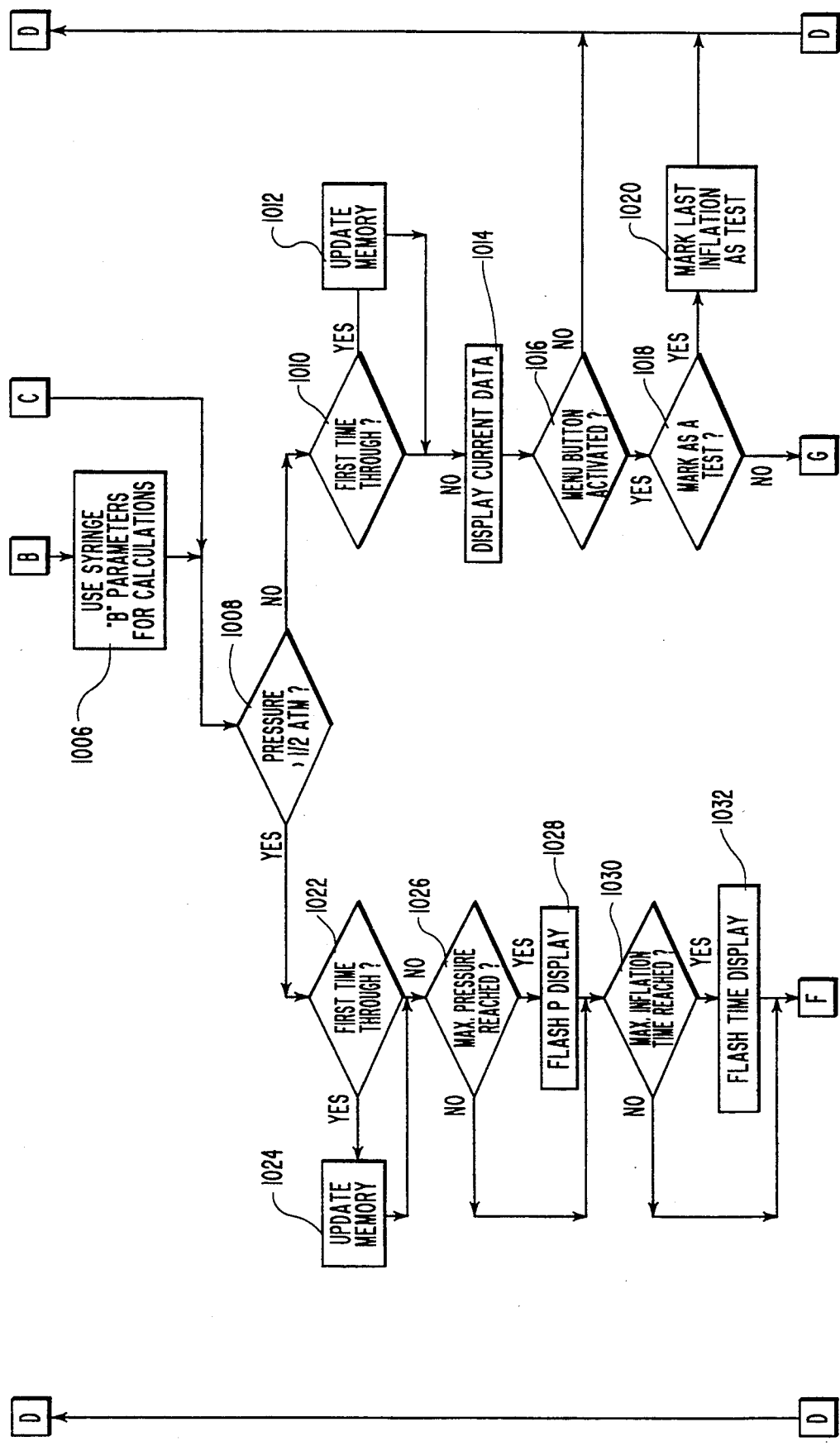
Figure 19J:
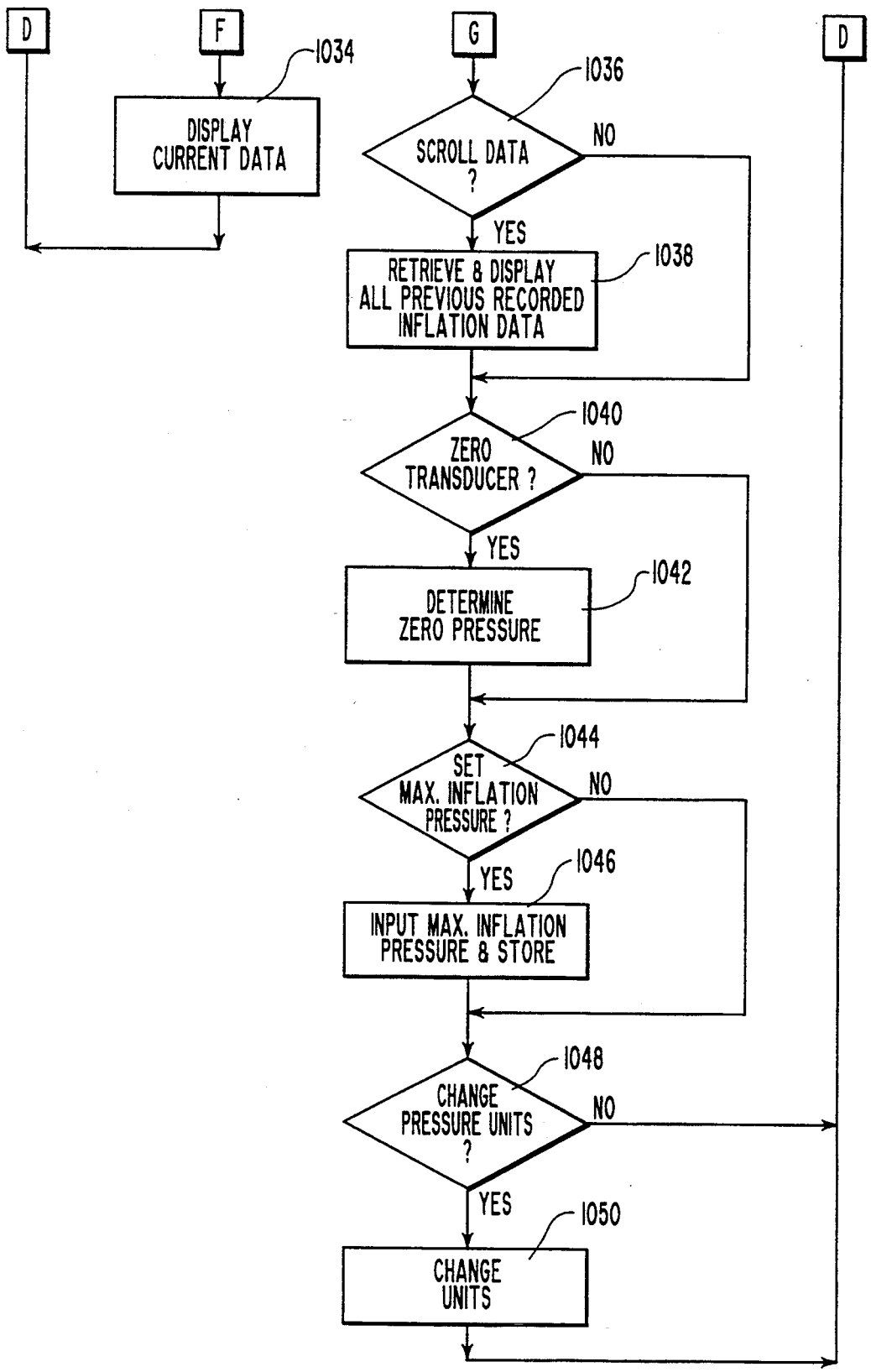

Thus, the system proceeds to identify the type of syringe attached in a manner identical to the method of FIG. 6E. Having done so, the remaining digital processing steps, which are illustrated at FIGS. 19I-19J starting at step 1008 (FIG. 19I) are the same as those which have previously been described in connection with the embodiment of FIGS. 19A-19F.

Returning to FIG. 19H, if the system determines at step 890 that the measured offset value is not within a first range, range A, the system then moves to step 892 where a similar determination is made for the next range of offset values, range B. At steps 1002, 1004 and 1006 the system follows the same type of program steps previously described in connection with steps 894, 896 and 1000. In this fashion the system continues to check until it determines which selected range of offset values corresponds to the type of transducer 42 which is contained on the syringe that has been connected for use, identifies the user of this and then awaits for the user to confirm that this is the proper type of transducer with the appropriate parameters for the selected procedure or type of patient.

Thereafter, the system then carries out step 864 where data is read from the receiver circuitry 584 and it is determined whether the transmission data is valid (step 874), in the same manner as previously described in conjunction with the embodiment of FIG. 19D. Also, in the same manner as described above for FIG. 19D, the system proceeds to check for the power on signal (step 876) and for other errors detected by the detachable electronic circuit module 398d (step 880). If no errors are indicated, the system will proceed to step 888 (FIG. 19H) and continue to monitor and process the inflation data transmitted by the detachable electronic circuit module 398D, in the same manner as described above.

It will be appreciated that the second digital processor (590 in FIG. 17), is preferably a 8032 microprocessor (as in controller 20 discussed in conjunction with FIG. 4) as identified in Table I, and could be programmed so as to implement the above-described method using any one of a variety of different programming languages and programming techniques.

The invention may be embodied in other specific forms without departing from its spirit or essential characteristics. Accordingly, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

TABLE I

| Schematic Reference | Part |
|---|---|
| X1 | 11.059 MHZ |
| C3 | 10Mfd |

TABLE I-continued

| Schematic Reference | Part |
|---|---|
| R1 | 8.2K |
| U1 | 8032 |
| U2 | 74HC573 |
| C5, C7, C14 | .01Mfd |
| C1, C2 | 33pf |
| P1 | CONNECTOR DB25F AMP 745389-1 |
| U4 | DS1243 |
| U5, U6, U7 | DL3416 SIEMENS |
| U8 | ADC0834 TI |
| U9 | MAX233 |
| D1 | IN5291 |
| U3 | 27256 |
| U11 | UA7805UC FAIRCHILD |
| C4 | 4700 Mfd |
| PCB 1 | Printed circuit board |
| JP3 | Female RJ-11 (6 pos-4 wire) |
| JP1 | HEADER 4 |
| J1 | AC line cord |
| R17 | MMSI TRANSDUCER |
| U10 | LM324 |
| R5 | 10K DIP |
| R7, R9, R10, R11 | 10K DIP |
| K6 | 10K-15T VRN 752-208-103 |
| R12, R13 | 100K |
| R2 | 10K |
| C6, C8, C9, C10, C11, C12, C13 | .01 Mfd |
| C15, C16 | .2 Mfd |
| T1 | Toltek Custom transformer |
| D2 | GI 2KBP04 |
| F1 | .25 AMP |
| SW1 | Micro Switch & Cover |

TABLE II

| Schematic Reference | Part |
|---|---|
| Y1 | CST 4.19 MHZ (KYOCERA) |
| U2 | LM324DT (SGS) |
| B1, B2 | CR20162HM (Panasonic) |
| RN1 | 100K (CTS) |
| R1, R3, R4, R6, R8 | NRC12100KFTR (NIC) |
| R2 | NRC127.32KFTR (NIC) |
| R5 | NRC121MEGFTR (NIC) |
| U1 | NEC75328GC173/3B9 (NEC) |
| D1, D2, D3, D4 | MTBL3410 (MARKTECH) |

We claim:

1. A system for monitoring inflation or deflation of a balloon-type member and for displaying monitored inflation or deflation data, the system comprising:
  a syringe for connection to the member through tubing, the syringe comprising a barrel and a plunger selectively operable to inflate the member by applying fluid pressure to the member through the tubing by sliding the plunger within the barrel, and operable to deflate the member by withdrawing the plunger from the barrel;
  transducer means for sensing fluid pressure and for outputting an electrical pressure signal proportional to the sensed fluid pressure, the transducer means adapted for placement in communication with the fluid pressure within the syringe and the tubing connected thereto;
  detachable electronic circuit means for receiving the electrical pressure signal when operatively coupled to the syringe or tubing, and for thereafter electronically processing the pressure signal;

display means for outputting a visual display of monitored data derived from the electrical pressure signal; and means for operatively coupling the detachable electronic circuit means to the syringe or tubing, and the electrical pressure signal being thereafter received by the detachable electronic circuit means so as to enable the data to be derived and monitored, and the detachable electronic circuit means being detachable from the syringe for re-use in another system upon completion of monitoring.

2. A system as defined in claim 1 further comprising a power means for providing electrical power to the transducer means and the detachable electronic circuit means.

3. A system as defined in claim 2 wherein the power means comprises a battery.

4. A system as defined in claim 2 wherein the system further comprises conductive means mounted on the syringe for providing a releasable electrical connection between at least one of the transducer means Or the battery means and the detachable electronic circuit means when the detachable electronic circuit means is mounted to the syringe.

5. A system as defined in claim 4 wherein the transducer means and the power means are mounted to the syringe.

6. A system as defined in claim 4 wherein the transducer means is mounted to the syringe and the power means is included as part of the detachable electronic circuit means.

7. A system as defined in claim 4 wherein the transducer means is included as part of the detachable electronic circuit means and the power means is mounted to the syringe.

8. A system as defined in claim 4 wherein the conductive means comprises:
at least one first electrical connector mounted on the syringe barrel;
at least one second electrical connector mounted on the detachable electronic circuit means; and
wherein the first electrical connector is placed in electrical contact with the second electrical connector when the detachable electronic circuit means is mounted to the syringe.

9. A system as defined in claim 2 wherein the power means and the transducer means are both included as part of the detachable electronic circuit means.

10. A system as defined in claims 1 or 9 wherein the means for operatively coupling comprises a housing mounted on the syringe and comprising means for receiving and holding in a releasable manner the detachable electronic circuit means in an enclosed compartment formed by the housing.

11. A system as defined in claim 10 wherein the housing comprises door means for selectively opening and closing an entrance to the compartment, whereby the detachable electronic circuit means is completely encapsulated within the compartment of the housing when the door means is closed.

12. A system as defined in claim 11 wherein the housing further comprises:
at least one switch means for electronically activating the detachable electronic circuit means; and
a transparent viewing portion that allows for the visual inspection of the detachable electronic circuit means when enclosed within the housing.

13. A system as defined in claims 7 or 9 further comprising fluid coupling means for providing fluid communication between the transducer means and the fluid pressures within the syringe barrel.

14. A system as defined in any one of claims 1, 5, 6, 7 or 9 wherein the detachable electronic circuit means comprises:
means for amplifying the electrical pressure signal;
means for converting the amplified electrical pressure signal from an analog to a digital form;
digital processor means for processing the digital form of the electrical pressure signal so as to derive therefrom digital transmission data which represents the magnitude of the applied pressure and the length of time the pressure is applied to the member;
data memory means for storing the digital transmission data derived by the digital processor means;
program memory means for storing machine-readable instructions utilized by the digital processor means to derive and store the digital transmission data for transmission; and
transmission means for converting the digital transmission data derived by the digital processor means into a transmission signal and for wirelessly transmitting the transmission data via the transmission signal.

15. A system as defined in claim 14 further comprising a remote console means for receiving the transmission signal from the transmission means and for electronically processing the transmission signal.

16. A system as defined in claim 15 wherein the display means is electrically connected and included as part of the remote console means.

17. A system as defined in claim 15 wherein the remote console means comprises:
receiver means for receiving the transmission signal transmitted by the transmission means and for converting the transmission signal into a digital form;
digital processor means for processing the digital form of the received transmission signal so as to derive, store and display digital data which represents the magnitude of the applied pressure and the length of time the pressure is applied to the member;
data memory means for storing the digital data derived by the digital processor means; and
program memory means for storing machine-readable instructions utilized by the digital processor means to monitor the detachable electronic circuit means and to derive, store, retrieve and display the digital data.

18. A system as defined in claim 17 wherein the transmission means comprises RF transmitter circuit means for wirelessly transmitting the transmission signal as a radio frequency signal having a predetermined radio frequency.

19. A system as defined in claim 18 wherein the receiver means comprises RF receiver circuit means for receiving the RF transmission signal transmitted by the RF transmitter circuit means.

20. A system as defined in claim 17 wherein the transmission means comprises infrared transmitter circuit means for wirelessly transmitting the transmission signal as a modulated infrared light beam signal.

21. A system as defined in claim 20 wherein the receiver means comprises infrared receiver circuit means for receiving the infrared transmission signal transmitted by the infrared transmitter circuit means.

22. A system as defined in claim 1 wherein the detachable electronic circuit means comprises:
   means for amplifying the electrical pressure signal;
   means for converting the amplified electrical pressure signal from an analog to a digital form;
   digital processor means for processing the digital form of the electrical pressure signal so as to derive therefrom digital data which represents the magnitude of the applied pressure and the length of time the pressure is applied to the member;
   data memory means for storing the digital data derived by the digital processor means; and
   program memory means for storing machine-readable instructions utilized by the digital processor means to derive, store, retrieve and display the digital data.

23. A system as defined in any one of claims 1, 5, 6, 7, 9, or 22 wherein the display means is electrically connected and is included as part of the detachable electronic circuit means.

24. A disposable syringe apparatus for use with a system for generating a series of discrete inflations or deflations of a balloon located at a distal end of a balloon catheter adapted for coupling to the syringe apparatus through tubing, wherein the system is adapted for displaying data corresponding to each said discrete inflation or deflation and wherein the system includes a transducer for sensing the applied pressure of said inflations or deflations and for generating an electrical pressure signal that is proportional to said sensed pressure and wherein the system further includes a detachable and reusable electronic circuit module for electronically processing the electrical pressure signal, the disposable syringe apparatus comprising:
   a barrel adapted for connection through said tubing to the balloon that is located at the distal end of said balloon catheter;
   a plunger received within said barrel and operable therein so as to selectively apply and then release fluid pressure on said balloon by movement of the plunger within the barrel; and
   means for operatively and detachably coupling the detachable and reusable electronic circuit module to one of the syringe barrel or tubing while maintaining patient sterility relative to the circuit module, and the electronic pressure signal thereafter being received by the electronic circuit module while the inflation data is monitored, and the electronic circuit module being thereafter detachable for re-use in another system upon completion of monitoring, while the syringe apparatus is disposable.

25. A detachable and reusable electronic circuit module for use with a system for generating a series of discrete inflations or deflations of a balloon located at a distal end of a balloon catheter that is coupled to a disposable syringe through tubing, the disposable syringe being comprised of a barrel, a plunger, and a housing for detachably receiving the detachable electronic circuit module, and wherein the system further includes a transducer for sensing the applied pressure of said inflations and deflations and for generating an electrical pressure signal that is proportional to said sensed pressure, and a display for outputting a visual display of the sensed fluid pressure, the detachable electronic circuit module comprising:
   means for receiving the electrical pressure signal when the circuit module is operatively coupled to the syringe or tubing, and thereafter electronically processing the electrical pressure signal; and
   means for operatively coupling the electronic circuit module to the syringe or tubing, and the electrical pressure signal being thereafter received by the detachable electronic circuit module while the inflation or deflation data is monitored, and the detachable circuit module being thereafter detachable for re-use in another system upon completion of monitoring.

26. A system for monitoring inflation and deflation of a balloon-type member and for displaying inflation or deflation data, the system comprising:
   a syringe adapted for connection to the member through tubing, the syringe comprising a barrel and a plunger selectively operable to inflate the member by applying fluid pressure to the member through the tubing by sliding the plunger within the barrel, and operable to deflate the member by withdrawing the plunger from the barrel;
   transducer means for sensing fluid pressure and for outputting an electrical pressure signal proportional to the sensed fluid pressure, the transducer means being adored for placement in communication with the fluid pressure within the syringe and the tubing connected thereto;
   detachable electronic circuit means for receiving the electrical pressure signal when the circuit means is operatively coupled to the syringe or tubing, and for thereafter electronically processing the pressure signal;
   display means for outputting a visual display of the inflation or deflation data by displaying the magnitude of the sensed fluid pressure and the corresponding length of time the pressure is sensed;
   means for operatively coupling the detachable electronic circuit means to the syringe or tubing, and the electrical pressure signal being received by the detachable electronic circuit means while the inflation or deflation data is monitored, and the detachable electronic circuit means being detachable from the syringe for re-use in another system upon completion of monitoring;
   power means for providing electrical power to the transducer means and the detachable electronic circuit means; and
   conductive means for providing a releasable electrical connection between at least one of the transducer means or the battery means and the detachable electronic circuit means when the detachable electronic circuit means is operatively mounted to the syringe or tubing.

27. A system as defined in claim 26 wherein the transducer means is mounted to the syringe.

28. A system as defined in claim 26 wherein the transducer means is included as part of the detachable electronic circuit means.

29. A system as defined in claim 26 wherein the conductive means comprises:
   at least one first electrical connector mounted on the syringe barrel; and
   at least one second electrical connector mounted on the detachable electronic circuit means; and wherein the first electrical connector is placed in electrical contact with the second electrical connector when the detachable electronic circuit means is mounted to the syringe thereby providing a conductive path between the detachable electronic circuit means and the syringe.

30. A system as defined in claim 29 wherein the detachable electronic circuit means comprises:
   means for amplifying the electrical pressure signal;
   means for converting the amplified electrical pressure signal from an analog to a digital form;
   digital processor means for processing the digital form of the electrical pressure signal so as to derive therefrom digital data which represents the magnitude of the applied pressure and the length of time the pressure is applied to the member;
   data memory means for storing the digital data derived by the digital processor means; and
   program memory means for storing machine-readable instructions utilized by the digital processor means to derive, store, retrieve and display the digital data.

31. A system as defined in any one of claims 26 to 30 wherein the display means is electrically connected and is included as part of the detachable electronic circuit means.

32. A system as defined in claim 29 wherein the detachable electronic circuit means comprises:
   means for amplifying the electrical pressure signal;
   means for converting the amplified electrical pressure signal from an analog to a digital form;
   digital processor means for processing the digital form of the electrical pressure signal so as to derive therefrom digital transmission data which represents the magnitude of the applied pressure and the length of time the pressure is applied to the member;
   data memory means for storing the digital transmission data derived by the digital processor means;
   program memory means for storing machine-readable instructions utilized by the digital processor means to derive and store the digital transmission data for transmission; and
   transmission means for converting the digital transmission data derived by the digital processor means into a transmission signal and for wirelessly transmitting the transmission data via the transmission signal.

33. A system as defined in claim 32 further comprising a remote console means for receiving the transmission signal from the transmission means and for electronically processing the transmission signal.

34. A system as defined in claim 33 wherein the display means is electrically connected and included as part of the remote console means.

35. A system as defined in claim 33 wherein the remote console means comprises:
   receiver means for receiving the transmission signal transmitted by the transmission means and for converting the transmission signal into a digital form;
   digital processor means for processing the digital form of the received transmission signal so as to derive, store and display digital data which represents the magnitude of the applied pressure and the length of time the pressure is applied to the member;
   data memory means for storing the digital data derived by the digital processor means; and
   program memory means for storing machine-readable instructions utilized by the digital processor means to monitor the detachable electronic circuit means and to derive, store, retrieve and display the digital data.

36. A system as defined in claim 35 wherein the transmission means comprises RF transmitter circuit means for wirelessly transmitting the transmission signal as a radio frequency signal having a predetermined radio frequency.

37. A system as defined in claim 36 wherein the receiver means comprises RF receiver circuit means for receiving the RF transmission signal transmitted by the RF transmitter circuit means.

38. A system as defined in claim 35 wherein the transmission means comprises infrared transmitter circuit means for wirelessly transmitting the transmission signal as a modulated infrared light beam signal.

39. A system as defined in claim 38 wherein the receiver means comprises infrared receiver circuit means for receiving the infrared transmission signal transmitted by the infrared transmitter circuit means.

* * * * *